(12) United States Patent
Hrincius et al.

(10) Patent No.: US 9,637,523 B2
(45) Date of Patent: May 2, 2017

(54) METHODS AND PEPTIDES FOR PREVENTING AND TREATING A BCR-ABL AND A C-ABL ASSOCIATED DISEASE

(71) Applicant: Westfaelische Wilhelms-Universitaet Muenster, Muenster (DE)

(72) Inventors: Eike-Roman Hrincius, Muenster (DE); Stephan Ludwig, Muenster (DE); Christina Ehrhardt, Muenster (DE)

(73) Assignee: Westfaelische Wilhelms-Universitaet Muenster, Muenster (DE)

( * ) Notice: Subject to any disclaimer, the term of this patent is extended or adjusted under 35 U.S.C. 154(b) by 0 days.

(21) Appl. No.: 14/422,918

(22) PCT Filed: Aug. 30, 2013

(86) PCT No.: PCT/EP2013/068032
§ 371 (c)(1),
(2) Date: Feb. 20, 2015

(87) PCT Pub. No.: WO2014/033281
PCT Pub. Date: Mar. 6, 2014

(65) Prior Publication Data
US 2015/0218229 A1 Aug. 6, 2015

(30) Foreign Application Priority Data
Aug. 31, 2012 (EP) .................................... 12182644

(51) Int. Cl.
| | | |
|---|---|---|
| *A61K 38/00* | (2006.01) | |
| *C07K 14/005* | (2006.01) | |
| *A61P 35/02* | (2006.01) | |
| *C07K 14/82* | (2006.01) | |
| *A61K 38/16* | (2006.01) | |
| *C12Q 1/48* | (2006.01) | |
| *C12N 9/12* | (2006.01) | |
| *G01N 33/50* | (2006.01) | |
| *A61K 48/00* | (2006.01) | |

(52) U.S. Cl.
CPC ............ *C07K 14/005* (2013.01); *A61K 38/16* (2013.01); *A61K 38/162* (2013.01); *C07K 14/82* (2013.01); *C12N 9/12* (2013.01); *C12N 9/1205* (2013.01); *C12Q 1/485* (2013.01); *C12Y 207/10002* (2013.01); *C12Y 207/11001* (2013.01); *G01N 33/5011* (2013.01); *A61K 38/00* (2013.01); *A61K 48/005* (2013.01); *C07K 2319/10* (2013.01); *C07K 2319/70* (2013.01); *C12N 2760/16122* (2013.01); *C12N 2760/16133* (2013.01); *G01N 2333/91205* (2013.01); *G01N 2500/04* (2013.01); *G01N 2500/10* (2013.01)

(58) Field of Classification Search
CPC .. C07K 14/82; C07K 14/005; C07K 2319/10; C07K 2319/70; C12Q 1/485; C12N 9/1205; C12N 2760/16133; C12N 9/12; C12N 2760/16122; A61K 38/162; A61K 38/00; A61K 38/16; A61K 48/005; A61K 2300/00; C12Y 207/11001; C12Y 207/10002; G01N 2333/91205; G01N 33/5011; G01N 2500/10; G01N 2500/04

See application file for complete search history.

(56) References Cited

U.S. PATENT DOCUMENTS 5,595,756 A * 1/1997 Bally et al. .......... A61K 9/1272
264/4.1

FOREIGN PATENT DOCUMENTS

| WO | 95/31545 | 11/1995 |
|---|---|---|
| WO | 96/25520 | 8/1996 |
| WO | 03/006486 | 1/2003 |

OTHER PUBLICATIONS

Li et al, Heterologous interactions between NS1 proteins from different influenza A virus subtypes/strains, Science China Life Sciences, 2012, 55, pp. 507-515.*
Rudinger, Peptide Hormones, JA Parsons, Ed., 1976, pp. 1-7.*
SIGMA, 2004, pp. 1-2.*
Berendsen, A Glimpse of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Greuber et al, Role of ABL family kinases in cancer: from leukaemia to solid tumours, Nature Reviews/Cancer, 2013, 13, pp. 559-571.*
Stegmeier et al, Targeted Cancer Therapies in the Twenty-First Century: Lessons From Imatinib, Clinical Pharmacology & Therapeutics, 2010, 87, pp. 543-552.*
Cellular and Molecular Basis of Cancer from Merck Manual, 2008, pp. 1-5, accessed Nov. 7, 2012.*
Sporn, B and Suh, N, Chemoprevention of cancer, Carcinogenesis, 2000, 21, pp. 525-530.*
Auerbach. R. et al, Angiogenesis assays: Problems and pitfalls, Cancer and Metastasis Reviews, 2000, 19, pp. 167-172.*
Gura, T. Systems for Identifying New Drugs Are Often Faulty, Science, 1997, 278, pp. 1041-1042.*
Jain R. K., Barriers to Drug Delivery in Solid Tumors, Scientific American, 1994, pp. 58-65.*
Cancer Drug Design and Discovery. Neidle, Stephen, ed., Elsevier/ACademic Press, 2008, p. 427-431.*
Lee et al, Sequential Application of Anticancer Drugs Enhances Cell Death by Rewiring Apoptotic Signaling Networks, Cell, 2012, 149, pp. 780-794.*

(Continued)

*Primary Examiner* — Julie Ha
*Assistant Examiner* — Li Ni Komatsu
(74) *Attorney, Agent, or Firm* — Riverside Law LLP

(57) ABSTRACT

The invention provides a combination of an isolated peptide or peptidomimetic that includes the sequence of SEQ ID NO: 1 or a homolog thereof, and an isolated peptide or peptidomimetic that includes the sequence of SEQ ID NO: 2. The invention also provides a method of treating a BCR-ABL associated disease or a c-ABL associated disease in a subject. The method is based on the use of the aforementioned combination of one or more isolated peptides or peptidomimetics.

3 Claims, 14 Drawing Sheets

(56) References Cited

OTHER PUBLICATIONS

Duncan et al, Dynamic Reprogramming of the Kinome in Response to Targeted MEK Inhibition in Triple-Negative Breast Cancer, Cell, 2012, 149, pp. 307-321.*
Bavagnoli et al., "The PDZ-Ligand and Src-Homology Type 3 Domains of Epidemic Avian Influenza Virus NS1 Protein Modulate Human Src Kinase Activity during Viral Infection," *PLoS One*, Nov. 2011, 6(11):e27789.
Brask et al., "Effects on synaptic activity in cultured hippocampal neurons by influenza a viral proteins," *Journal of Neuro Virology*, 2005, 11:395-402.
Dorsey et al., "The Pyrido[2,3-d]pyrimidine Derivative PD180970 Inhibits p210$^{Bcr-Abl}$ Tyrosine Kinase and Induces Apoptosis of K562 Leukemic Cells," *Cancer Research*, Jun. 2000, 60:3127-3131.
Heikkinen et al., "Avian and 1918 Spanish Influenza Virus NS1 Proteins Bind to Crk/CrkL Src Homology 3 Domains to Activate Host Cell Signaling," *J. Biol. Chem.*, 2008, 283:5719-5727.
Ron de Jong et al., "Tyrosine 207 in CRKL is the BCR/ABL phosphorylation site," *Oncogene*, 1997, 14:507-513.
WeiZhong et al., "Heterologous interactions between NS1 proteins from different influenza A virus subtypes/strains," *Science China Life Sciences*, Jun. 2012, 55(6):507-515.
Waller et al., "Growth Inhibition of Ph$^+$Progenitor Cells from CML Patients Using the Tyrosine Kinase Inhibitor CGP57148B*," *Anticancer Research*, 2000, 20:809-814.

* cited by examiner

Fig. 1

FPV/Rostock/NS1-rec.: -, wt, P212S, P215T  18h  MOI:1

- P ATF2 (pT71)
- ATF2
- P CRKL (pY207)
- CRKL
- NS1
- eIF4E 1 2 3 4

Fig. 2A

8h — Input | IP: CRKL | serum

MOI=5: -, FPV, PR8, -, FPV, PR8, FPV, PR8

- (P)Tyrosin
- CRKL
- NS1

1 2 3 4 5 6 7 8

A549

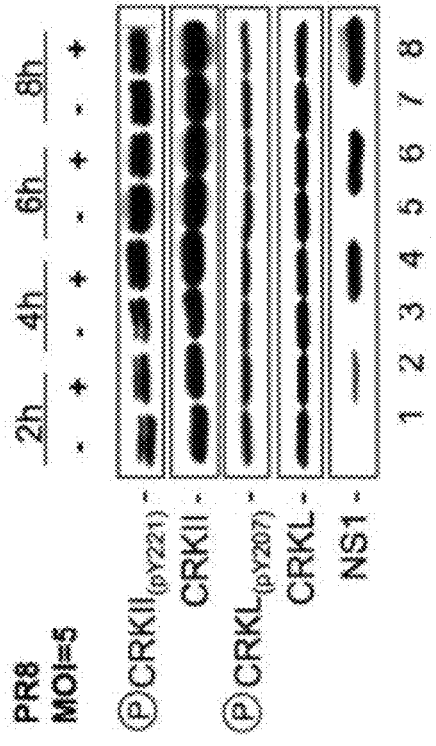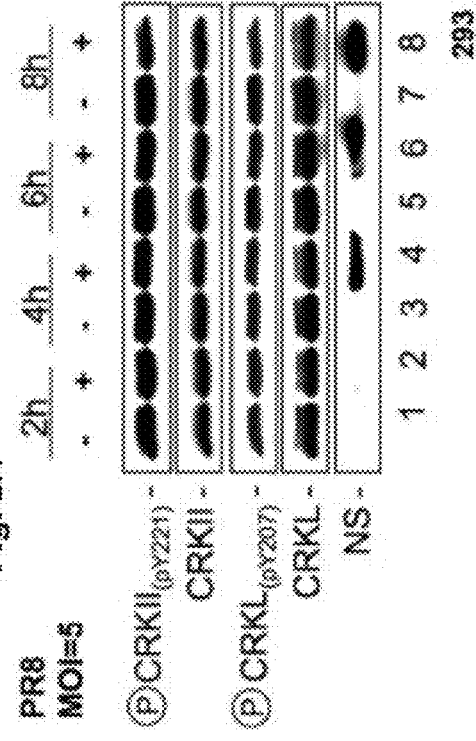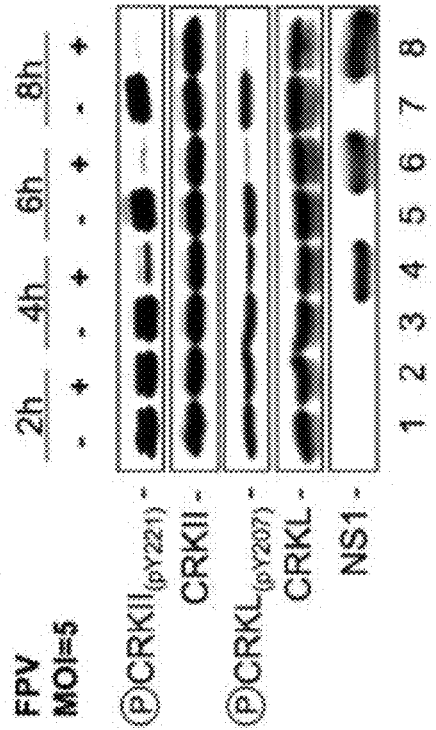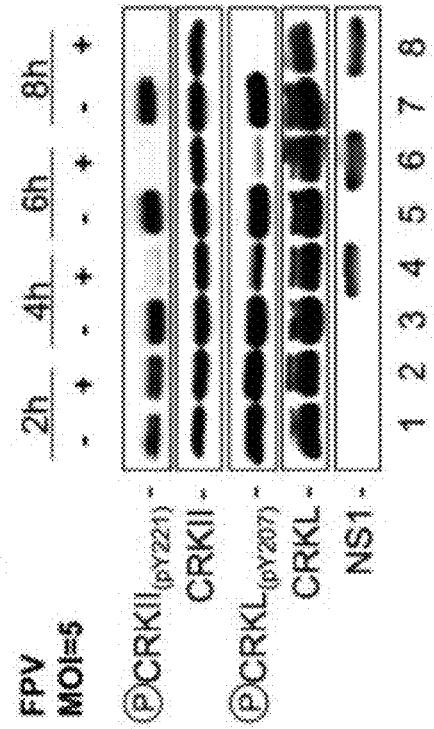

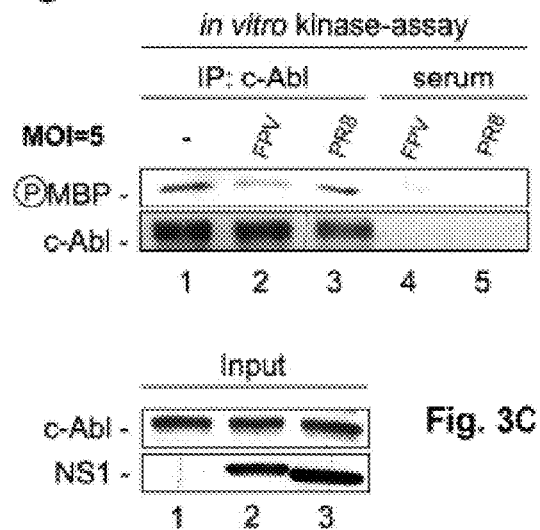
Fig. 3A
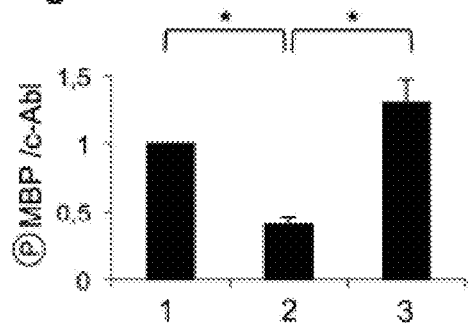
Fig. 3B
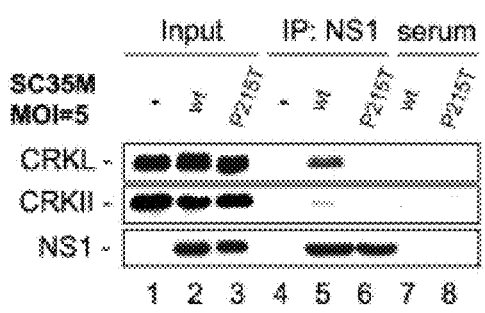
Fig. 4A
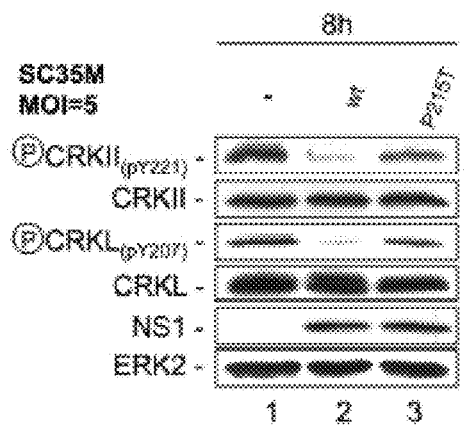
Fig. 4B
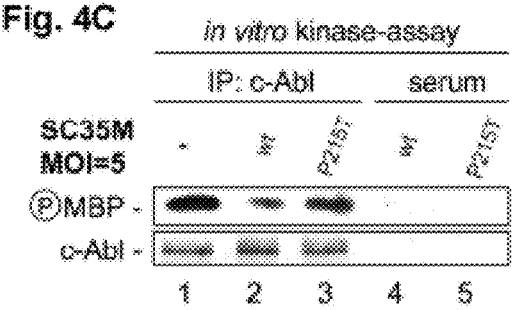
Fig. 4C
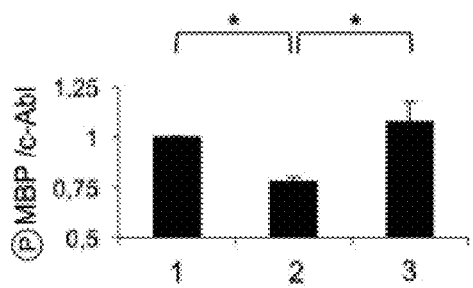
(cont. on next page)

Fig. 4C (cont. from prev. page)
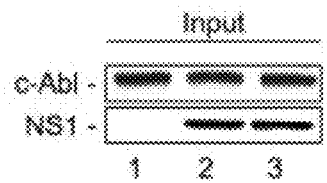
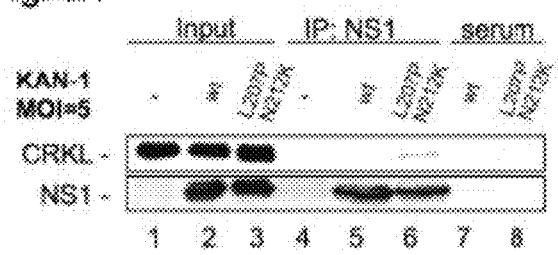
Fig. 5A
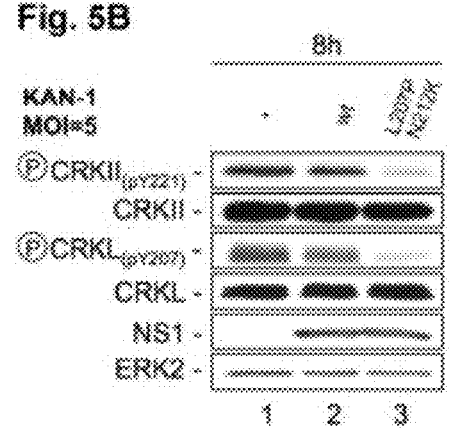
Fig. 5B
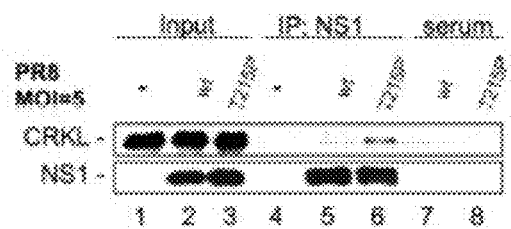
Fig. 5C
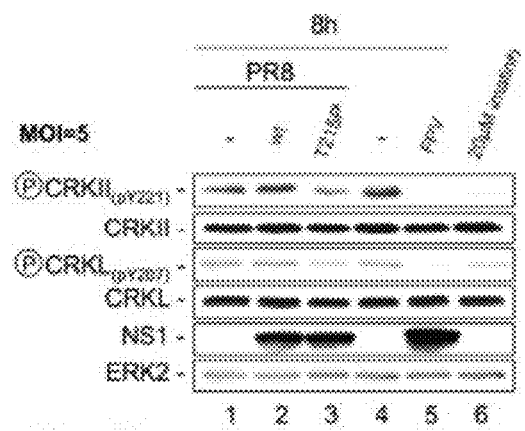
Fig. 5D

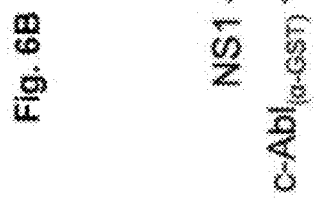
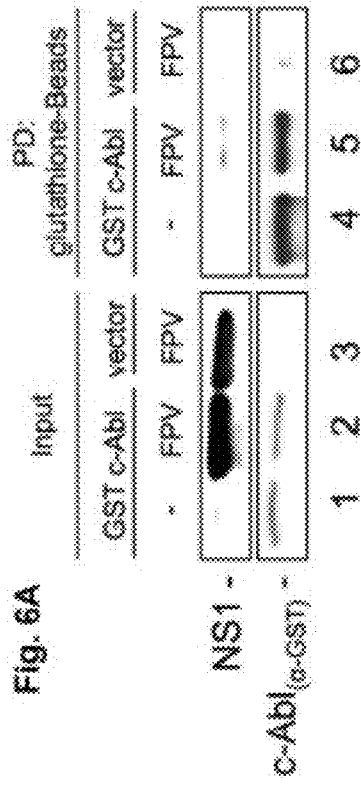
Fig. 6A
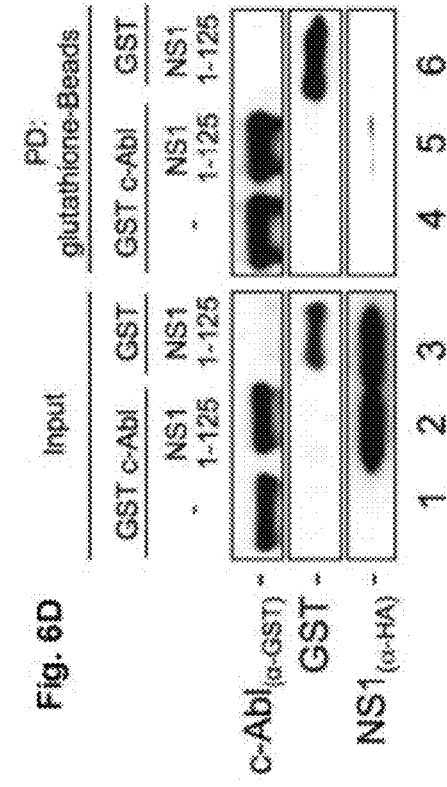
Fig. 6B
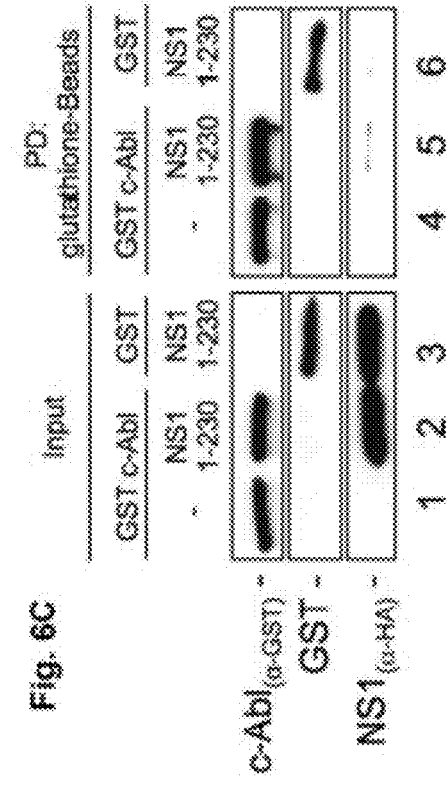
Fig. 6C
Fig. 6D

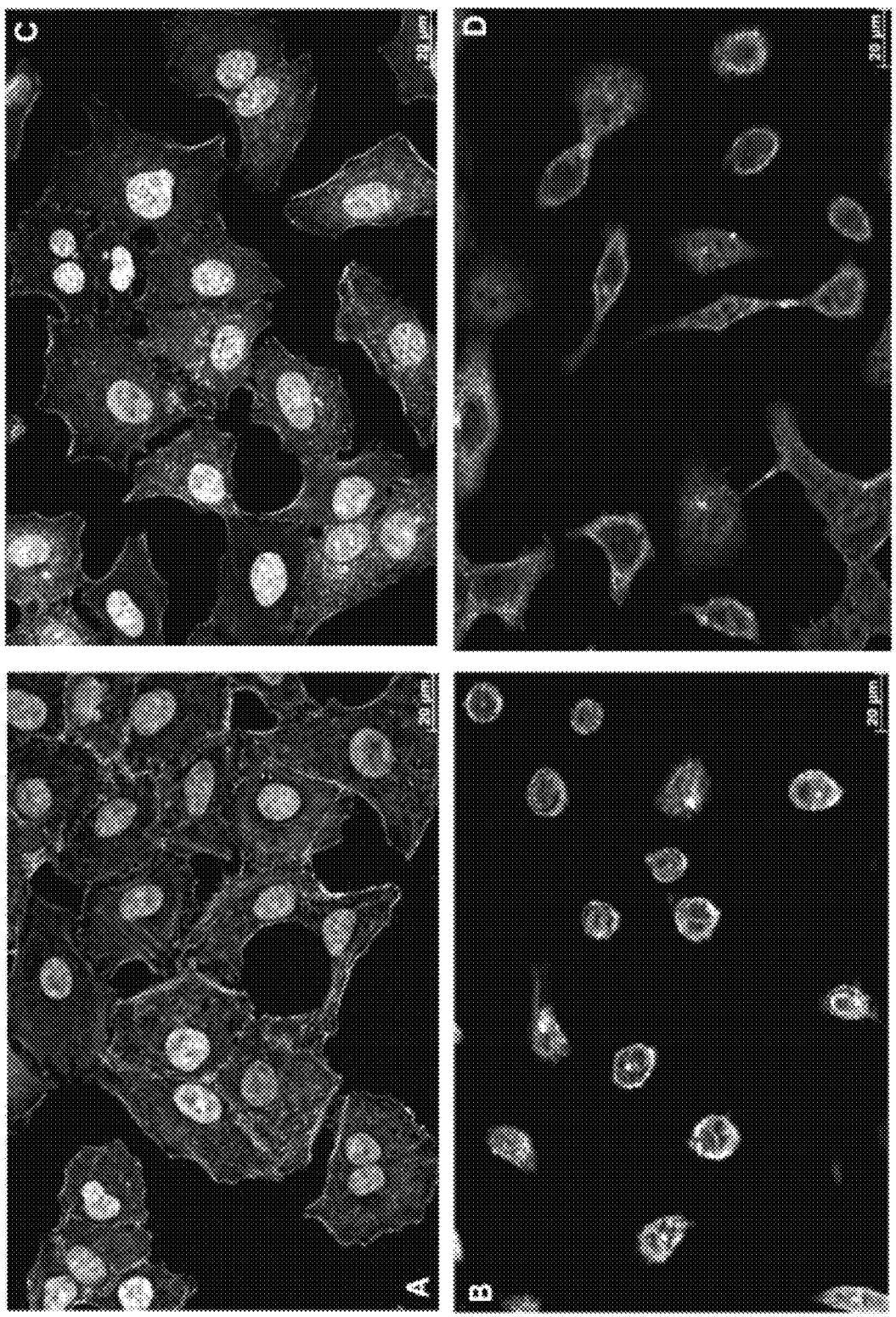
Fig. 9 (cont. on next page)

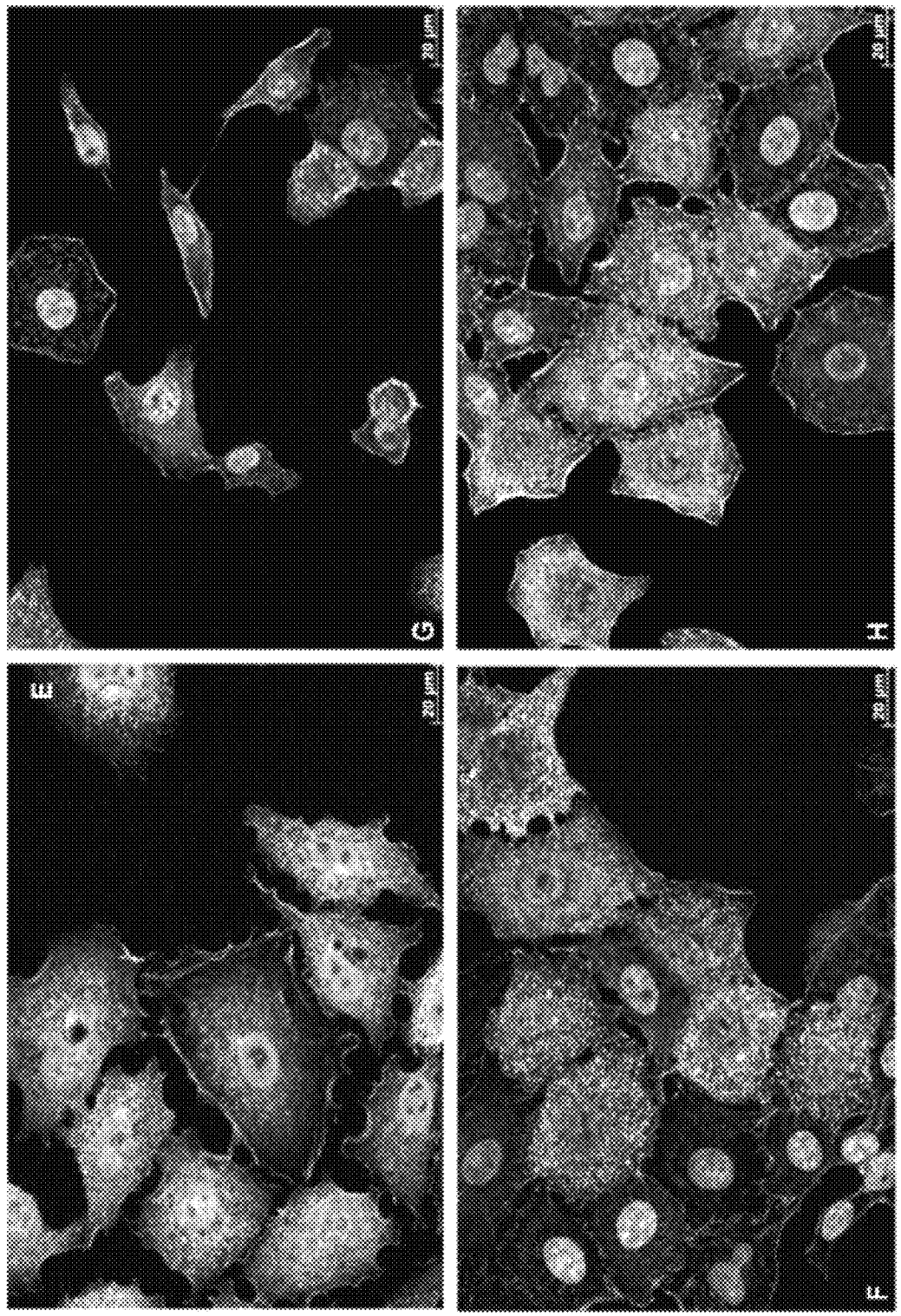
Fig. 9 (cont. on next page)

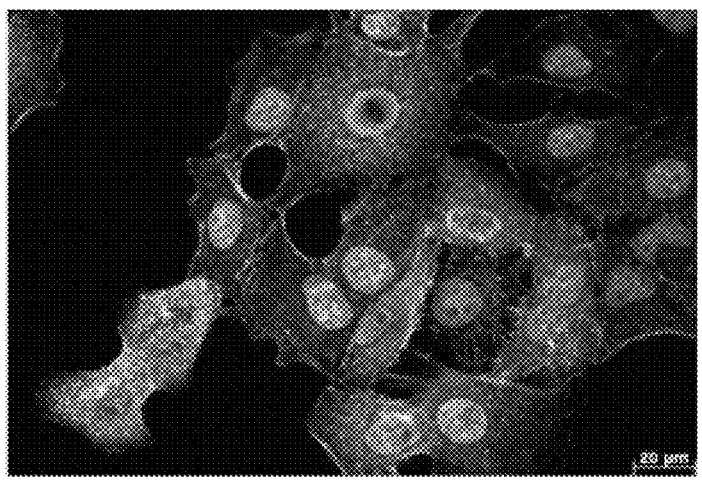
Fig. 9 (cont. from prev. page)
| SH3 class II binding motif | PX𝜙PX+ |
|---|---|
| FPV/79 (H7N7) | 212 PPLPPK |
| PR8 (H1N1) | 212 PPLPK |
| SC35M (H7N7) | 212 PPLPPK |
| KAN-1 (H5N1) | 212 LPLPPN |
| Human IAV consensus | 212 PPLTPK |
| Avian IAV consensus | 212 PPLPPK |
| Avian and human H5N1 strains consensus | 212 LPLPPN |
Fig. 10
Fig. 11A
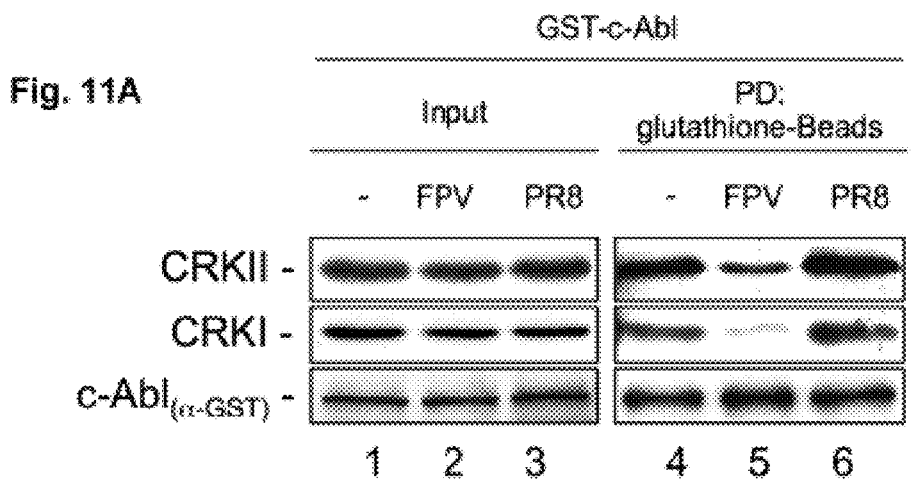

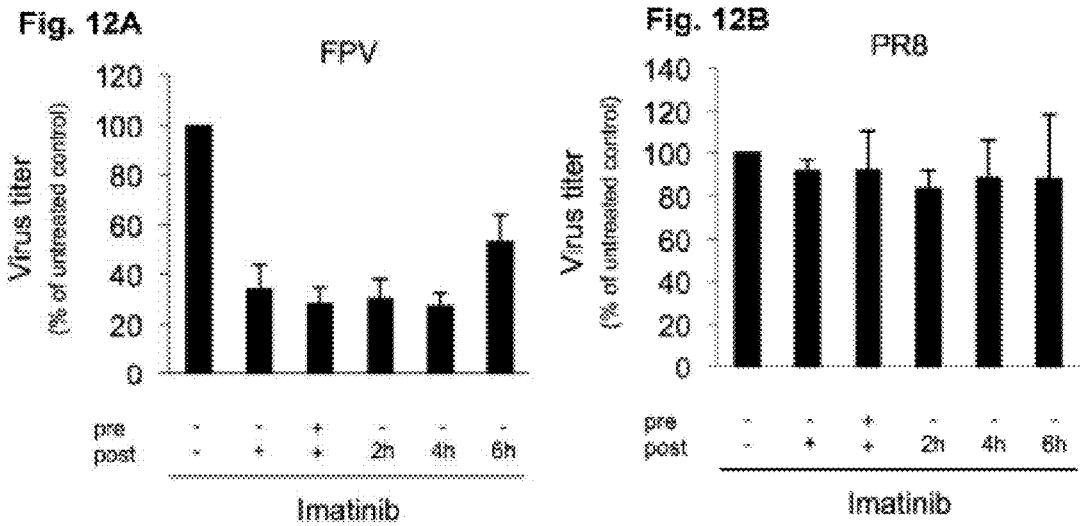
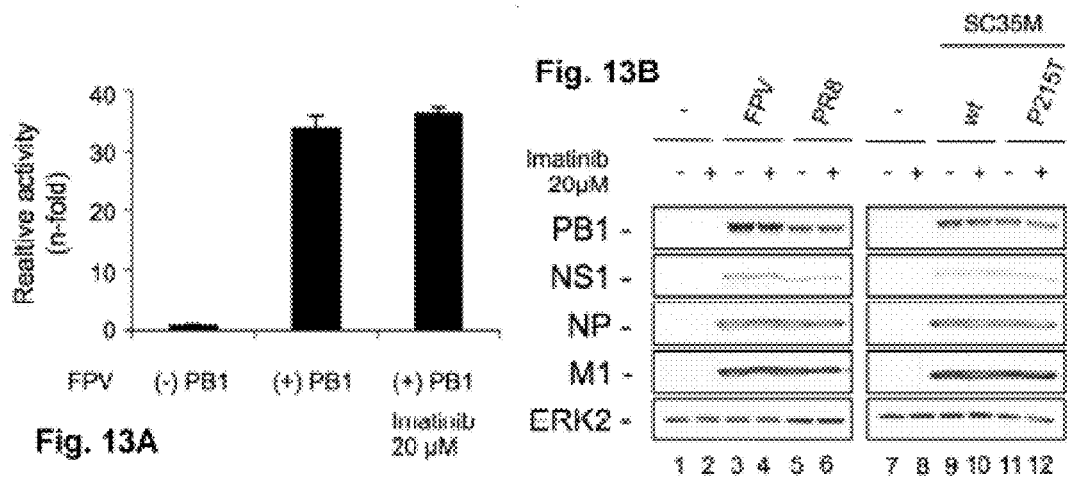
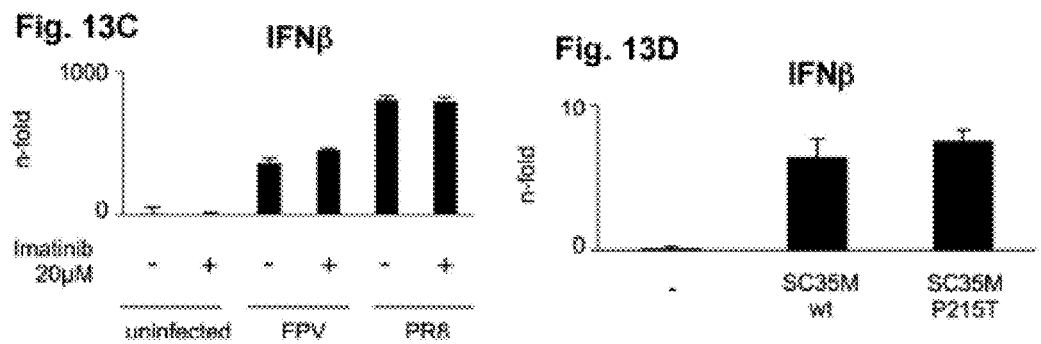

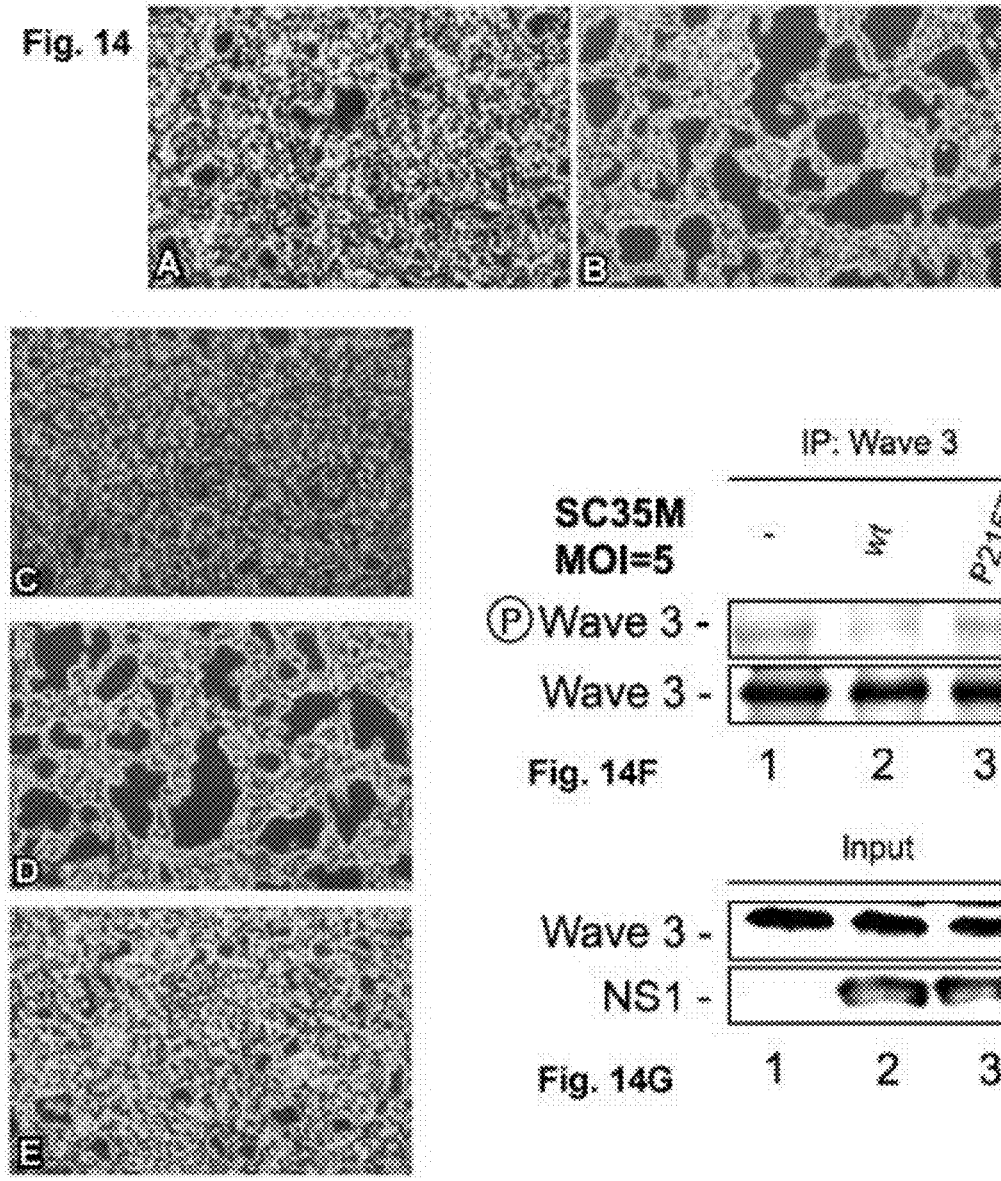

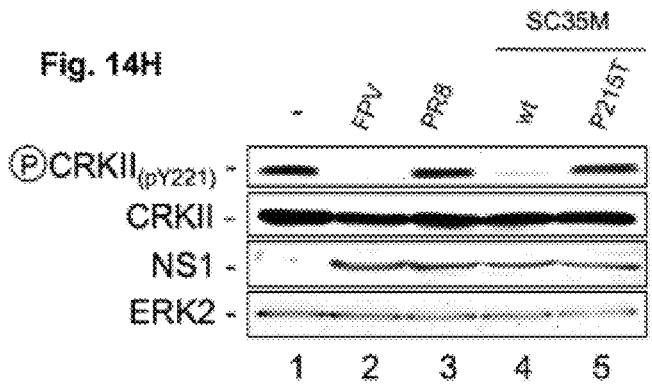

Fig. 14H

| | |
|---|---|
| FPV- Rostock P212S for. | gtaatgagaatgggggaTctccactccctccaaag |
| FPV- Rostock P212S rev. | ctttggagggagtggagAtcccccattctcattac |
| FPV- Rostock P215T for. | atggggqacctccactcActccaaagcagaaacgg |
| FPV- Rostock P215T rev. | ccgtttctgctttggagTgagtggaggtcccccat |
| SC35M P215T forward | atgggagacctccactcactccaaagcagaaacgg |
| SC35M P215T reverse | CCGTTTCTGCTTTGGAGTGAGTGGAGGTCTCCCAT |
| Thailand KAN-1 L207P forw. | atgaggatgggagacctccactccctccaaa |
| Thailand KAN-1 L207P rev. | TTTGGAGGGAGTGGAGGTCTCCCATCCTCAT |
| Thailand KAN-1 N212K for. | tcactccctccaaaacagaaacggaaaatg |
| Thailand KAN-1 N212K rev. | CATTTTCCGTTTCTGTTTTGGAGGGAGTGGA |
| PR8 T215P forward | gggagacctccactccctccaaaacagaaac |
| PR8 T215P reverse | GTTTCTGT

SEQUENCE LISTING

```
<160> NUMBER OF SEQ ID NOS: 107

<210> SEQ ID NO 1
<211> LENGTH: 37
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be any naturally occurring amino acid
```

```
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (26)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid

<400> SEQUENCE: 1

Tyr Leu Thr Asp Met Thr Leu Xaa Xaa Met Ser Xaa Xaa Trp Xaa Met
1               5                   10                  15

Leu Xaa Pro Lys Gln Lys Xaa Xaa Gly Xaa Xaa Xaa Xaa Arg Xaa Asp
            20                  25                  30

Gln Xaa Ile Met Asp
        35

<210> SEQ ID NO 2
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (2)
<223> OTHER INFORMATION: Xaa can be any naturally occurring amino acid
<220> FEATURE:
<221> NAME/KEY: misc_feature
<222> LOCATION: (3)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (5)
<223> OTHER INFORMATION: Xaa can be any naturally occurring amino acid
<220> FEATURE:
<221> NAME/KEY: misc_feature
<222> LOCATION: (6)
<223> OTHER INFORMATION: Xaa can be any of Asn, Arg, Gln, His, Lys, Ser,
      Thr, and Tyr

<400> SEQUENCE: 2

Pro Xaa Xaa Pro Xaa Xaa
1               5

<210> SEQ ID NO 3
<211> LENGTH: 37
<212> TYPE: PRT
<213> ORGANISM: Artificial sequence
<220> FEATURE:
<223> OTHER INFORMATION: synthetic peptide
<220> FEATURE:
```

```
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (23)..(23)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid

<400> SEQUENCE: 3

Tyr Leu Thr Asp Met Thr Leu Xaa Xaa Met Ser Arg Asx Trp Xaa Met
1               5                   10                  15

Leu Xaa Pro Lys Gln Lys Xaa Xaa Gly Xaa Leu Cys Ile Arg Met Asp
            20                  25                  30

Gln Xaa Ile Met Asp
        35

<210> SEQ ID NO 4
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be any of Ala, Asp, Cys, Glu, gly, Ile,
      Leu, Met, Phe, Pro, Trp, and Val
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (23)..(23)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
```

<400> SEQUENCE: 4

Tyr Leu Thr Asp Met Thr Leu Xaa Xaa Met Ser Arg Asx Trp Xaa Met
1               5                   10                  15

Leu Xaa Pro Lys Gln Lys Xaa Xaa Gly Xaa Leu Cys Ile Arg Met Asp
            20                  25                  30

Gln Xaa Ile Met Asp
        35

<210> SEQ ID NO 5
<211> LENGTH: 6
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (6)..(6)
<223> OTHER INFORMATION: Xaa can be Lys or Asn

<400> SEQUENCE: 5

Pro Pro Leu Pro Pro Xaa
1               5

<210> SEQ ID NO 6
<211> LENGTH: 6
<212> TYPE: PRT
<213> ORGANISM: Artificial sequence
<220> FEATURE:
<223> OTHER INFORMATION: synthetic peptide

<400> SEQUENCE: 6

Pro Pro Leu Pro Pro Lys
1               5

<210> SEQ ID NO 7
<211> LENGTH: 6
<212> TYPE: PRT
<213> ORGANISM: Artificial sequence
<220> FEATURE:
<223> OTHER INFORMATION: synthetic peptide

<400> SEQUENCE: 7

Pro Pro Leu Pro Pro Asn
1               5

<210> SEQ ID NO 8
<211> LENGTH: 126
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:

```
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (97)..(98)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (112)..(113)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid
```

<400> SEQUENCE: 8

Met Asp Xaa Asn Thr Xaa Ser Ser Phe Gln Val Asp Cys Phe Leu Trp
1               5                   10                  15

His Val Arg Lys Xaa Xaa Ala Asp Xaa Lys Glu Leu Xaa Asp Ala Pro
            20                  25                  30

Phe Xaa Asp Arg Leu Arg Arg Xaa Gln Lys Ser Leu Arg Gly Arg Gly
        35                  40                  45

Ser Thr Leu Gly Leu Xaa Ile Xaa Xaa Ala Thr Xaa Ala Gly Lys Xaa
    50                  55                  60

Ile Val Xaa Xaa Ile Leu Xaa Xaa Glu Ser Asp Glu Xaa Leu Lys Met
65                  70                  75                  80

Thr Met Xaa Ser Xaa Pro Ala Ser Xaa Tyr Leu Thr Asp Met Thr Leu
            85                  90                  95

Xaa Xaa Met Ser Arg Xaa Trp Xaa Met Leu Xaa Pro Lys Gln Lys Xaa
            100                 105                 110

Xaa Gly Xaa Leu Cys Ile Arg Met Asp Gln Xaa Ile Met Asp
        115                 120                 125

<210> SEQ ID NO 9
<211> LENGTH: 126
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:

```
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (97)..(98)
<223> OTHER INFORMATION: Xaa can be any of Ala, Asp, Cys, Glu, Gly, Ile,
      Leu, Met, Phe, Pro, Trp, and Val
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (112)..(113)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid

<400> SEQUENCE: 9

Met Asp Xaa Asn Thr Xaa Ser Ser Phe Gln Val Asp Cys Phe Leu Trp
1               5                   10                  15

His Val Arg Lys Xaa Xaa Ala Asp Xaa Lys Glu Leu Xaa Asp Ala Pro
            20                  25                  30

Phe Xaa Asp Arg Leu Arg Arg Xaa Gln Lys Ser Leu Arg Gly Arg Gly
        35                  40                  45

Ser Thr Leu Gly Leu Xaa Ile Xaa Xaa Ala Thr Xaa Ala Gly Lys Xaa
50                  55                  60

Ile Val Xaa Xaa Ile Leu Xaa Xaa Glu Ser Asp Glu Xaa Leu Lys Met
65                  70                  75                  80

Thr Met Xaa Ser Xaa Pro Ala Ser Xaa Tyr Leu Thr Asp Met Thr Leu
                85                  90                  95

Xaa Xaa Met Ser Arg Xaa Trp Xaa Met Leu Xaa Pro Lys Gln Lys Xaa
            100                 105                 110

Xaa Gly Xaa Leu Cys Ile Arg Met Asp Gln Xaa Ile Met Asp
        115                 120                 125
```

```
<210> SEQ ID NO 10
<211> LENGTH: 126
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (25)..(25)
<223> OTHER INFORMATION: Xaa can be Gln or Lys
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (40)..(40)
<223> OTHER INFORMATION: Xaa can be any of Asp, Asn, Gln and Glu
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
```

```
<221> NAME/KEY: misc_feature
<222> LOCATION: (97)..(98)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any of Ala, Cys, Ile, Leu, Met, Phe,
      Pro, Trp, and Val
<220> FEATURE:
<221> NAME/KEY: misc_feature
<222> LOCATION: (112)..(112)
<223> OTHER INFORMATION: Xaa can be any of Ala, Cys, Ile, Leu, Met, Phe,
      Pro, Trp, and Val
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid

<400> SEQUENCE: 10

Met Asp Xaa Asn Thr Xaa Ser Ser Phe Gln Val Asp Cys Phe Leu Trp
1               5                   10                  15

His Val Arg Lys Xaa Xaa Ala Asp Xaa Lys Glu Leu Xaa Asp Ala Pro
            20                  25                  30

Phe Xaa Asp Arg Leu Arg Arg Xaa Gln Lys Ser Leu Arg Gly Arg Gly
        35                  40                  45

Ser Thr Leu Gly Leu Asx Ile Xaa Xaa Ala Thr Xaa Ala Gly Lys Xaa
    50                  55                  60

Ile Val Xaa Xaa Ile Leu Xaa Xaa Glu Ser Asp Glu Xaa Leu Lys Met
65                  70                  75                  80

Thr Met Xaa Ser Xaa Pro Ala Ser Xaa Tyr Leu Thr Asp Met Thr Leu
            85                  90                  95

Xaa Xaa Met Ser Arg Asx Trp Xaa Met Leu Xaa Pro Lys Gln Lys Xaa
            100                 105                 110

Xaa Gly Xaa Leu Cys Ile Arg Met Asp Gln Xaa Ile Met Asp
            115                 120                 125

<210> SEQ ID NO 11
<211> LENGTH: 37
<212> TYPE: PRT
<213> ORGANISM: Artificial sequence
<220> FEATURE:
<223> OTHER INFORMATION: synthetic peptide

<400> SEQUENCE: 11

Tyr Leu Thr Asp Met Thr Leu Glu Glu Met Ser Arg Asp Trp Ser Met
1               5                   10                  15

Leu Ile Pro Lys Gln Lys Val Ala Gly Pro Leu Cys Ile Arg Met Asp
            20                  25                  30

Gln Ala Ile Met Asp
        35

<210> SEQ ID NO 12
<211> LENGTH: 37
<212> TYPE: PRT
```

```
<213> ORGANISM: Artificial sequence
<220> FEATURE:
<223> OTHER INFORMATION: synthetic peptide
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any of Ile, Val and Met
<220> FEATURE:
<221> NAME/KEY: misc_feature
<222> LOCATION: (23)..(23)
<223> OTHER INFORMATION: Xaa can be any of Ile, Val and Met
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be Ala or Thr

<400> SEQUENCE: 12

Tyr Leu Thr Asp Met Thr Leu Glu Glu Met Ser Arg Asx Trp Xaa Met
1               5                   10                  15

Leu Xaa Pro Lys Gln Lys Xaa Xaa Gly Xaa Leu Cys Ile Arg Met Asp
            20                  25                  30

Gln Xaa Ile Met Asp
        35

<210> SEQ ID NO 13
<211> LENGTH: 126
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any of Ile, Val and Met
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any of Val, Phe and Leu
<220> FEATURE:
<221> NAME/KEY: misc_feature
<222> LOCATION: (25)..(25)
<223> OTHER INFORMATION: Xaa can be Gln or Lys
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any of Val, Phe and Leu
<220> FEATURE:
<221> NAME/KEY: misc_feature
<222> LOCATION: (40)..(40)
<223> OTHER INFORMATION: Xaa can be any of Asp, Asn, Gln and Glu
<220> FEATURE:
```

```
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be Gln or Leu
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be Ala or Thr
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any of Ile, Val and Met
<220> FEATURE:
<221> NAME/KEY: misc_feature
<222> LOCATION: (112)..(112)
<223> OTHER INFORMATION: Xaa can be any of Ile, Val and Met
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be Ala or Thr

<400> SEQUENCE: 13

Met Asp Xaa Asn Thr Xaa Ser Ser Phe Gln Val Asp Cys Phe Leu Trp
1               5                   10                  15

His Val Arg Lys Xaa Xaa Ala Asp Xaa Lys Glu Leu Xaa Asp Ala Pro
            20                  25                  30

Phe Xaa Asp Arg Leu Arg Arg Xaa Gln Lys Ser Leu Arg Gly Arg Gly
        35                  40                  45

Ser Thr Leu Gly Leu Asx Ile Xaa Xaa Ala Thr Xaa Ala Gly Lys Xaa
    50                  55                  60

Ile Val Xaa Xaa Ile Leu Xaa Xaa Glu Ser Asp Glu Xaa Leu Lys Met
65                  70                  75                  80

Thr Met Xaa Ser Xaa Pro Ala Ser Xaa Tyr Leu Thr Asp Met Thr Leu
            85                  90                  95
```

Glu Glu Met Ser Arg Asx Trp Xaa Met Leu Xaa Pro Lys Gln Lys Xaa
            100                 105                 110

Xaa Gly Xaa Leu Cys Ile Arg Met Asp Gln Xaa Ile Met Asp
        115                 120                 125

<210> SEQ ID NO 14
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (26)..(29)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (31)..(31)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (34)..(34)
<223> OTHER INFORMATION: Xaa can be any naturally occurring amino acid

<400> SEQUENCE: 14

Tyr Leu Thr Asp Met Thr Leu Xaa Xaa Met Ser Xaa Xaa Trp Xaa Met
1               5                   10                  15

Leu Xaa Pro Lys Gln Lys Xaa Xaa Gly Xaa Xaa Xaa Xaa Arg Xaa Asp
            20                  25                  30

Gln Xaa Ile Met Asp
        35

<210> SEQ ID NO 15
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

```
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be one of Ala, Asn, Cys, Gln, Ile, Leu,
      Met, Phe, Pro, Ser, Thr, Trp, Tyr, and Val
<220> FEATURE:
<221> NAME/KEY: misc_feature
<222> LOCATION: (29)..(29)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (31)..(31)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (34)..(34)
<223> OTHER INFORMATION: Xaa can be any naturally occurring amino acid

<400> SEQUENCE: 15

Tyr Leu Thr Asp Met Thr Leu Xaa Xaa Met Ser Xaa Xaa Trp Xaa Met
1               5                   10                  15

Leu Xaa Pro Lys Gln Lys Xaa Xaa Gly Xaa Xaa Xaa Xaa Arg Xaa Asp
            20                  25                  30

Gln Xaa Ile Met Asp
        35

<210> SEQ ID NO 16
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
```

<400> SEQUENCE: 16

Tyr Leu Thr Asp Met Thr Leu Xaa Xaa Met Ser Arg Xaa Trp Xaa Met
1               5                   10                  15

Leu Xaa Pro Lys Gln Lys Xaa Xaa Gly Xaa Leu Cys Ile Arg Met Asp
            20                  25                  30

Gln Xaa Ile Met Asp
        35

<210> SEQ ID NO 17
<211> LENGTH: 38
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (27)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid

<400> SEQUENCE: 17

Xaa Tyr Leu Thr Asp Met Thr Leu Xaa Xaa Met Ser Xaa Xaa Trp Xaa
1               5                   10                  15

Met Leu Xaa Pro Lys Gln Lys Xaa Xaa Gly Xaa Xaa Xaa Xaa Arg Xaa
            20                  25                  30

Asp Gln Xaa Ile Met Asp
        35

<210> SEQ ID NO 18
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be any of Ala, Asp, Cys, Glu, Ile, Leu,
      Met, Phe, Pro, Trp, and Val
<220> FEATURE:

```
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be one of Ala, Asn, Cys, Gln, Ile, Leu,
      Met, Phe, Pro, Ser, Thr, Trp, Tyr, and Val
<220> FEATURE:
<221> NAME/KEY: misc_feature
<222> LOCATION: (29)..(29)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (31)..(31)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (34)..(34)
<223> OTHER INFORMATION: Xaa can be any naturally occurring amino acid

<400> SEQUENCE: 18

Tyr Leu Thr Asp Met Thr Leu Xaa Xaa Met Ser Xaa Xaa Trp Xaa Met
1               5                   10                  15

Leu Xaa Pro Lys Gln Lys Xaa Xaa Gly Xaa Xaa Xaa Xaa Arg Xaa Asp
            20                  25                  30

Gln Xaa Ile Met Asp
        35

<210> SEQ ID NO 19
<211> LENGTH: 38
<212> TYPE: PRT
<213> ORGANISM: Artificial sequence
<220> FEATURE:
<223> OTHER INFORMATION: synthetic peptide

<400> SEQUENCE: 19

Arg Tyr Leu Thr Asp Met Thr Leu Glu Glu Met Ser Arg Asp Trp Ser
1               5                   10                  15

Met Leu Ile Pro Lys Gln Lys Val Ala Gly Pro Leu Cys Ile Arg Met
            20                  25                  30

Asp Gln Ala Ile Met Asp
        35

<210> SEQ ID NO 20
<211> LENGTH: 6
<212> TYPE: PRT
<213> ORGANISM: Artificial sequence
```

```
<220> FEATURE:
<223> OTHER INFORMATION: synthetic peptide
<220> FEATURE:
<221> NAME/KEY: misc_feature
<222> LOCATION: (6)..(6)
<223> OTHER INFORMATION: Xaa can be any of Asn, Arg, Gln, His, Lys, Ser,
      Thr, and Tyr

<400> SEQUENCE: 20

Pro Pro Leu Pro Pro Xaa
1               5

<210> SEQ ID NO 21
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be any of Ala, Asp, Cys, Glu, Ile, Leu,
      Met, Phe, Pro, Trp, and Val
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be one of Ala, Asn, Cys, Gln, Ile, Leu,
      Met, Phe, Pro, Ser, Thr, Trp, Tyr, and Val
<220> FEATURE:
<221> NAME/KEY: misc_feature
<222> LOCATION: (29)..(29)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (31)..(31)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (34)..(34)
<223> OTHER INFORMATION: Xaa can be Ala or Thr

<400> SEQUENCE: 21

Tyr Leu Thr Asp Met Thr Leu Xaa Xaa Met Ser Xaa Asx Trp Xaa Met
1               5                   10                  15

Leu Xaa Pro Lys Gln Lys Xaa Xaa Gly Xaa Xaa Xaa Xaa Arg Xaa Asp
            20                  25                  30

Gln Xaa Ile Met Asp
```

-continued

```
<210> SEQ ID NO 22
<211> LENGTH: 126
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
```

```
<222> LOCATION: (97)..(98)
<223> OTHER INFORMATION: Xaa can be any naturally occurring amino acid
<220> FEATURE:
<221> NAME/KEY: misc_feature
<222> LOCATION: (101)..(102)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (112)..(113)
<223> OTHER INFORMATION: Xaa can be any naturally occurring amino acid
<220> FEATURE:
<221> NAME/KEY: misc_feature
<222> LOCATION: (115)..(118)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid

<400> SEQUENCE: 22

Met Asp Xaa Asn Thr Xaa Ser Ser Phe Gln Val Asp Cys Phe Leu Trp
1               5                   10                  15

His Val Arg Lys Xaa Xaa Ala Asp Xaa Lys Glu Leu Xaa Asp Ala Pro
            20                  25                  30

Phe Xaa Asp Arg Leu Arg Arg Xaa Gln Lys Ser Leu Arg Gly Arg Gly
        35                  40                  45

Ser Thr Leu Gly Leu Xaa Ile Xaa Xaa Ala Thr Xaa Ala Gly Lys Xaa
    50                  55                  60

Ile Val Xaa Xaa Ile Leu Xaa Xaa Glu Ser Asp Glu Xaa Leu Lys Met
65                  70                  75                  80

Thr Met Xaa Ser Xaa Pro Ala Ser Xaa Tyr Leu Thr Asp Met Thr Leu
            85                  90                  95

Xaa Xaa Met Ser Xaa Xaa Trp Xaa Met Leu Xaa Pro Lys Gln Lys Xaa
        100                 105                 110

Xaa Gly Xaa Xaa Xaa Xaa Arg Xaa Asp Gln Xaa Ile Met Asp
        115                 120                 125

<210> SEQ ID NO 23
<211> LENGTH: 126
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (25)..(25)
```

```
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (97)..(98)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (115)..(117)
<223> OTHER INFORMATION: Xaa can be any naturally occurring amino acid
<220> FEATURE:
```

<221> NAME/KEY: misc_feature
<222> LOCATION: (118)..(118)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (120)..(120)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid

<400> SEQUENCE: 23

Met Asp Xaa Asn Thr Xaa Ser Ser Phe Gln Val Asp Cys Phe Leu Trp
1               5                   10                  15

His Val Arg Lys Xaa Xaa Ala Asp Xaa Lys Glu Leu Xaa Asp Ala Pro
            20                  25                  30

Phe Xaa Asp Arg Leu Arg Arg Xaa Gln Lys Ser Leu Arg Gly Arg Gly
        35                  40                  45

Ser Thr Leu Gly Leu Xaa Ile Xaa Xaa Ala Thr Xaa Ala Gly Lys Xaa
    50                  55                  60

Ile Val Xaa Xaa Ile Leu Xaa Xaa Glu Ser Asp Glu Xaa Leu Lys Met
65                  70                  75                  80

Thr Met Xaa Ser Xaa Pro Ala Ser Xaa Tyr Leu Thr Asp Met Thr Leu
            85                  90                  95

Xaa Xaa Met Ser Arg Asx Trp Xaa Met Leu Xaa Pro Lys Gln Lys Xaa
            100                 105                 110

Xaa Gly Xaa Xaa Xaa Xaa Arg Xaa Asp Gln Xaa Ile Met Asp
        115                 120                 125

<210> SEQ ID NO 24
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be any of Ala, Asp, Cys, Glu, Ile, Leu,
      Met, Phe, Pro, Trp, and Val
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any of Ile, Val and Met
<220> FEATURE:
<221> NAME/KEY: misc_feature
<222> LOCATION: (23)..(23)
<223> OTHER INFORMATION: Xaa can be any of Ile, Val and Met
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be one of Ala, Asn, Cys, Gln, Ile, Leu,

```
         Met, Phe, Pro, Ser, Thr, Trp, Tyr, and Val
<220> FEATURE:
<221> NAME/KEY: misc_feature
<222> LOCATION: (29)..(29)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (31)..(31)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (34)..(34)
<223> OTHER INFORMATION: Xaa can be Ala or Thr

<400> SEQUENCE: 24

Tyr Leu Thr Asp Met Thr Leu Xaa Xaa Met Ser Xaa Asx Trp Xaa Met
1               5                   10                  15

Leu Xaa Pro Lys Gln Lys Xaa Xaa Gly Xaa Xaa Xaa Xaa Arg Xaa Asp
            20                  25                  30

Gln Xaa Ile Met Asp
        35

<210> SEQ ID NO 25
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be any of Ala, Asp, Cys, Glu, Ile, Leu,
      Met, Phe, Pro, Trp, and Val
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any of Ile, Val and Met
<220> FEATURE:
<221> NAME/KEY: misc_feature
<222> LOCATION: (23)..(23)
<223> OTHER INFORMATION: Xaa can be any of Ile, Val and Met
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be one of Ala, Asn, Cys, Gln, Ile, Leu,
      Met, Phe, Pro, Ser, Thr, Trp, Tyr, and Val
<220> FEATURE:
<221> NAME/KEY: misc_feature
<222> LOCATION: (29)..(29)
<223> OTHER INFORMATION: Xaa can be any of Cys, Leu, Met and Val
<220> FEATURE:
<221> NAME/KEY: misc_feature
<222> LOCATION: (31)..(31)
<223> OTHER INFORMATION: Xaa can be any of Ile, Met and Val
<220> FEATURE:
<221> NAME/KEY: misc_feature
<222> LOCATION: (34)..(34)
```

<223> OTHER INFORMATION: Xaa can be Ala or Thr

<400> SEQUENCE: 25

Tyr Leu Thr Asp Met Th

```
<210> SEQ ID NO 27
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any of Ile, Val and Met
<220> FEATURE:
<221> NAME/KEY: misc_feature
<222> LOCATION: (23)..(23)
<223> OTHER INFORMATION: Xaa can be any of Ile, Val and Met
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be one of Ala, Asn, Cys, Gln, Ile, Leu,
      Met, Phe, Pro, Ser, Thr, Trp, Tyr, and Val
<220> FEATURE:
<221> NAME/KEY: misc_feature
<222> LOCATION: (29)..(29)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (34)..(34)
<223> OTHER INFORMATION: Xaa can be Ala or Thr

<400> SEQUENCE: 27

Tyr Leu Thr Asp Met Thr Leu Glu Glu Met Ser Xaa Asx Trp Xaa Met
1               5                   10                  15

Leu Xaa Pro Lys Gln Lys Xaa Xaa Gly Xaa Xaa Xaa Xaa Arg Met Asp
            20                  25                  30

Gln Xaa Ile Met Asp
        35

<210> SEQ ID NO 28
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be any of Ala, Asp, Cys, Glu, Ile, Leu,
      Met, Phe, Pro, Trp, and Val
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
```

```
<221> NAME/KEY: misc_feature
<222> LOCATION: (18)..(18)
<223> OTHER INFORMATION: Xaa can be any of Ile, Val and Met
<220> FEATURE:
<221> NAME/KEY: misc_feature
<222> LOCATION: (23)..(23)
<223> OTHER INFORMATION: Xaa can be any of Ile, Val and Met
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be one of Ala, Asn, Cys, Gln, Ile, Leu,
     Met, Phe, Pro, Ser, Thr, Trp, Tyr, and Val
<220> FEATURE:
<221> NAME/KEY: misc_feature
<222> LOCATION: (29)..(29)
<223> OTHER INFORMATION: Xaa can be any of Ala, Cys, Gly, Ile, Leu, Met,
     Phe, Pro, Trp, and Val
<220> FEATURE:
<221> NAME/KEY: misc_feature
<222> LOCATION: (31)..(31)
<223> OTHER INFORMATION: Xaa can be any naturally occurring amino acid

<400> SEQUENCE: 28

Tyr Leu Thr Asp Met Thr Leu Xaa Xaa Met Ser Xaa Asp Trp Xaa Met
1               5                   10                  15

Leu Xaa Pro Lys Gln Lys Xaa Xaa Gly Xaa Xaa Xaa Xaa Arg Xaa Asp
            20                  25                  30

Gln Ala Ile Met Asp
        35

<210> SEQ ID NO 29
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any of Ile, Val and Met
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be one of Ala, Asn, Cys, Gln, Ile, Leu,
     Met, Phe, Pro, Ser, Thr, Trp, Tyr, and Val
<220> FEATURE:
<221> NAME/KEY: misc_feature
```

```
<222> LOCATION: (29)..(29)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (34)..(34)
<223> OTHER INFORMATION: Xaa can be Ala or Thr

<400> SEQUENCE: 29

Tyr Leu Thr Asp Met Thr Leu Glu Glu Met Ser Xaa Asx Trp Xaa Met
1               5                   10                  15

Leu Xaa Pro Lys Gln Lys Xaa Xaa Gly Xaa Xaa Xaa Xaa Arg Met Asp
            20                  25                  30

Gln Xaa Ile Met Asp
        35

<210> SEQ ID NO 30
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any of Ile, Val and Met
<220> FEATURE:
<221> NAME/KEY: misc_feature
<222> LOCATION: (23)..(23)
<223> OTHER INFORMATION: Xaa can be any of Ile, Val and Met
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be Ala or Thr

<400> SEQUENCE: 30

Tyr Leu Thr Asp Met Thr Leu Glu Glu Met Ser Arg Asx Trp Xaa Met
1               5                   10                  15

Leu Xaa Pro Lys Gln Lys Xaa Xaa Gly Xaa Leu Cys Ile Arg Met Asp
            20                  25                  30

Gln Xaa Ile Met Asp
        35

<210> SEQ ID NO 31
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be any of Ala, Asp, Cys, Glu, Ile, Leu,
      Met, Phe, Pro, Trp, and Val
<220> FEATURE:
<221> NAME/KEY: misc_feature
<222> LOCATION: (12)..(12)
<223> OTHER INFORMATION: Xaa can be any naturally occurring amino acid
<220> FEATURE:
```

```
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any of Ile, Val and Met
<220> FEATURE:
<221> NAME/KEY: misc_feature
<222> LOCATION: (23)..(23)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be Ala or Thr

<400> SEQUENCE: 31

Tyr Leu Thr Asp Met Thr Leu Xaa Xaa Met Ser Xaa Asx Trp Xaa Met
1               5                   10                  15

Leu Xaa Pro Lys Gln Lys Xaa Xaa Gly Xaa Xaa Cys Ile Arg Met Asp
            20                  25                  30

Gln Xaa Ile Met Asp
        35

<210> SEQ ID NO 32
<211> LENGTH: 126
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (25)..(25)
<223> OTHER INFORMATION: Xaa can be Gln or Lys
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (40)..(40)
<223> OTHER INFORMATION: Xaa can be any of Asp, Asn, Gln and Glu
<220> FEATURE:
```

```
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (97)..(98)
<223> OTHER INFORMATION: Xaa can be any of Ala, Asp, Cys, Glu, Ile, Leu,
      Met, Phe, Pro, Trp, and Val
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (112)..(112)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid

<400> SEQUENCE: 32

Met Asp Xaa Asn Thr Xaa Ser Ser Phe Gln Val Asp Cys Phe Leu Trp
1               5                   10                  15

His Val Arg Lys Xaa Xaa Ala Asp Xaa Lys Glu Leu Xaa Asp Ala Pro
            20                  25                  30

Phe Xaa Asp Arg Leu Arg Arg Xaa Gln Lys Ser Leu Arg Gly Arg Gly
        35                  40                  45

Ser Thr Leu Gly Leu Asx Ile Xaa Xaa Ala Thr Xaa Ala Gly Lys Xaa
```

```
                  50                  55                  60
Ile Val Xaa Xaa Ile Leu Xaa Xaa Glu Ser Asp Glu Xaa Leu Lys Met
 65                  70                  75                  80

Thr Met Xaa Ser Xaa Pro Ala Ser Xaa Tyr Leu Thr Asp Met Thr Leu
                 85                  90                  95

Xaa Xaa Met Ser Arg Asx Trp Xaa Met Leu Xaa Pro Lys Gln Lys Xaa
            100                 105                 110

Xaa Gly Xaa Leu Cys Ile Arg Met Asp Gln Xaa Ile Met Asp
        115                 120                 125

<210> SEQ ID NO 33
<211> LENGTH: 116
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (15)..(15)
<223> OTHER INFORMATION: Xaa can be Gln or Lys
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (30)..(30)
<223> OTHER INFORMATION: Xaa can be any of Asp, Asn, Gln and Glu
<220> FEATURE:
<221> NAME/KEY: misc_feature
<222> LOCATION: (46)..(47)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (57)..(58)
<223> OTHER INFORMATION: Xaa can be any naturally occurring amino acid
<220> FEATURE:
<221> NAME/KEY: misc_feature
<222> LOCATION: (61)..(62)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
```

```
<220> FEATURE:
<221> NAME/KEY: misc_feature
<222> LOCATION: (79)..(79)
<223> OTHER INFORMATION: Xaa can be any naturally occurring amino acid
<220> FEAT

```
            35                  40                  45
Thr Leu Gly Leu Asp Ile Glu Thr Ala Thr Arg Ala Gly Lys Gln Ile
 50                  55                  60

Val Glu Arg Ile Leu Lys Glu Ser Asp Glu Ala Leu Lys Met Thr
 65                  70                  75                  80

Ile Ala Ser Val Pro Ala Ser Arg Tyr Leu Thr Asp Met Thr Leu Glu
                 85                  90                  95

Glu Met Ser Arg Asp Trp Phe Met Leu Met Pro Lys Gln Lys Val Ala
                100                 105                 110

Gly Ser Leu Cys Ile Arg Met Asp Gln Ala Ile Met Asp Lys Asn Ile
                115                 120                 125

Ile Leu Lys Ala Asn Phe Ser Val Ile Phe Asp Arg Leu Glu Thr Leu
130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Asp Glu Asp Val Lys Asn
                165                 170                 175

Ala Val Gly Val Leu Ile Gly Gly Leu Glu Trp Asn Asp Asn Thr Val
                180                 185                 190

Arg Val Ser Glu Thr Leu Gln Arg Phe Ala Trp Arg Ser Ser Asn Glu
                195                 200                 205

Asn Gly Arg Pro Pro Leu Pro Pro Lys Gln Lys Arg Lys Met Ala Arg
210                 215                 220

Thr Ile Lys Ser Glu Val
225                 230

<210> SEQ ID NO 35
<211> LENGTH: 230
<212> TYPE: PRT
<213> ORGANISM: Influenza A virus
<220> FEATURE:
<223> OTHER INFORMATION: strain A/Hong Kong/481/97(H5N1)

<400> SEQUENCE: 35

Met Asp Ser Asn Thr Val Ser Ser Phe Gln Val Asp Cys Phe Leu Trp
 1               5                  10                  15

His Val Arg Lys Arg Phe Ala Asp Gln Glu Leu Gly Asp Ala Pro Phe
                20                  25                  30

Leu Asp Arg Leu Arg Arg Asp Gln Lys Ser Leu Arg Gly Arg Ser Ser
                35                  40                  45

Thr Leu Gly Leu Asp Ile Arg Thr Ala Thr Arg Glu Gly Lys His Ile
 50                  55                  60

Val Glu Arg Ile Leu Glu Glu Ser Asp Glu Ala Leu Lys Met Thr
 65                  70                  75                  80

Ile Ala Ser Val Pro Ala Ser Arg Tyr Leu Thr Glu Met Thr Leu Glu
                 85                  90                  95

Glu Met Ser Arg Asp Trp Leu Met Leu Ile Pro Lys Gln Lys Val Thr
                100                 105                 110

Gly Ser Leu Cys Ile Arg Met Asp Gln Ala Ile Met Gly Lys Asn Ile
                115                 120                 125

Ile Leu Lys Ala Asn Phe Ser Val Ile Phe Asn Arg Leu Glu Ala Leu
130                 135                 140

Ile Leu Leu Arg Ala Phe Thr Asp Glu Gly Ala Ile Val Gly Glu Ile
145                 150                 155                 160

Ser Pro Leu Pro Ser Leu Pro Gly His Thr Asp Glu Asp Val Lys Asn
```

-continued

```
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Thr Trp Arg Ser Ser Asp Glu
        195                 200                 205

Asn Gly Arg Pro Pro Leu Pro Pro Lys Gln Lys Arg Lys Val Glu Arg
    210                 215                 220

Thr Ile Glu Pro Glu Val
225                 230

<210> SEQ ID NO 36
<211> LENGTH: 230
<212> TYPE: PRT
<213> ORGANISM: Influenza A virus
<220> FEATURE:
<223> OTHER INFORMATION: strain A/Hong Kong/481/97(H5N1)

<400> SEQUENCE: 36

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Ser Ser
        35                  40                  45

Thr Leu Gly Leu Asp Ile Arg Thr Ala Thr Arg Glu Gly Lys His Ile
    50                  55                  60

Val Glu Arg Ile Leu Glu Glu Ser Asp Glu Ala Leu Lys Met Thr
65                  70                  75                  80

Ile Ala Ser Val Pro Ala Ser Arg Tyr Leu Thr Glu Met Thr Leu Glu
                85                  90                  95

Glu Met Ser Arg Asp Trp Leu Met Leu Ile Pro Lys Gln Lys Val Thr
            100                 105                 110

Gly Ser Leu Cys Ile Arg Met Asp Gln Ala Ile Met Gly Lys Asn Ile
        115                 120                 125

Ile Leu Lys Ala Asn Phe Ser Val Ile Phe Asn Arg Leu Glu Ala Leu
    130                 135                 140

Ile Leu Leu Arg Ala Phe Thr Asp Glu Gly Ala Ile Val Gly Glu Ile
145                 150                 155                 160

Ser Pro Leu Pro Ser Leu Pro Gly His Thr Glu Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Thr Trp Arg Ser Ser Asp Glu
        195                 200                 205

Asn Gly Arg Pro Pro Leu Pro Pro Lys Gln Lys Arg Lys Met Glu Arg
    210                 215                 220

Thr Ile Glu Pro Glu Val
225                 230

<210> SEQ ID NO 37
<211> LENGTH: 230
<212> TYPE: PRT
<213> ORGANISM: Influenza A virus
<220> FEATURE:
<223> OTHER INFORMATION: strain A/Canada/rv504/2004(H7N3)

<400> SEQUENCE: 37
```

```
Met Asp Ser Asn Thr Val Ser Ser Phe Gln Val Asp Cys Phe Leu Trp
1               5                  10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Glu Glu Ser Asp Glu Ala Leu Lys Met Thr
65                  70                  75                  80

Ile Ala Ser Val Pro Ala Ser Arg Tyr Leu Thr Asp Met Thr Leu Glu
                85                  90                  95

Glu Met Ser Arg Asp Trp Phe Met Leu Met Pro Lys Gln Lys Val Ala
            100                 105                 110

Gly Ser Leu Cys Ile Arg Met Asp Gln Ala Ile Met Asn Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Ile Gly Glu Ile
145                 150                 155                 160

Ser Pro Leu Pro Ser Leu Pro Gly His Thr Asp Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asp Gly Arg Pro Pro Leu Pro Pro Lys Gln Lys Arg Lys Met Ala Arg
    210                 215                 220

Thr Ile Glu Ser Glu Val
225                 230

<210> SEQ ID NO 38
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be Ala or Glu
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (23)..(23)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
```

<220> FEATURE:
<221> NAME/KEY: misc_feature
<222> LOCATION: (34)..(34)
<223> OTHER INFORMATION: Xaa can be any naturally occurring amino acid

<400> SEQUENCE: 38

Tyr Leu Thr Asp Met Thr Leu Xaa Xaa Met Ser Arg Asx Trp Xaa Met
1               5                   10                  15

Leu Xaa Pro Lys Gln Lys Xaa Xaa Gly Xaa Leu Cys Ile Arg Met Asp
            20                  25                  30

Gln Xaa Ile Met Asp
        35

<210> SEQ ID NO 39
<211> LENGTH: 126
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:

<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (97)..(98)
<223> OTHER INFORMATION: Xaa can be Ala or Glu
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (112)..(113)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid

<400> SEQUENCE: 39

Met Asp Xaa Asn Thr Xaa Ser Ser Phe Gln Val Asp Cys Phe Leu Trp
1               5                   10                  15

His Val Arg Lys Xaa Xaa Ala Asp Xaa Lys Glu Leu Xaa Asp Ala Pro
            20                  25                  30

Phe Xaa Asp Arg Leu Arg Arg Xaa Gln Lys Ser Leu Arg Gly Arg Gly
        35                  40                  45

Ser Thr Leu Gly Leu Xaa Ile Xaa Xaa Ala Thr Xaa Ala Gly Lys Xaa
50                  55                  60

Ile Val Xaa Xaa Ile Leu Xaa Xaa Glu Ser Asp Glu Xaa Leu Lys Met
65                  70                  75                  80

Thr Met Xaa Ser Xaa Pro Ala Ser Xaa Tyr Leu Thr Asp Met Thr Leu
            85                  90                  95

Xaa Xaa Met Ser Arg Xaa Trp Xaa Met Leu Xaa Pro Lys Gln Lys Xaa
        100                 105                 110

Xaa Gly Xaa Leu Cys Ile Arg Met Asp Gln Xaa Ile Met Asp
    115                 120                 125

<210> SEQ ID NO 40
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be Ala or Glu
<220> FEATURE:
<221> NAME/KEY: misc_feature

```
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be one of Ala, Asn, Cys, Gln, Ile, Leu,
      Met, Phe, Pro, Ser, Thr, Trp, Tyr, and Val
<220> FEATURE:
<221> NAME/KEY: misc_feature
<222> LOCATION: (29)..(29)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (31)..(31)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (34)..(34)
<223> OTHER INFORMATION: Xaa can be any naturally occurring amino acid

<400> SEQUENCE: 40

Tyr Leu Thr Asp Met Thr Leu Xaa Xaa Met Ser Xaa Xaa Trp Xaa Met
1               5                   10                  15

Leu Xaa Pro Lys Gln Lys Xaa Xaa Gly Xaa Xaa Xaa Xaa Arg Xaa Asp
            20                  25                  30

Gln Xaa Ile Met Asp
        35

<210> SEQ ID NO 41
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be Ala or Glu
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
```

```
<222> LOCATION: (23)..(23)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be one of Ala, Asn, Cys, Gln, Ile, Leu,
      Met, Phe, Pro, Ser, Thr, Trp, Tyr, and Val
<220> FEATURE:
<221> NAME/KEY: misc_feature
<222> LOCATION: (29)..(29)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (31)..(31)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (34)..(34)
<223> OTHER INFORMATION: Xaa can be Ala or Thr

<400> SEQUENCE: 41

Tyr Leu Thr Asp Met Thr Leu Xaa Xaa Met Ser Xaa Asx Trp Xaa Met
1               5                   10                  15

Leu Xaa Pro Lys Gln Lys Xaa Xaa Gly Xaa Xaa Xaa Xaa Arg Xaa Asp
            20                  25                  30

Gln Xaa Ile Met Asp
        35

<210> SEQ ID NO 42
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be Ala or Glu
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any of Ile, Val and Met
<220> FEATURE:
<221> NAME/KEY: misc_feature
<222> LOCATION: (23)..(23)
<223> OTHER INFORMATION: Xaa can be any of Ile, Val and Met
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
```

```
<222> LOCATION: (28)..(28)
<223> OTHER INFORMATION: Xaa can be one of Ala, Asn, Cys, Gln, Ile, Leu,
      Met, Phe, Pro, Ser, Thr, Trp, Tyr, and Val
<220> FEATURE:
<221> NAME/KEY: misc_feature
<222> LOCATION: (29)..(29)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (31)..(31)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (34)..(34)
<223> OTHER INFORMATION: Xaa can be Ala or Thr

<400> SEQUENCE: 42

Tyr Leu Thr Asp Met Thr Leu Xaa Xaa Met Ser Xaa Asx Trp Xaa Met
1               5                   10                  15

Leu Xaa Pro Lys Gln Lys Xaa Xaa Gly Xaa Xaa Xaa Xaa Arg Xaa Asp
            20                  25                  30

Gln Xaa Ile Met Asp
        35

<210> SEQ ID NO 43
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be Ala or Glu
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any of Ile, Val and Met
<220> FEATURE:
<221> NAME/KEY: misc_feature
<222> LOCATION: (23)..(23)
<223> OTHER INFORMATION: Xaa can be any of Ile, Val and Met
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be one of Ala, Asn, Cys, Gln, Ile, Leu,
      Met, Phe, Pro, Ser, Thr, Trp, Tyr, and Val
<220> FEATURE:
<221> NAME/KEY: misc_feature
<222> LOCATION: (29)..(29)
<223> OTHER INFORMATION: Xaa can be any of Cys, Leu, Met and Val
<220> FEATURE:
<221> NAME/KEY: misc_feature
<222> LOCATION: (31)..(31)
<223> OTHER INFORMATION: Xaa can be any of Ile, Met and Val
<220> FEATURE:
<221> NAME/KEY: misc_feature
```

```
<222> LOCATION: (34)..(34)
<223> OTHER INFORMATION: Xaa can be Ala or Thr

<400> SEQUENCE: 43

Tyr Leu Thr Asp Met Thr Leu Xaa Xaa Met Ser Xaa Asx Trp Xaa Met
1               5                   10                  15

Leu Xaa Pro Lys Gln Lys Xaa Xaa Gly Xaa Xaa Xaa Xaa Arg Xaa Asp
            20                  25                  30

Gln Xaa Ile Met Asp
        35

<210> SEQ ID NO 44
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be Ala or Glu
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any of Ile, Val and Met
<220> FEATURE:
<221> NAME/KEY: misc_feature
<222> LOCATION: (23)..(23)
<223> OTHER INFORMATION: Xaa can be any of Ile, Val and Met
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be one of Ala, Asn, Cys, Gln, Ile, Leu,
      Met, Phe, Pro, Ser, Thr, Trp, Tyr, and Val
<220> FEATURE:
<221> NAME/KEY: misc_feature
<222> LOCATION: (29)..(29)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (31)..(31)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (34)..(34)
<223> OTHER INFORMATION: Xaa can be Ala or Thr

<400> SEQUENCE: 44

Tyr Leu Thr Asp Met Thr Leu Xaa Xaa Met Ser Xaa Asx Trp Xaa Met
1               5                   10                  15

Leu Xaa Pro Lys Gln Lys Xaa Xaa Gly Xaa Xaa Xaa Xaa Arg Xaa Asp
            20                  25                  30

Gln Xaa Ile Met Asp
        35
```

<210> SEQ ID NO 45
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be Ala or Glu
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any of Ile, Val and Met
<220> FEATURE:
<221> NAME/KEY: misc_feature
<222> LOCATION: (23)..(23)
<223> OTHER INFORMATION: Xaa can be any of Ile, Val and Met
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be one of Ala, Asn, Cys, Gln, Ile, Leu,
      Met, Phe, Pro, Ser, Thr, Trp, Tyr, and Val
<220> FEATURE:
<221> NAME/KEY: misc_feature
<222> LOCATION: (29)..(29)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (31)..(31)
<223> OTHER INFORMATION: Xaa can be any naturally occurring amino acid

<400> SEQUENCE: 45

Tyr Leu Thr Asp Met Thr Leu Xaa Xaa Met Ser Xaa Asp Trp Xaa Met
1               5                   10                  15

Leu Xaa Pro Lys Gln Lys Xaa Xaa Gly Xaa Xaa Xaa Xaa Arg Xaa Asp
            20                  25                  30

Gln Ala Ile Met Asp
        35

<210> SEQ ID NO 46
<211> LENGTH: 37
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (8)..(9)
<223> OTHER INFORMATION: Xaa can be Ala or Glu
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature

```
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any of Ile, Val and Met
<220> FEATURE:
<221> NAME/KEY: misc_feature
<222> LOCATION: (23)..(23)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be Ala or Thr

<400> SEQUENCE: 46

Tyr Leu Thr Asp Met Thr Leu Xaa Xaa Met Ser Xaa Asx Trp Xaa Met
1               5                   10                  15

Leu Xaa Pro Lys Gln Lys Xaa Xaa Gly Xaa Xaa Cys Ile Arg Met Asp
            20                  25                  30

Gln Xaa Ile Met Asp
        35

<210> SEQ ID NO 47
<211> LENGTH: 126
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (25)..(25)
<223> OTHER INFORMATION: Xaa can be Gln or Lys
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (40)..(40)
<223> OTHER INFORMATION: Xaa can be any of Asp, Asn, Gln and Glu
<220> FEATURE:
<221> NAME/KEY: misc_feature
```

```
<222> LOCATION: (56)..(57)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (97)..(98)
<223> OTHER INFORMATION: Xaa can be Ala or Glu
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (112)..(112)
<223> OTHER INFORMATION: Xaa can be any of Ala, Cys, Gly, Ile, Leu, Met,
      Phe, Pro, Trp, and Val
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid

<400> SEQUENCE: 47

Met Asp Xaa Asn Thr Xaa Ser Ser Phe Gln Val Asp Cys Phe Leu Trp
1               5                   10                  15

His Val Arg Lys Xaa Xaa Ala Asp Xaa Lys Glu Leu Xaa Asp Ala Pro
            20                  25                  30

Phe Xaa Asp Arg Leu Arg Arg Xaa Gln Lys Ser Leu Arg Gly Arg Gly
        35                  40                  45

Ser Thr Leu Gly Leu Asx Ile Xaa Xaa Ala Thr Xaa Ala Gly Lys Xaa
    50                  55                  60
```

```
Ile Val Xaa Xaa Ile Leu Xaa Xaa Glu Ser Asp Glu Xaa Leu Lys Met
 65                 70                  75                  80

Thr Met Xaa Ser Xaa Pro Ala Ser Xaa Tyr Leu Thr Asp Met Thr Leu
                 85                  90                  95

Xaa Xaa Met Ser Arg Asx Trp Xaa Met Leu Xaa Pro Lys Gln Lys Xaa
            100                 105                 110

Xaa Gly Xaa Leu Cys Ile Arg Met Asp Gln Xaa Ile Met Asp
            115                 120                 125
```

<210> SEQ ID NO 48
<211> LENGTH: 20
<212> TYPE: DNA
<213> ORGANISM: artificial sequence
<220> FEATURE:
<223> OTHER INFORMATION: primer

<400> SEQUENCE: 48
gcaaatttcc atggcaccgt              20

<210> SEQ ID NO 49
<211> LENGTH: 20
<212> TYPE: DNA
<213> ORGANISM: artificial sequence
<220> FEATURE:
<223> OTHER INFORMATION: primer

<400> SEQUENCE: 49
gccccacttg attttggagg              20

<210> SEQ ID NO 50
<211> LENGTH: 26
<212> TYPE: DNA
<213> ORGANISM: artificial sequence
<220> FEATURE:
<223> OTHER INFORMATION: primer

<400> SEQUENCE: 50
ggccatgacc aacaagtgtc tcctcc              26

<210> SEQ ID NO 51
<211> LENGTH: 25
<212> TYPE: DNA
<213> ORGANISM: artificial sequence
<220> FEATURE:
<223> OTHER INFORMATION: primer

<400> SEQUENCE: 51
gcgctcagtt tcggaggtaa cctgt              25

<210> SEQ ID NO 52
<211> LENGTH: 35
<212> TYPE: DNA
<213> ORGANISM: artificial sequence
<220> FEATURE:
<223> OTHER INFORMATION: primer

<400> SEQUENCE: 52
gtaatgagaa tgggggatct ccactccctc caaag              35

<210> SEQ ID NO 53
<211> LENGTH: 35
<212> TYPE: DNA
<213> ORGANISM: artificial sequence
<220> FEATURE:
<223> OTHER INFORMATION: primer

```
<400> SEQUENCE: 53
ctttggaggg agtggagatc ccccattctc attac                              35

<210> SEQ ID NO 54
<211> LENGTH: 35
<212> TYPE: DNA
<213> ORGANISM: artificial sequence
<220> FEATURE:
<223> OTHER INFORMATION: primer

<400> SEQUENCE: 54 atggggggacc tccactcact ccaaagcaga aacgg                             35

<210> SEQ ID NO 55
<211> LENGTH: 35
<212> TYPE: DNA
<213> ORGANISM: artificial sequence
<220> FEATURE:
<223> OTHER INFORMATION: primer

<400> SEQUENCE: 55
ccgtttctgc tttggagtga gtggaggtcc cccat                              35

<210> SEQ ID NO 56
<211> LENGTH: 35
<212> TYPE: DNA
<213> ORGANISM: artificial sequence
<220> FEATURE:
<223> OTHER INFORMATION: primer

<400> SEQUENCE: 56
atgggagacc tccactcact ccaaagcaga aacgg                              35

<210> SEQ ID NO 57
<211> LENGTH: 35
<212> TYPE: DNA
<213> ORGANISM: artificial sequence
<220> FEATURE:
<223> OTHER INFORMATION: primer

<400> SEQUENCE: 57
ccgtttctgc tttggagtga gtggaggtct cccat                              35

<210> SEQ ID NO 58
<211> LENGTH: 31
<212> TYPE: DNA
<213> ORGANISM: artificial sequence
<220> FEATURE:
<223> OTHER INFORMATION: primer

<400> SEQUENCE: 58
atgaggatgg gagacctcca ctccctccaa a                                  31

<210> SEQ ID NO 59
<211> LENGTH: 31
<212> TYPE: DNA
<213> ORGANISM: artificial sequence
<220> FEATURE:
<223> OTHER INFORMATION: primer

<400> SEQUENCE: 59
tttggaggga gtggaggtct cccatcctca t                                  31

<210> SEQ ID NO 60
```

```
<211> LENGTH: 31
<212> TYPE: DNA
<213> ORGANISM: artificial sequence
<220> FEATURE:
<223> OTHER INFORMATION: primer
<400> SEQUENCE: 60
tccactccct ccaaaacaga aacggaaaat g 31

<210> SEQ ID NO 61
<211> LENGTH: 31
<212> TYPE: DNA
<213> ORGANISM: artificial sequence
<220> FEATURE:
<223> OTHER INFORMATION: primer
<400> SEQUENCE: 61
cattttccgt ttctgttttg gagggagtgg a 31

<210> SEQ ID NO 62
<211> LENGTH: 31
<212> TYPE: DNA
<213> ORGANISM: artificial sequence
<220> FEATURE:
<223> OTHER INFORMATION: primer
<400> SEQUENCE: 62
gggagacctc cactccctcc aaaacagaaa c 31

<210> SEQ ID NO 63
<211> LENGTH: 31
<212> TYPE: DNA
<213> ORGANISM: artificial sequence
<220> FEATURE:
<223> OTHER INFORMATION: primer
<400> SEQUENCE: 63
gtttctgttt tggagggagt ggaggtctcc c 31

<210> SEQ ID NO 64
<211> LENGTH: 10
<212> TYPE: PRT
<213> ORGANISM: Influenza A virus
<220> FEATURE:
<223> OTHER INFORMATION: H2N2 virus A/Leningrad/134/47/ts+18/1957

<400> SEQUENCE: 64

Arg Tyr Leu Thr Asp Met Thr Ile Glu Glu
1 5 10

<210> SEQ ID NO 65
<211> LENGTH: 5
<212> TYPE: PRT
<213> ORGANISM: Influenza A virus
<220> FEATURE:
<223> OTHER INFORMATION: H9N2 virus A/chicken/Korea/A146/2009

<400> SEQUENCE: 65

Met Leu Met Pro Lys
1 5

<210> SEQ ID NO 66
<211> LENGTH: 5
<212> TYPE: PRT
<213> ORGANISM: Influenza A virus
<220> FEATURE:
<223> OTHER INFORMATION: H3N2 virus A/X-31

-continued

<400> SEQUENCE: 66

Glu Glu Leu Ser Arg
1               5

<210> SEQ ID NO 67
<211> LENGTH: 5
<212> TYPE: PRT
<213> ORGANISM: Influenza A virus
<220> FEATURE:
<223> OTHER INFORMATION: H1N1 virus A/reassortant/NYMCX-211(NYMC X-157 x
      St. Petersburg/100/2011)

<400> SEQUENCE: 67

Arg Tyr Ile Thr Asp
1               5

<210> SEQ ID NO 68
<211> LENGTH: 6
<212> TYPE: PRT
<213> ORGANISM: Influenza A virus
<220> FEATURE:
<223> OTHER INFORMATION: H1N1 virus A/swine/Hong Kong/NS1680/2001

<400> SEQUENCE: 68

Leu Ile Pro Arg Gln Lys
1               5

<210> SEQ ID NO 69
<211> LENGTH: 10
<212> TYPE: PRT
<213> ORGANISM: Influenza A virus
<220> FEATURE:
<223> OTHER INFORMATION: H1N1 virus A/Memphis/2/1983 and
      A/Niigata/08F031/2009

<400> SEQUENCE: 69

Val Ala Gly Pro Leu Cys Val Arg Met Asp
1               5                   10

<210> SEQ ID NO 70
<211> LENGTH: 6
<212> TYPE: PRT
<213> ORGANISM: Influenza A virus
<220> FEATURE:
<223> OTHER INFORMATION: H1N1 virus A/Cameron/1946

<400> SEQUENCE: 70

Asp Gln Ala Val Met Asp
1               5

<210> SEQ ID NO 71
<211> LENGTH: 7
<212> TYPE: PRT
<213> ORGANISM: Influenza A virus
<220> FEATURE:
<223> OTHER INFORMATION: H5N1 strain A/chicken/Sichuan/81/2005

<400> SEQUENCE: 71

Leu Cys Ile Lys Met Asp Gln
1               5

<210> SEQ ID NO 72
<211> LENGTH: 10
<212> TYPE: PRT
<213> ORGANISM: Influenza A virus
<220> FEATURE:

```
<223> OTHER INFORMATION: H5N1 strain A/chicken/Sichuan/81/2005

<400> SEQUENCE: 72

Leu Ser Arg Asp Trp Ser Met Leu Ile Pro
1               5                   10

<210> SEQ ID NO 73
<211> LENGTH: 10
<212> TYPE: PRT
<213> ORGANISM: Influenza A virus
<220> FEATURE:
<223> OTHER INFORMATION: H5N1 virus A/reassortant/NIBRG-14(Viet
      Nam/1194/2004 x Puerto Rico/8/1934)

<400> SEQUENCE: 73

Met Ser Arg Glu Trp Ser Met Leu Ile Pro
1               5                   10

<210> SEQ ID NO 74
<211> LENGTH: 20
<212> TYPE: PRT
<213> ORGANISM: Influenza A virus
<220> FEATURE:
<223> OTHER INFORMATION: H1N1 virus strain A/United Kingdom/1-MA/1933

<400> SEQUENCE: 74

Arg His Leu Thr Asp Met Thr Leu Glu Glu Met Ser Arg His Trp Phe
1               5                   10                  15

Met Leu Met Pro
            20

<210> SEQ ID NO 75
<211> LENGTH: 20
<212> TYPE: PRT
<213> ORGANISM: Influenza A virus
<220> FEATURE:
<223> OTHER INFORMATION: H1N1 virus strain A/WS/1933

<400> SEQUENCE: 75

Arg Tyr Leu Thr Asp Met Thr Leu Glu Glu Met Ser Arg His Trp Phe
1               5                   10                  15

Met Leu Met Pro
            20

<210> SEQ ID NO 76
<211> LENGTH: 20
<212> TYPE: PRT
<213> ORGANISM: Influenza A virus
<220> FEATURE:
<223> OTHER INFORMATION: H1N1 virus strain A/Phila/1935

<400> SEQUENCE: 76

Arg Tyr Leu Thr Asp Met Thr Leu Glu Glu Met Ser Arg Asp Trp Phe
1               5                   10                  15

Met Leu Arg Pro
            20

<210> SEQ ID NO 77
<211> LENGTH: 10
<212> TYPE: PRT
<213> ORGANISM: Influenza A virus
<220> FEATURE:
<223> OTHER INFORMATION: H7N3 virus strain
      A/Chicken/Rawalpindi/NARC68/2002

<400> SEQUENCE: 77
```

```
Met Ser Arg Asp Trp Phe Met Leu Met Pro
1               5                   10

<210> SEQ ID NO 78
<211> LENGTH: 10
<212> TYPE: PRT
<213> ORGANISM: Influenza A virus
<220> FEATURE:
<223> OTHER INFORMATION: H1N1 virus strain A/Puerto
      Rico/8-CIP045_RG89697/1934

<400> SEQUENCE: 78

Arg Tyr Leu Thr Asp Met Thr Leu Ala Ala
1               5                   10

<210> SEQ ID NO 79
<211> LENGTH: 20
<212> TYPE: PRT
<213> ORGANISM: Influenza A virus
<220> FEATURE:
<223> OTHER INFORMATION: H4N4 virus strain
      A/mallard/Washington/44242-271/2006

<400> SEQUENCE: 79

Met Ser Arg Asp Trp Phe Met Leu Met Pro Lys Gln Lys Val Ala Gly
1               5                   10                  15

Ser Leu Cys Ile
            20

<210> SEQ ID NO 80
<211> LENGTH: 20
<212> TYPE: PRT
<213> ORGANISM: Influenza A virus
<220> FEATURE:
<223> OTHER INFORMATION: H1N1 virus strain A/Memphis/2/1983

<400> SEQUENCE: 80

Met Ser Arg Asp Trp Phe Met Leu Met Pro Lys Gln Lys Val Ala Gly
1               5                   10                  15

Pro Leu Cys Val
            20

<210> SEQ ID NO 81
<211> LENGTH: 20
<212> TYPE: PRT
<213> ORGANISM: Influenza A virus
<220> FEATURE:
<223> OTHER INFORMATION: H5N1 virus strain A/duck/Shantou/1930/2001

<400> SEQUENCE: 81

Met Ser Arg Asp Trp Phe Met Leu Met Pro Lys Gln Lys Val Ala Gly
1               5                   10                  15

Pro Leu Cys Ile
            20

<210> SEQ ID NO 82
<211> LENGTH: 30
<212> TYPE: PRT
<213> ORGANISM: Influenza A virus
<220> FEATURE:
<223> OTHER INFORMATION: H1N1 virus strain A/swine/Hong Kong/NS1680/2001

<400> SEQUENCE: 82

Arg Tyr Leu Ala Asp Met Thr Leu Glu Glu Met Ser Arg Asp Trp Phe
1               5                   10                  15
```

```
Met Leu Ile Pro Arg Gln Lys Ile Ile Gly Ser Leu Cys Val
            20                  25                  30

<210> SEQ ID NO 83
<211> LENGTH: 8
<212> TYPE: PRT
<213> ORGANISM: Influenza A virus
<220> FEATURE:
<223> OTHER INFORMATION: H1N1 virus strain A/Memphis/2/1983

<400> SEQUENCE: 83

Val Ala Gly Pro Pro Cys Ile Arg
1               5

<210> SEQ ID NO 84
<211> LENGTH: 20
<212> TYPE: PRT
<213> ORGANISM: Influenza A virus
<220> FEATURE:
<223> OTHER INFORMATION: H5N1 virus strain
      A/chicken/Thailand/Udonthani-01/2004

<400> SEQUENCE: 84

Met Ser Gly Asp Trp Phe Met Leu Met Pro Lys Gln Lys Val Ala Gly
1               5                   10                  15

Ser Leu Cys Ile
            20

<210> SEQ ID NO 85
<211> LENGTH: 10
<212> TYPE: PRT
<213> ORGANISM: Influenza A virus
<220> FEATURE:
<223> OTHER INFORMATION: H6N1 virus strain A/chicken/Taiwan/0305/04

<400> SEQUENCE: 85

Lys Gln Lys Val Ala Gly Ser Leu Leu Ile
1               5                   10

<210> SEQ ID NO 86
<211> LENGTH: 13
<212> TYPE: PRT
<213> ORGANISM: Influenza A virus
<220> FEATURE:
<223> OTHER INFORMATION: H6N2 virus strain A/duck/Fujian/1695/2005

<400> SEQUENCE: 86

Lys Gln Lys Val Ala Gly Pro Leu Phe Ile Lys Met Asp
1               5                   10

<210> SEQ ID NO 87
<211> LENGTH: 15
<212> TYPE: PRT
<213> ORGANISM: Influenza A virus
<220> FEATURE:
<223> OTHER INFORMATION: H3N2 virus strain A/Bilthoven/628/1976

<400> SEQUENCE: 87

Lys Gln Lys Val Glu Gly Pro Leu Cys Ile Arg Ile Asp Gln Ala
1               5                   10                  15

<210> SEQ ID NO 88
<211> LENGTH: 7
<212> TYPE: PRT
<213> ORGANISM: Influenza A virus
<220> FEATURE:
```

```
<223> OTHER INFORMATION: H5N1 virus strain A/chicken/Hunan/1/2009

<400> SEQUENCE: 88

Gly Pro Leu Met Phe Lys Met
1               5

<210> SEQ ID NO 89
<211> LENGTH: 6
<212> TYPE: PRT
<213> ORGANISM: Influenza A virus
<220> FEATURE:
<223> OTHER INFORMATION: H9N2 virus strain A/duck/Shantou/3577/2003

<400> SEQUENCE: 89

Arg Asp Trp Ile Met Leu
1               5

<210> SEQ ID NO 90
<211> LENGTH: 5
<212> TYPE: PRT
<213> ORGANISM: Influenza A virus
<220> FEATURE:
<223> OTHER INFORMATION: H9N2 virus strain A/duck/Beijing/MG0617/2005

<400> SEQUENCE: 90

Arg Asp Trp Leu Met
1               5

<210> SEQ ID NO 91
<211> LENGTH: 6
<212> TYPE: PRT
<213> ORGANISM: Influenza A virus
<220> FEATURE:
<223> OTHER INFORMATION: strain A/duck/Korea/GJ74/2007(H3N1)

<400> SEQUENCE: 91

Pro Ser Leu Pro Pro Lys
1               5

<210> SEQ ID NO 92
<211> LENGTH: 6
<212> TYPE: PRT
<213> ORGANISM: Influenza A virus
<220> FEATURE:
<223> OTHER INFORMATION: strain A/duck/Korea/GJ108/2007(H3N2)

<400> SEQUENCE: 92

Pro Ser Leu Pro Pro Asn
1               5

<210> SEQ ID NO 93
<211> LENGTH: 6
<212> TYPE: PRT
<213> ORGANISM: Influenza A virus
<220> FEATURE:
<223> OTHER INFORMATION: A/Philippines/344/2004(H1N2)

<400> SEQUENCE: 93

Pro Pro Phe Pro Pro Lys
1               5

<210> SEQ ID NO 94
<211> LENGTH: 6
<212> TYPE: PRT
<213> ORGANISM: Influenza A virus
<220> FEATURE:
<223> OTHER INFORMATION: strain A/chicken/West Java/Smi-Biot/2008(H5N1)
```

<400> SEQUENCE: 94

Pro Pro Phe Pro Pro Asn
1               5

<210> SEQ ID NO 95
<211> LENGTH: 6
<212> TYPE: PRT
<213> ORGANISM: Influenza A virus
<220> FEATURE:
<223> OTHER INFORMATION: strain A/African
      starling/England-Q/983/1979(H7N1)

<400> SEQUENCE: 95

Pro Ser Phe Pro Pro Lys
1               5

<210> SEQ ID NO 96
<211> LENGTH: 6
<212> TYPE: PRT
<213> ORGANISM: Influenza A virus
<220> FEATURE:
<223> OTHER INFORMATION: strain A/swine/Italy/259543/2003(H1N2)

<400> SEQUENCE: 96

Pro Pro Phe Pro Thr Lys
1               5

<210> SEQ ID NO 97
<211> LENGTH: 6
<212> TYPE: PRT
<213> ORGANISM: Influenza A virus
<220> FEATURE:
<223> OTHER INFORMATION: strain A/swine/Italy/526/1985(H3N2)

<400> SEQUENCE: 97

Pro Pro Phe Pro Ser Lys
1               5

<210> SEQ ID NO 98
<211> LENGTH: 6
<212> TYPE: PRT
<213> ORGANISM: Influenza A virus
<220> FEATURE:
<223> OTHER INFORMATION: strain A/mallard/Mississippi/360/2010(H3N8)

<400> SEQUENCE: 98

Pro Pro Phe Pro Ala Lys
1               5

<210> SEQ ID NO 99
<211> LENGTH: 6
<212> TYPE: PRT
<213> ORGANISM: Influenza A virus
<220> FEATURE:
<223> OTHER INFORMATION: strain A/equine/Tennessee/5/1986(H3N8)

<400> SEQUENCE: 99

Pro Ser Phe Pro Pro Lys
1               5

<210> SEQ ID NO 100
<211> LENGTH: 6
<212> TYPE: PRT
<213> ORGANISM: Influenza A virus
<220> FEATURE:
<223> OTHER INFORMATION: strain A/canine/Colorado/17864/2006(H3N8)

```
<400> SEQUENCE: 100

Pro Ser Phe Pro Ser Lys
1               5

<210> SEQ ID NO 101
<211> LENGTH: 6
<212> TYPE: PRT
<213> ORGANISM: Influenza A virus
<220> FEATURE:
<223> OTHER INFORMATION: strain A/goose/Yunnan/4129/2005(H5N1)

<400> SEQUENCE: 101

Pro Pro Leu Pro Ser Asn
1               5

<210> SEQ ID NO 102
<211> LENGTH: 6
<212> TYPE: PRT
<213> ORGANISM: Influenza A virus
<220> FEATURE:
<223> OTHER INFORMATION: strain A/duck/Vietnam/OIE-1234/2012(H3N2)

<400> SEQUENCE: 102

Pro Pro Leu Pro Thr Lys
1               5

<210> SEQ ID NO 103
<211> LENGTH: 6
<212> TYPE: PRT
<213> ORGANISM: Influenza A virus
<220> FEATURE:
<223> OTHER INFORMATION: strain A/chicken/Taiwan/0706/03(H6N1)

<400> SEQUENCE: 103

Pro Pro Leu Pro Ser Lys
1               5

<210> SEQ ID NO 104
<211> LENGTH: 6
<212> TYPE: PRT
<213> ORGANISM: Influenza A virus
<220> FEATURE:
<223> OTHER INFORMATION: strain A/red-necked
      stint/Australia/5745/1981(H12N9)

<400> SEQUENCE: 104

Pro Pro Leu Pro Ala Lys
1               5

<210> SEQ ID NO 105
<211> LENGTH: 6
<212> TYPE: PRT
<213> ORGANISM: Influenza A virus
<220> FEATURE:
<223> OTHER INFORMATION: PR8 (H1N1)

<400> SEQUENCE: 105

Pro Pro Leu Thr Pro Lys
1               5

<210> SEQ ID NO 106
<211> LENGTH: 6
<212> TYPE: PRT
<213> ORGANISM: Influenza A virus
<220> FEATURE:
<223> OTHER INFORMATION: KAN-1 (H5N1)
```

```
<400> SEQUENCE: 106

Leu Pro Leu Pro Pro Asn
1               5

<210> SEQ ID NO 107
<211> LENGTH: 6
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: Xaa can be any of Ala, Cys, Gly, Ile, Leu, Met,
      Phe, Pro, Trp, and Val
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be Lys or Arg

<400> SEQUENCE: 107

Pro Pro Xaa Pro Xaa Xaa
1               5
```

METHODS AND PEPTIDES FOR PREVENTING AND TREATING A BCR-ABL AND A C-ABL ASSOCIATED DISEASE

CROSS-REFERENCE TO RELATED APPLICATIONS

This application is the U.S. national phase application filed under 35 U.S.C. §371 claiming benefit to International Patent Application No. PCT/EP2013/068032, filed on Aug. 30, 2013, which is entitled to priority under 35 U.S.C. §119(a)-(d) to European application no. EP 12 182 644, filed on Aug. 31, 2012, the disclosures of which are incorporated herein by reference in their entirety.

BACKGROUND OF THE INVENTION

The leukaemia forms chronic myeloid leukaemia (or chronic myelogenous leukaemia; CML), acute lymphatic leukaemia (ALL) and acute myeloic leukaemia (AML) have been characterized as diseases that at least in part are caused by a reciprocal translocation between chromosomes 9 and 22, which cytogenetically results in the Philadelphia chromosome (Ph) and molecularly gives rise to the chimeric BCR-ABL1 gene. More than 95% of patients suffering from CML, which is characterized by increased and unregulated proliferation of predominantly myeloid cells in the bone marrow, have been tested positively for this translocation chromosome (Guinn, B. A., et al., Cancer Immunology (2007), CII 56, 943-957). CML occurs most commonly in the middle-aged and elderly and accounts for 15-20% of all cases of adult leukaemia in Western populations. The BCR-ABL1 transcript, encoding a fusion oncoprotein, is present in approximately 25% of patients with B-cell acute lymphoblastic leukaemia (B-ALL).

CML has been found to be caused by the presence of the Ph chromosome in hematopoietic stem cells. Expression of BCR-ABL in hematopoietic cells induces resistance to apoptosis, growth factor independence, and leukomogenesis. While the parent tyrosine kinase c-Abl shuttles between locations at the plasma membrane, actin cytoskeleton, the cytosol and the nucleus, the fusion protein is found only in the cytoplasm and is constitutively active. The tyrosine kinase activity of the fusion protein activates a complex signaling network. It inter alia leads to phosphorylation of Bad as well as constitutive activation of Stat5, thereby enhancing cell survival.

Clinically, the disease can be subdivides into three distinct phases: chronic, accelerated, and blast. Most patients are present in the chronic phase, a stage that is typically indolent in nature. Mature granulocytes are found, but patients typically have an increase in the number of myeloid progenitor cells found in the blood. Left untreated, the disease progresses to the accelerated phase, followed by blast crisis, which is inevitably fatal. During blast phase, hematopoietic differentiation is blocked and blast cells accumulate in the bone marrow and peripheral blood.

Imatinib, a 2-phenylaminopyrimidine derivative, binds to the activation loop of ABL kinase outside of a highly conserved ATP binding site, which traps the kinase in an inactive conformation. Although highly effective, imatinib does not eradicate the disease. Even in patients who demonstrate good response after treatment with a BCR-ABL inhibitor, minimal residual disease is detected at the molecular level using polymerase chain reaction (PCR). Further, a significant minority of patients with newly diagnosed CML in the chronic phase respond poorly to imatinib and are regarded as showing primary resistance. Other patients respond well initially and then lose their response; they may be classified as showing secondary resistance.

In addition, any response observed in patients in the more advanced stages of CML, i.e. accelerated and blastic phases, have been found to typically be short-lived. Further, patients treated with imatinib may eventually develop resistance, particularly those treated in the accelerated or blastic phases. Finally, imatinib treatment has been linked to the potential development of cardiotoxicity in patients with CML.

Currently, a number of further compounds with activity against the BCR-ABL protein kinase are being tested, some of which inhibit the kinase activity of BCR-ABL through mechanisms of action other than interference with the ATP binding site of the kinase. The second-generation BCR-ABL inhibitors nilotinib, a phenylaminopyrimidine derivative, and dasatinib have shown significant activity after imatinib failure, however, particularly in case of dasatinib, associated with untoward off-target toxicities, probably due to their inhibitory activity against a broader range of protein kinases than imatinib. There thus remains a need for alternative treatments of diseases associated with the chimeric BCR-ABL protein.

SUMMARY OF THE INVENTION

Provided is a combination of an isolated peptide or peptidomimetic that includes the sequence of SEQ ID NO: 1 or a homolog thereof, and an isolated peptide or peptidomimetic that includes the sequence of SEQ ID NO: 2. Also provided is a method of treating a BCR-ABL associated disease or a c-ABL associated disease in a subject. A method as disclosed herein is based on the use of the aforementioned combination of one or more isolated peptides and/or peptidomimetics.

In a first aspect the present invention provides a combination of a first peptide or peptidomimetic and a second peptide or peptidomimetic. Both the first and the second peptide or peptidomimetic are isolated peptides and/or peptidomimetics. The first and the second peptide or peptidomimetic may optionally be included within a single chain, such as a single peptide chain, a single peptidomimetic chain or a peptide/peptidomimetic hybrid, in the following also referred to as a peptide/peptidomimetic mixture. The first peptide includes the sequence of SEQ ID NO: 1, or a homolog thereof. In some embodiments the first peptide essentially consists of the sequence of SEQ ID NO: 1, or a homolog thereof. In some embodiments the first peptide consists of the sequence of SEQ ID NO: 1, or a homolog thereof. The first peptidomimetic contains a sequence that corresponds to the sequence of SEQ ID NO: 1, or a homolog thereof. In some embodiments the first peptidomimetic essentially consists of a sequence that corresponds to the sequence of SEQ ID NO: 1, or a homolog thereof. In some embodiments the first peptidomimetic consists of a sequence that corresponds to the sequence of SEQ ID NO: 1, or a homolog thereof.

SEQ ID NO: 1 has, in one letter code the following amino acid sequence: YLTDMTLX$_1$X$_1$M SX$_1$X$_1$WX$_1$MLX$_1$PK QKX$_1$X$_1$GX$_1$X$_1$X$_1$X$_1$R X$_1$DQX$_1$IMD (SEQ ID NO: 1). X$_1$ in this sequence represents any amino acid. The first peptidomimetic includes a sequence that corresponds to the sequence of SEQ ID NO: 1, or the homolog thereof. The second peptide includes the sequence of SEQ ID NO: 2, or a homolog thereof. In some embodiments the second peptide essentially consists of the sequence of SEQ ID NO: 2, or a homolog thereof. In some embodiments the second peptide consists of the sequence of SEQ ID NO: 2, or a homolog thereof. SEQ ID NO: 2 has, in one letter code, the amino acid sequence $PX_1X_{13}PX_1X_{10}$. $X_1$ in this sequence represents any amino acid. $X_{10}$ in this sequence, as well as in related sequences, represents a polar amino acid that is neutral or positively charged, such as N, Q, H, K, T or Y. $X_{13}$ in this sequence and in related sequences represents a nonpolar amino acid such as A, V, I, L, M, F, G, P or W. The second peptidomimetic includes a sequence that corresponds to the sequence of SEQ ID NO: 2. In some embodiments the second peptidomimetic essentially consists of a sequence that corresponds to the sequence of SEQ ID NO: 2, or a homolog thereof. In some embodiments the second peptidomimetic consists of a sequence that corresponds to the sequence of SEQ ID NO: 2, or a homolog thereof.

In some embodiments SEQ ID NO: 2 has, in one letter code, the amino acid sequence of SEQ ID NO: 20, which is the following sequence: $PPLPPX_{10}$. $X_{10}$ in this sequence and related sequences represents a polar amino acid that is neutral or positively charged, such as N, Q, H, K, T or Y. The second peptidomimetic includes a sequence that corresponds to the sequence of SEQ ID NO: 2.

In some embodiments SEQ ID NO: 1 has, in one letter code the amino acid sequence of SEQ ID NO: 14, which is the following sequence: $YLTDMTLX_1X_1M$ $SX_1X_1WX_1MLX_1PK$ $QKX_1X_1GX_1X_1X_1X_{13}R$ $X_{13}DQX_1IMD$ (SEQ ID NO: 14). $X_1$ in this sequence, as in all other sequences disclosed in this document, represents any amino acid. $X_{13}$ in this sequence and related sequences represents a nonpolar amino acid such as A, V, I, L, M, F, G, P or W.

In some embodiments SEQ ID NO: 1 has, in one letter code the amino acid sequence of SEQ ID NO: 15, which is the following sequence: $YLTDMTLX_1X_1M$ $SX_1X_1WX_1MLX_1PK$ $QKX_1X_1GX_1X_1X_2X_{13}R$ $X_{13}DQX_1IMD$ (SEQ ID NO: 15). $X_1$ in this sequence and related sequences represents any amino acid. $X_2$ in this sequence and related sequences represents a nonpolar amino acid or a polar uncharged/neutral amino acid. $X_{13}$ in this sequence and related sequences represents a nonpolar amino acid such as A, V, I, L, M, F, G, P or W.

In some embodiments SEQ ID NO: 1 has, in one letter code the following amino acid sequence: $YLTDMTLX_1X_1M$ $SRX_1WX_1MLX_1PK$ $QKX_1X_1GX_1LCIR$ $MDQX_1IMD$ (SEQ ID NO: 16). $X_1$ in this sequence represents any amino acid.

In some embodiments SEQ ID NO: 1 has, in one letter code the following amino acid sequence: $X_1YLTDMTLX_1X_1$ $MSX_1X_1WX_1MLX_1P$ $KQKX_1X_1GX_1X_1X_1X_1$ $RX_1DQX_1IMD$ (SEQ ID NO: 17).

SEQ ID NO: 1 has in some embodiments the amino acid sequence of SEQ ID NO: 18, which is the following sequence: $YLTDMTLX_{12}X_{12}M$ $SX_1X_1WX_1MLX_1PK$ $QKX_{13}X_1G$ $X_1X_1X_2X_{13}R$ $X_{13}DQX_1IMD$ (SEQ ID NO: 18). $X_{12}$ in this sequence and related sequences represents a nonpolar amino acid or a negatively charged amino acid. In some embodiments $X_{12}$ is E or A (SEQ ID NO: 40). As noted above, $X_{13}$ is a nonpolar amino acid.

In some embodiments SEQ ID NO: 1 has the following amino acid sequence: $YLTDMTLX_{12}X_{12}M$ $SX_1X_5WX_1MLX_1PK$ $QKX_{13}X_1GX_1X_1X_2X_{13}R$ $X_{13}DQX_8IMD$ (SEQ ID NO: 21). $X_8$ in this sequence and related sequences represents A or T. $X_{12}$ represents a nonpolar amino acid or a negatively charged amino acid. In some embodiments $X_{12}$ is E or A (SEQ ID NO: 41).

SEQ ID NO: 1 has in some embodiments the following amino acid sequence: $YLTDMTLX_{12}X_{12}M$ $SX_1X_5WX_1MLX_7PK$ $QKX_7X_1GX_1X_1X_2X_{13}R$ $X_{13}DQX_8IMD$ (SEQ ID NO: 24). $X_7$ in this sequence as well as related sequences, represents I, V or M. $X_8$ in this sequence and related sequences represents A or T. $X_{12}$ represents a nonpolar amino acid or a negatively charged amino acid. In some embodiments $X_{12}$ is E or A (SEQ ID NO: 42).

SEQ ID NO: 1 has in some embodiments the following amino acid sequence: $YLTDMTLX_{12}X_{12}M$ $SX_1X_5WX_1MLX_7PK$ $QKX_7X_1GX_1X_1X_2X_{14}R$ $X_{15}DQX_8IMD$ (SEQ ID NO: 25). $X_7$ in this sequence and related sequences represents I, V or M. $X_8$ in this sequence and related sequences represents A or T. $X_{12}$ represents a nonpolar amino acid or a negatively charged amino acid (supra). In some embodiments $X_{12}$ is E or A (SEQ ID NO: 43). $X_{14}$ in this sequence and related sequences represents C, V, M or L. $X_{15}$ in this sequence and related sequences represents V, M or I.

In some embodiments SEQ ID NO: 1 has, in one letter code the following amino acid sequence: $YLTDMTLX_{12}X_{12}M$ $SX_1X_5WX_1MLX_7PK$ $QKX_7X_1GX_1X_1X_2X_{13}R$ $X_{13}DQX_8IMD$ (SEQ ID NO: 26). T. As noted above, $X_{12}$ represents a nonpolar amino acid or a negatively charged amino acid. In some embodiments $X_{12}$ is E or A (SEQ ID NO: 44).

In some embodiments SEQ ID NO: 1 has, in one letter code the following amino acid sequence: $YLTDMTLEEM$ $SX_1X_5WX_1MLX_7PK$ $QKX_7X_1GX_1X_1X_2X_{13}R$ $MDQX_8IMD$ (SEQ ID NO: 27).

SEQ ID NO: 1 has in some embodiments the following amino acid sequence: $YLTDMTLX_{12}X_{12}M$ $SX_1DWX_1MLX_7PK$ $QKX_7X_1GX_1X_1X_2X_{13}R$ $X_1DQAIMD$ (SEQ ID NO: 28). T. $X_{12}$ represents a nonpolar amino acid or a negatively charged amino acid (supra). In some embodiments $X_{12}$ is E or A (SEQ ID NO: 45).

In some embodiments SEQ ID NO: 1 has, in one letter code the following amino acid sequence: $YLTDMTLEEM$ $SX_1X_5WX_1MLX_1PK$ $QKX_7X_1GX_1X_1X_2X_{13}R$ $MDQX_8IMD$ (SEQ ID NO: 29).

SEQ ID NO: 1 has in some embodiments the following amino acid sequence: $YLTDMTLEEM$ $SRX_5WX_1MLX_7PK$ $QKX_7X_1GX_1LCIR$ $MDQX_8IMD$ (SEQ ID NO: 30).

In some embodiments SEQ ID NO: 1 has the amino acid sequence of SEQ ID NO: 31: $YLTDMTLX_{12}X_{12}M$ $SX_1X_5WX_1MLX_7PK$ $QKX_{13}X_1GX_1X_1CIR$ $MDQX_8IMD$ (SEQ ID NO: 31). As noted above, $X_{12}$ represents a nonpolar amino acid or a negatively charged amino acid. In some embodiments $X_{12}$ is E or A (SEQ ID NO: 46).

In some embodiments SEQ ID NO: 1 has, in one letter code the amino acid sequence of SEQ ID NO: 3, which is the following sequence: $YLTDMTLX_1X_1M$ $SRX_5WX_1MLX_{13}PK$ $QKX_{13}X_1GX_1LCIR$ $MDQX_1IMD$ (SEQ ID NO: 3). $X_1$ in this sequence represents any amino acid. $X_{13}$ in this sequence and related sequences represents a nonpolar amino acid. $X_5$ in this sequence and related sequences represents D or N. As indicated above, the first peptide may also include a sequence that is a homolog of SEQ ID NO: 3.

In some embodiments SEQ ID NO: 1 has, in one letter code the amino acid sequence of SEQ ID NO: 4, which is the following sequence: $YLTDMTLX_{12}X_{12}M$ $SRX_5WX_1ML$ $X_{13}PK$ $QKX_{13}X_1GX_1LCIR$ $MDQX_1IMD$ (SEQ ID NO: 4). $X_{12}$ in this sequence and related sequences represents a nonpolar amino acid or a negatively charged amino acid. As indicated above, the first peptide may also include a sequence that is a homolog of SEQ ID NO: 4. In some embodiments of this sequence and related sequences $X_{12}$ is E or A (SEQ ID NO: 38).

In some embodiments SEQ ID NO: 1 has, in one letter code, the amino acid sequence of SEQ ID NO: 12, which is the following sequence: YLTDMTLEEM SRX$_5$WX$_1$MLX$_7$PK QKX$_7$X$_1$GX$_1$LCIR MDQX$_8$IMD (SEQ ID NO: 12). $X_5$ in this sequence and related sequences represents D or N. $X_7$ in this sequence and related sequences represents I, V or M. $X_8$ in this sequence and related sequences represents A or T. As indicated above, the first peptide may also include a sequence that is a homolog of SEQ ID NO: 12.

In some embodiments the first peptide includes the amino acid sequence of SEQ ID NO: 22, which is the following sequence: MDX$_1$NTX$_1$SSFQ VDCFLWHVRK X$_1$X$_1$ADX$_1$ KELX$_1$DA PFX$_1$DRLRRX$_1$Q KSLRGRGSTL GLX$_1$IX$_1$ X$_1$ATX$_1$A GKX$_1$IVX$_1$X$_1$ILX$_1$ X$_1$ESDEX$_1$LKMT MXSX$_1$PASX$_1$YL TDMTLX$_1$X$_1$MSX$_1$ X$_1$WX$_1$ML X$_1$PKQK X$_1$X$_1$GX$_1$ X$_1$X$_1$X$_1$RX$_1$D QX$_1$IMD (SEQ ID NO: 22). $X_1$ in this sequence represents any amino acid. As indicated above, the first peptide may also include a sequence that is a homolog of SEQ ID NO: 22. In some embodiments the first peptide essentially consists of the sequence of SEQ ID NO: 22, or a homolog thereof. In some embodiments the first peptide consists of the sequence of SEQ ID NO: 1, or a homolog thereof.

Any of the above illustrated embodiments of individual amino acids for selected amino acid positions, including groups and/or subgroups of suitable amino acids, such as $X_1$, $X_2$, $X_3$, $X_4$, $X_5$, $X_6$, $X_7$, $X_8$, $X_9$, $X_{11}$, $X_{12}$, $X_{13}$, $X_{14}$ or $X_{15}$ included in any of the above sequences may as such be combined with any other amino acid, group and/or subgroup of suitable amino acids in selected positions shown in other sequences above. The same applies to embodiments of individual amino acids at selected positions, including groups and/or subgroups of suitable amino acids that are shown below, i.e. positions of amino acids or groups/subgroups of amino acids shown as embodiments of SEQ ID NO: 23. Where such amino acids, groups or subgroups of amino acids shown as embodiments of SEQ ID NO: 23 correspond to amino acid positions of SEQ ID NO: 1, these amino acids, groups or subgroups of amino acids can individually be combined with amino acids, groups or subgroups of amino acids shown above in the context of embodiments of SEQ ID NO: 1.

In some embodiments the first peptide includes the amino acid sequence of SEQ ID NO: 23, which is the following sequence: MDX$_1$NTX$_1$SSFQ VDCFLWHVRK X$_1$X$_1$A DX$_1$KELX$_1$DA PFX$_1$DRLRRX$_1$Q KSLRGRGSTL GLX$_1$IX$_1$ X$_1$ATX$_1$A GKX$_1$IVX$_1$X$_1$ILX$_1$ X$_1$ESDEX$_1$LKMT MXSX$_1$PASX$_1$YL TDMTLX$_1$X$_1$MSR X$_5$WX$_1$MLX$_1$PKQK X$_{13}$X$_1$GX$_1$ X$_1$X$_1$X$_{13}$RX$_1$D QX$_1$IMD (SEQ ID NO: 23). $X_1$ in this sequence represents any amino acid. In some embodiments the first peptide essentially consists of the sequence of SEQ ID NO: 23, or a homolog thereof. In some embodiments the first peptide consists of the sequence of SEQ ID NO: 23, or a homolog thereof.

The first peptide includes in some embodiments, in one letter code, the amino acid sequence of SEQ ID NO: 8, which is the following sequence: MDX$_1$NTX$_1$SSFQ VDCFLWHVRK X$_1$X$_1$ADX$_1$KELX$_1$DA PFX$_1$DRLRRX$_1$Q KSLRGRGSTL GLX$_1$IX$_1$ X$_1$ATX$_1$A GKX$_1$IVX$_1$X$_1$ILX$_1$ X$_1$ESDEX$_1$LKMT MXSX$_1$PASX$_1$YL TDMTLX$_1$X$_1$MSR X$_1$WX$_1$MLX$_1$PKQK X$_1$X$_1$GX$_1$LCI RMD QX$_1$IMD (SEQ ID NO: 8). In some embodiments the first peptide essentially consists of the sequence of SEQ ID NO: 8, or a homolog thereof. In some embodiments the first peptide consists of the sequence of SEQ ID NO: 8, or a homolog thereof.

The first peptide includes in some embodiments, in one letter code, the amino acid sequence of SEQ ID NO: 9, which is the following sequence: MDX$_1$NTX$_1$SSFQ VDCFLWHVRK X$_1$X$_1$ADX$_1$KELX$_1$DA PFX$_1$DRLRRX$_1$Q KSLRGRGSTL GLX$_1$IX$_1$ X$_1$ATX$_1$A GKX$_1$IVX$_1$X$_1$ILX$_1$ X$_1$ESDEX$_1$LKMT MXSX$_1$PASX$_1$YL TDMTLX$_{12}$X$_{12}$MSR X$_1$WX$_1$MLX$_1$PKQK X$_1$X$_1$GX$_1$LCI RMD QX$_1$IMD (SEQ ID NO: 9). As defined above, $X_1$ represents any amino acid. $X_{12}$ in this sequence and related sequences represents a nonpolar amino acid or a negatively charged amino acid. In some embodiments $X_{12}$ in this sequence and related sequences is E or A (SEQ ID NO: 39). As indicated above, the first peptide may also include a sequence that is a homolog of SEQ ID NO: 9. In some embodiments the first peptide essentially consists of the sequence of SEQ ID NO: 9, or a homolog thereof. In some embodiments the first peptide consists of the sequence of SEQ ID NO: 9, or a homolog thereof.

In some embodiments SEQ ID NO: 8 has, in one letter code the amino acid sequence of SEQ ID NO: 10, which is the following sequence: MDX$_1$NTX$_{13}$SSFQ VDCFL-WHVRK X$_1$X$_{13}$ADX$_3$KELX$_1$DA PFX$_{13}$DRLRRX$_4$Q KSL-RGRGSTL GLX$_5$IX$_1$X$_1$ATX$_1$A GKX$_1$IVX$_1$ X$_1$ILX$_1$ X$_1$ESDEX$_1$LKMT MXSX$_1$PASX$_1$YL TDMTLX$_1$X$_1$MSR X$_5$WX$_1$MLX$_{13}$PKQK X$_{13}$X$_1$GX$_1$LCIRMD QX$_1$IMD (SEQ ID NO: 10). $X_{13}$ in this sequence and related sequences represents a nonpolar amino acid. $X_3$ in this sequence and related sequences represents Q or K. $X_4$ in this sequence and related sequences represents D, N, Q or E. $X_5$ in this sequence and related sequences represents D or N. As indicated above, the first peptide may also include a sequence that is a homolog of SEQ ID NO: 10.

In some embodiments SEQ ID NO: 8 has, in one letter code the amino acid sequence of SEQ ID NO: 32, which is the following sequence: MDX$_1$NTX$_{13}$SSFQ VDCFL-WHVRK X$_1$X$_{13}$ ADX$_3$KELX$_1$DA PFX$_{13}$DRLRRX$_4$Q KSLRGRGSTL GLX$_5$IX$_1$X$_1$ATX$_1$A GKX$_1$IVX$_1$ X$_1$ILX$_1$ X$_1$ESDEX$_1$LKMT MXSX$_1$PASX$_1$YL TDMTLX$_{12}$X$_{12}$MSR X$_5$WX$_1$MLX$_{13}$PKQK X$_{13}$X$_1$GX$_1$L CIRMD QX$_1$IMD (SEQ ID NO: 32). $X_{13}$ in this sequence and related sequences represents a nonpolar amino acid. $X_3$ in this sequence and related sequences represents Q or K. $X_4$ in this sequence and related sequences represents D, N, Q or E. $X_5$ in this sequence represents D or N. $X_{12}$ in this sequence and related sequences represents a nonpolar amino acid or a negatively charged amino acid. In some embodiments $X_{12}$ in this sequence is E or A (SEQ ID NO: 46). As indicated above, the first peptide may also include a sequence that is a homolog of SEQ ID NO: 32.

In some embodiments SEQ ID NO: 8 has, in one letter code, the amino acid sequence of SEQ ID NO: 13, which is the following sequence: MDX$_1$NTX$_7$SSFQ VDCFL-WHVRK X$_1$X$_9$ADX$_3$K ELX$_1$DA PFX$_9$DRLRRX$_4$Q KSL-RGRGSTL GLX$_5$IX$_1$X$_1$ATX$_1$A GKX$_6$IVX$_1$X$_1$ ILX$_1$ X$_1$ESDEX$_8$LKMT MXSX$_1$PASX$_1$YL TDMTLEEMSR X$_5$WX$_1$MLX$_7$PKQK X$_7$X$_1$GX$_1$ LCIRMD QX$_8$IMD (SEQ ID NO: 13). $X_3$ in this sequence and related sequences represents Q or K. $X_4$ in this sequence and related sequences represents D, N, Q or E. $X_5$ in this sequence represents D or N. $X_6$ in this sequence and related sequences represents Q or L. $X_7$ in this sequence and related sequences represents I, V or M. $X_8$ in this sequence represents A or T. $X_9$ in this sequence and related sequences represents V, F or L. As indicated above, the first peptide may also include a sequence that is a homolog of SEQ ID NO: 13.

In some embodiments the first peptide includes, in one letter code, the amino acid sequence of SEQ ID NO: 33, which is the following sequence: VDCFLWHVRK $X_1X_{13}$ADX$_3$KELX$_1$DA PFX$_{13}$DRLRRX$_4$Q KSLRGRG-STL GLX$_5$IX$_1$X$_1$ATX$_1$A GKX$_1$IVX$_1$ X$_1$ILX$_1$ X$_1$ESDEX$_1$LKMT MXSX$_1$PASX$_1$YL TDMTLX$_1$X$_1$MSR X$_5$WX$_1$MLX$_{13}$PKQK X$_{13}$X$_1$GX$_1$LCIRMD QX$_1$IMD (SEQ ID NO: 33). $X_{13}$, $X_3$, $X_4$ and $X_5$ in this sequence are as defined above. As indicated above, the first peptide may also include a sequence that is a homolog of SEQ ID NO: 33. In some embodiments the first peptide essentially consists of the sequence of SEQ ID NO: 33, or a homolog thereof. In some embodiments the first peptide consists of the sequence of SEQ ID NO: 33, or a homolog thereof.

In some embodiments the second peptide has the sequence of SEQ ID NO: 5, or a homolog thereof. SEQ ID NO: 5 has the sequence PPLPPX$_{11}$. $X_{11}$ in this sequence and related sequences represents K or N. In some embodiments SEQ ID NO: 5 of the second peptide has, in one letter code, the amino acid sequence of SEQ ID NO: 6, which is the sequence PPLPPK. In some embodiments SEQ ID NO: 5 of the second peptide has, in one letter code, the amino acid sequence of SEQ ID NO: 7, which is the sequence PPLPPN. In some embodiments the second peptide contains the sequence of SEQ ID NO: 5, or a homolog thereof. In some embodiments the second peptide essentially consists of the sequence of SEQ ID NO: 5, or a homolog thereof. In some embodiments the second peptide consists of the sequence of SEQ ID NO: 5, or a homolog thereof.

As indicated above the first and the second peptide or peptidomimetic may in some embodiments be included in a common peptide, peptidomimetic or hybrid of a peptide and peptidomimetic. In some embodiments the combination of the first and the second peptide or peptidomimetic is encompassed in a single peptide or peptidomimetic, or a respective peptide/peptidomimetic hybrid.

In a second aspect the invention provides a method of treating a BCR-ABL associated disease or a c-ABL associated disease in a subject. The method includes administering a combination of a peptide that contains the sequence of SEQ ID NO: 1 and a peptide that contains the sequence of SEQ ID NO: 2. As indicated above, the first and the second peptide may in some embodiments be included in a common peptide, peptidomimetic or peptide/peptidomimetic hybrid.

In a third aspect the invention provides a combination of one or more nucleic acid molecules. The one or more nucleic acid molecules include a sequence that encodes a peptide of SEQ ID NO: 1, or a homolog thereof. The one or more nucleic acid molecules also include a sequence encoding a peptide of SEQ ID NO: 2. In some embodiments the one or more nucleic acid molecules are a single nucleic acid molecule that includes a sequence that encodes a peptide of SEQ ID NO: 1, or a homolog thereof, and a sequence encoding a peptide of SEQ ID NO: 2. Typically the encoded peptide is a single peptide that contains both the sequence of SEQ ID NO: 1, or a homolog thereof, and the sequence of SEQ ID NO: 2.

In a fourth aspect the invention provides a method of treating a BCR-ABL associated disease or a c-ABL associated disease in a subject. The method includes administering the combination of one or more nucleic acid molecules according to the third aspect.

In a fourth aspect the invention provides an ex vivo method of identifying a peptide combination, peptidomimetic combination or peptide/peptidomimetic combination that is capable of inhibiting the kinase activity of a BCR-ABL protein and/or a c-ABL protein to a higher extent than a combination of a peptide or peptidomimetic that contains the sequence of SEQ ID NO: 1 and a peptide that contains the sequence of SEQ ID NO: 2. The method typically includes providing a first and a second microorganism. Both the first and the second microorganism are expressing the BCR-ABL protein and/or the c-ABL protein. The method of the fifth aspect includes introducing a first peptide or peptidomimetic combination into the first microorganism. The first microorganism expresses the BCR-ABL protein and/or the c-ABL protein. The first peptide or peptidomimetic combination includes a peptide or peptidomimetic that includes the sequence of SEQ ID NO: 1, or a homolog thereof. The first peptide combination further includes a peptide or peptidomimetic that includes the sequence of SEQ ID NO: 2. The first peptide or peptidomimetic combination also includes a peptide or peptidomimetic that includes an amino acid sequence that is suspected to enhance the inhibition of the kinase activity of the BCR-ABL protein and/or of the c-ABL protein. Further, the method of the fifth aspect includes introducing a second peptide or peptidomimetic combination into the second microorganism. The second microorganism expresses the BCR-ABL protein and/or the c-ABL protein. The second peptide or peptidomimetic combination consists of a peptide that includes the sequence of SEQ ID NO: 1, or a homolog thereof, and a peptide that includes the sequence of SEQ ID NO: 2. The method of the fifth aspect further includes comparing the kinase activity of the BCR-ABL protein and/or the c-ABL protein that is determined in the first microorganism and the kinase activity of the BCR-ABL protein and/or the c-ABL protein that is determined in the second microorganism.

In typical embodiments the method of the fifth aspect includes determining the kinase activity of the BCR-ABL protein and/or the c-ABL protein in the first microorganism. Further, typically the method includes determining the kinase activity of the BCR-ABL protein and/or the c-ABL protein in the second microorganism. In some embodiments the method of the fifth aspect includes monitoring the kinase activity of the BCR-ABL protein and/or the c-ABL protein in the first microorganism. In some embodiments the method of the fifth aspect includes monitoring the kinase activity of the BCR-ABL protein and/or the c-ABL protein in the second microorganism.

In some embodiments of the method of the fifth aspect the first and the second microorganism are of the same cell type and/or of the same species.

In some embodiments of the method of the fifth aspect is a method of identifying a identifying a peptide or peptidomimetic combination that is capable of preventing and/or treating a BCR-ABL associated disease or a c-ABL associated disease in a subject.

In a sixth aspect the invention provides a method of identifying a peptide or peptidomimetic combination that is capable of inhibiting the kinase activity of a BCR-ABL protein and/or a c-ABL protein. The method includes providing a host organism. The host organism encompasses a cancer associated with the presence of a BCR-ABL protein and/or a mutated c-ABL protein. The method includes introducing a peptide or peptidomimetic combination into cells of the host organism. The peptide or peptidomimetic combination includes a peptide or peptidomimetic that includes the sequence of SEQ ID NO: 1, or a homolog thereof. The peptide or peptidomimetic combination further includes a peptide or peptidomimetic that includes the sequence of SEQ ID NO: 2. In some embodiments the peptide combination also includes a further peptide, which includes an amino acid sequence that is suspected to enhance the inhibition of the kinase activity of the BCR-ABL protein and/or of the c-ABL protein. The method further includes monitoring the cancer state of the host organism.

Typically the method according to the sixth aspect is a method of identifying a peptide or peptidomimetic combination that is capable of inhibiting the kinase activity of a BCR-ABL protein and/or a c-ABL protein to a higher extent than a combination of a peptide or peptidomimetic that contains the sequence of SEQ ID NO: 1 and a peptide that contains the sequence of SEQ ID NO: 2. The method typically includes providing a first and a second host organism. Both the first and the second host organism encompass a cancer associated with the presence of a BCR-ABL protein and/or a mutated c-ABL protein. The method includes introducing a peptide or peptidomimetic combination into cells of the first and a second host organism. The method of this embodiment further includes introducing a first peptide or peptidomimetic combination into the first host organism. The first peptide or peptidomimetic combination includes a peptide or peptidomimetic that includes the sequence of SEQ ID NO: 1, or a homolog thereof. The first peptide combination further includes a peptide or peptidomimetic that includes the sequence of SEQ ID NO: 2. The first peptide or peptidomimetic combination also includes a peptide that includes an amino acid sequence that is suspected to enhance the inhibition of the kinase activity of the BCR-ABL protein and/or of the c-ABL protein. Further, the method of this embodiment includes introducing a second peptide or peptidomimetic combination into the second host organism. The second peptide or peptidomimetic combination consists of a peptide or peptidomimetic that includes the sequence of SEQ ID NO: 1, or a homolog thereof, and a peptide or peptidomimetic that includes the sequence of SEQ ID NO: 2. The method of this embodiment further includes comparing the development of the cancer state of the first host organism and of the second host organism.

The summary of the invention described above is non-limiting, and other features and advantages of the invention will be apparent from the following detailed description of the invention, and from the claims.

BRIEF DESCRIPTION OF THE DRAWINGS

FIG. 1 shows the analysis of ATF2- and CRKL-phosphorylation following infection of A549 cells by the influenza virus A/FPV/Rostock/34 rec. and by the influenza virus mutants A/FPV/Rostock/34/NS1-P212S rec./A/FPV/Rostock/34/NS1-P215T rec. A549 cells were infected with the influenza virus A/FPV/Rostock/34 rec. (wt) or with the virus mutants A/FPV/Rostock/34/NS1-P212S rec. and A/FPV/Rostock/34/NS1-P215T rec. 24 hours after seeding (MOI: 1). Uninfected A549 cells were used as a control. 18 hours after infection cells were lysed. Released proteins were separated by SDS-PAGE and transferred to a nitrocellulose membrane. Proteins were detected with an antibody specific to NS1(23-1). CRKL phosphorylation and the amount of eIF4E were analysed by means of the PathScan BCR/ABL Activity Assay commercially available from Cell Signaling. ATF-2 phosphorylation was detected by specific antibody. The usage of equivalent protein amounts was ensured via detection of ATF-2 and CRKL.

FIG. 2 shows that the CRK adaptor protein phosphorylation is strongly reduced upon avian IAV infection.

FIG. 2A: A549 cells were infected with the avian IAV FPV (MOI=5), the human IAV PR8 (MOI=5) for 8 h or left uninfected. Cell lysates were subjected to immunoprecipitation (IP) using an anti-CRKL antibody. A rabbit serum used for IP served as a control. Broad CRKL phosphorylation was detected by Western-Blot (WB) analysis. Equal protein precipitation of CRKL and co-immunoprecipitation of the viral NS1 were verified using specific antibodies. The NS1 protein and endogenous CRKL of crude cell lysates served as a control.

FIG. 2B-2H: A549 cells (B, C, D), MDCK cells (E, F) and 293 cells (G, H) were infected with the avian IAV FPV (MOI=5), the human IAV PR8 (MOI=5) for the indicated times or were left uninfected. Phosphorylated CRKL (pY207; B-H) and phosphorylated CRKII (pY221; C-H) were analysed by Western Blot. Equal protein loads were verified using CRKL (B-H), CRKII (C-H) and ERK2 (B) antibodies. Viral protein synthesis was visualized via NS1 Western Blot (B-H).

FIG. 3: C-Abl kinase activity is impaired upon avian IAV infection. A549 cells were infected with the avian IAV FPV (MOI=5), the human IAV PR8 (MOI=5) or left uninfected. 8 h p.i., cells were harvested and c-Abl was immunoprecipitated using a specific c-Abl antibody. For control a mouse serum was used. After c-Abl immunoprecipitation, an in vitro kinase assay using MBP as substrate was performed. Phosphorylation of the substrate MBP was detected by Western Blot analysis. Equal protein precipitation of c-Abl was verified using a specific antibody (A). The NS1 protein and endogenous c-Abl of crude cell lysates served as a control (C). Band intensities were quantified using ImageJ software and normalized to the uninfected sample (B). Mean band intensities of three independent experiments are depicted and statistical significance of the differences were determined by students t-test (* p<0.05).

FIG. 4: The SH3(II)bm within NS1 is needed for c-Abl kinase inhibition. A-C: A549 cells were infected with the rec. avian IAV SC35M wt or SC35M P215T (MOI=5) for 8 h or left uninfected and subsequently harvested. A: Cell lysates were subjected to immunoprecipitation (IP) using an anti-NS1 antibody. A rabbit serum was used as a control for IP. Co-immunoprecipitation of CRKL and CRKII was analysed by Western-Blot analysis. Equal protein precipitation of NS1 was verified using a specific antibody. The NS1 protein and endogenous CRKL and CRKII of crude cell lysates served as a control. B: Phosphorylated CRKL (pY207) and phosphorylated CRKII (pY221) were analysed by Western-Blot. Equal protein loads were verified using CRKL, CRKII and ERK2 antibodies and viral protein synthesis was visualized via NS1 Western-Blot. C: Harvested cell lysates were subjected to c-Abl immunoprecipitation using a specific c-Abl antibody. For control a mouse serum was used. After c-Abl immunoprecipitation, an in vitro kinase assay was performed and the phosphorylation of the used substrate MBP was analysed by Western Blot. Equal protein precipitation of c-Abl was verified using a specific antibody. The NS1 protein and endogenous c-Abl of crude cell lysates served as a control. Band intensities were quantified using ImageJ software and normalized to the uninfected sample. Mean band intensities of three independent experiments are depicted and statistical significance of the differences were determined by students t-test (* p<0.05).

FIG. 5: H5N1 and a bit human IAV NS1 block c-Abl activity after introduction of the SH3(II)bm. A-D: A549 cells were infected with the rec. H5N1 IAV KAN-1 wt or KAN-1 L207P/N212K (A, B) (MOI=5), the rec. human IAV PR8 wt or PR8 T215P (C, D) (MOI=5) and the avian IAV FPV (D) (MOI=5) for 8 h. Uninfected cells served as a control and cells were treated with 20 µM of the c-Abl inhibitor Imatinib (D). Cell lysates were subjected to immunoprecipitation (IP) with an anti-NS1 antibody (A, C). A rabbit serum was used as a control for IP. Co-immunoprecipitation of CRKL was detected by Western-Blot analysis and equal NS1 protein precipitation was verified using specific antibody. The NS1 protein and endogenous CRKL of crude cell lysates served as a control. Phosphorylated CRKL (pY207) and phosphorylated CRKII (pY221) were detected by Western-Blot analysis (B, D). For loading control, CRKL, CRKII and ERK2 antibodies were used and viral protein synthesis was visualized via NS1 Western Blot.

FIG. 6: NS1 of IAV binds to c-Abl.

FIG. 6A, 6B: 293 cells were transfected with a plasmid expressing the fusion protein GST-c-Abl or an empty vector. 24 h upon transfection, cells were infected with the avian IAV FPV (A) (MOI=5) or the human IAV PR8 (B) (MOI=5) for 8 h or were left uninfected. Cell lysates were harvested and subjected to GST-pull-down assay. Co-precipitation of NS1 was detected by Western Blot analysis and equal GST-c-Abl protein precipitation was verified using a specific GST antibody. The NS1 protein amount and GST-c-Abl protein amount in crude cell lysates served as control.

FIG. 6C-6E: 293 cells were transfected with a plasmid expressing the fusion protein GST-c-Abl or expressing GST alone. Co-transfection with plasmids encoding HA-tagged NS1 (from the human IAV PR8) full-length (aa 1-230) (C) or C-terminal truncated NS1 versions aa 1-125 (D) and aa 1-88 (E) or empty vector (C-E) was conducted. 24 h upon transfection, cells were lysed and cell lysates were used for GST-pull-down assay. Co-precipitation of NS1 was detected by HA-antibody in Western Blot analysis and equal GST-c-Abl protein and GST protein precipitation was verified using a specific GST antibody. The NS1 protein amount, GST-c-Abl protein and GST protein amount in crude cell lysates served as control.

FIG. 9. IAV mediated c-Abl inhibition results in strong cytopathogenic cell alteration upon avian IAV infection. A549 cells were infected with the avian IAV FPV, the human IAV PR8, the rec. avian IAV SC35M wt or SC35M P215T, the rec. H5N1 IAV KAN-1 wt or KAN-1 L207P/N212K and the rec. human IAV PR8 wt or PR8 T215P (MOI=5). Uninfected cells served as control. 8 h p.i. cells were fixed, permeabilized and stained with a primary anti-A/NP antibody targeted by an Alexa Fluor 568 conjugated secondary antibody. Cell nucleus (Dapi staining) and actin cytoskeleton (Alexa Fluor 488 Phalloidin staining) was visualized. Pictures were recorded using the fluorescence microscope Axiovert 200M (Zeiss) (40× objective). Representative images of each sample are depicted. A: uninfected cells; B: FPV; C: PR8; D: SC35M wt; E: SC35M P215T; F: KAN-1 wt; G: KAN-1 L207P N212K; H: PR8 rec. wt; I: PR8 rec. T215P.

FIG. 10 is a table depicting the sequences of the second SH3 binding motif (SH3(II)bm) of different A/NS1 proteins. Amino-acid (aa) sequences of the SH3(II)bm at aa212-217 of A/NS1 proteins of different IAV strains and the class II SH3 binding consensus are depicted. The human IAV consensus is based on 2008-2009 isolates and the avian consensus is based on all avian H1-H4 and H6-H9 isolates. X indicates any amino acid, φ denotes a hydrophobic residue, and + indicates a positively charged amino acid.

FIG. 11. Avian IAV infection blocks c-Abl-CRK interaction, however, altered CRKII expression does not affect c-Abl activity. A: 293 cells were transfected with a GST-c-Abl expression plasmid and 24 h upon transfection, cells were infected with the avian IAV FPV (MOI=5) or the human IAV PR8 (MOI=5) for 8 h or were left uninfected. Cell lysates were harvested and subjected to a GST-pull-down assay. Co-precipitation of CRKII and CRKI was detected by Western Blot analysis. Equal GST-c-Abl protein precipitation was verified using a specific GST antibody. The CRKII, CRKI and GST-c-Abl protein amount in crude cell lysates served as a control.

FIG. 12. Chemical inhibition of c-Abl affects an intermediate to late step in avian IAV life cycle. A549 cells were infected with the avian IAV FPV (A) (MOI=0.01) or the human IAV PR8 (B) (MOI=0.5). Cells were either (i) preincubated for 30 min and postincubated directly upon infection, (ii) solely postincubated directly upon infection or (iii) postincubated 2 h, 4 h or 6 h p.i. with 20 µM Imatinib. Infected, untreated cells served as a control. 8 h p.i. supernatants were collected and analysed for progeny virus yields in standard plaque titrations. The virus titer of the untreated control was set as 100% and the titers are depicted in % of the untreated control. Representative results of at least three independent experiments are depicted.

FIG. 13. C-Abl kinase does not affect polymerase activity, viral protein accumulation and type I IFN induction.

FIG. 13 A: 293 cells were transfected with plasmids expressing the polymerase subunits PB1, PB2, PA and NP of the avian IAV FPV-Rostock together with an antisense luciferase reporter gene flanked by the influenza virus promoters of the M-segment. Cells not expressing PB1 served as a negative control. Directly upon transfection, cells were treated with 20 µM Imatinib or were left untreated. 24 h upon transfection cells were lysed and luciferase activity was measured. Cells not expressing PB1 were set as 1.

FIG. 13 B-D: A549 cells were infected with the avian IAV FPV (B, C), the human IAV PR8 (B and C), the rec. avian IAV SC35M wt and SC35M P215T (B, D) (MOI=5) for 8 h. (B-D) Uninfected cells served as control. (B, C) Directly upon infection cells were treated with 20 µM Imatinib or were left untreated. (B) Cells were lysed and viral protein expression was measured via specific PB1, NS1, NP and M1 antibodies in Western Blot analysis. Detection of ERK2 expression served as control. (C, D) Cells were lysed and total RNA was isolated. IFNβ mRNA amounts were analyzed in qRT-PCR and n-folds of uninfected and untreated cells (C) and uninfected cells (D) are depicted.

FIG. 14. Avian IAV mediated c-Abl inhibition, linked to cell morphology alterations, affects actin cytoskeletal regulators. 293 cells were infected with the avian IAV FPV (B), the human IAV PR8 (C), the rec. avian IAV SC35M wt (D, F, G) and SC35M P215T (E, F, G) (MOI=5). Uninfected cells (A, F, G) served as control. FIG. 14A-E, H: 6 h p.i., cells were photographed (10× objective) (A-E) and afterwards lysed. Phosphorylated CRKII (pY221) was detected in Western Blot analysis. Protein levels of NS1 served as infection control and detection of CRKII and ERK2 served as loading control (H). FIG. 14F, G: 8 h p.i. cells were lysed and subjected to Wave 3 immunoprecipitation with an anti-Wave 3 antibody. Broad Wave 3 phosphorylation and equal protein precipitation of Wave 3 was verified by Western Blot analysis. The NS1 protein and endogenous Wave 3 of crude cell lysates served as a control.

FIG. 15 shows the primers used in the Examples of the present document in 5'→3' direction.

DETAILED DESCRIPTION OF THE INVENTION

Figure 2B:
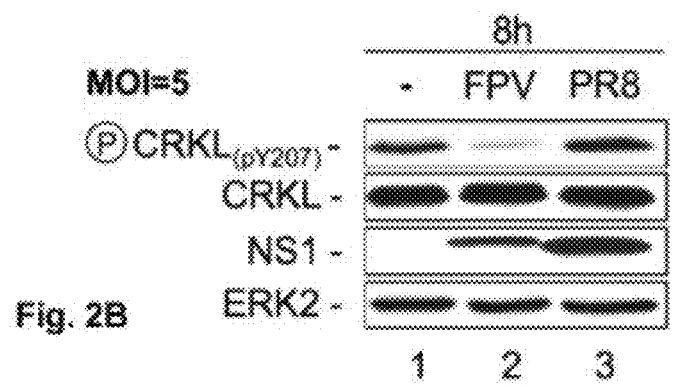

The present invention is based on the surprising finding that the non-structural protein 1 (NS1) of certain influenza A viruses (IAV), in particular avian influenza A viruses, contains sequence portions that have a strongly inhibitory effect on c-Abl. The NS1 protein has been described as a factor that has the capability of blocking cellular signalling events as well as actively inducing cellular signalling events (Ehrhardt, C., et al., Microbes Infect (2010) 12, 81-87). NS1 is a multifunctional protein consisting of an RNA-binding domain and several protein-protein interaction motifs including three src homology (SH) binding motifs (bm), one SH2bm and up to two SH3bms (Ehrhardt, C., Ludwig, S., Cell Microbiol (2009) 11, 863-871). The NS1 protein inter alia supports virus propagation by its interference with the innate and adaptive immune systems of the host (Hale, B. G., et al., J Gen Virol (2008) 89, 2359-2376. During the last decade, multiple independent studies focused on the role of different NS1 interactive domains including the SHbm and their function within the viral life cycle. One of the cellular targets of the viral NS1 protein is the regulatory subunit p85 of the phosphatidylinositol-3-kinase (PI3K). NS1 binding to p8513 has been intensively studied and the involvement of the SH2bm and the first SH3bm within NS1 has been reported (e.g. Hale et al., 2008, supra; Ehrhardt et al., 2009, Ehrhardt, 2011, Ludwig, 2011). Additionally, it was shown that the second SH3bm (SH3(II)bm) mediates binding to the family of CRK adaptor proteins (Heikkinen, L. S., et al., J Biol Chem (2008) 283, 5719-5727; Hrincius, E. R., et al., Cell Microbiol (2010) 12, 831-843). Interestingly, the evolutionary conservation of the different SHbm within NS1 is variable. While the binding-determining tyrosine 89 within the SH2bm is highly conserved, the sequence from aa212-217 at the SH3(II)bm is more diverse among different strains. Interestingly, NS1 proteins of avian IAV possess an SH3(II)bm whereas most of their counterparts of human IAV do not carry this motif. Recently, the different existence of the SH3(II)bm was confirmed by CRK protein binding ability of avian NS1 proteins but not of most human NS1 forms (Heikkinen et al., 2008, supra). As an exception of this rule, NS1 proteins of H5N1 strains lost the SH3(II)bm consensus and even almost all human H5N1 isolates do not encode a consensus SH3(II)bm in their NS1 protein (FIG. 10).

The present inventors have found that that the NS1 protein in general binds to c-Abl and NS1 proteins possessing the SH3(II)bm consensus block c-Abl kinase activity. Chemical inhibition of c-Abl attenuated virus growth of avian IAV. While mutational disruption of the SH3(II)bm increased virus titers of avian IAV, reconstitution of the SH3(II)bm in a H5N1 strain resulted in reduced viral propagation thereby linking inhibition of c-Abl to growth disadvantages. Finally, the inventors could show that the ability of avian IAV to block c-Abl kinase activity correlates with the induction of a strong cytopathogenic effect (CPE) that was diminished after loss of the SH3(II)bm consensus sequence.

The present inventors could further identify an amino acid sequence that is required for the binding of the NS1 protein to c-Abl. This sequence corresponds to amino acid positions 89-125 of the NS1 protein of the Influenza A virus strain A/Puerto Rico/8/1934 H1N1 with SwissProt/UniProt accession No. P03496, version 91 as of 11 Jul. 2012. The sequence with these amino acid positions is the sequence of SEQ ID NO: 11, in one letter code represented as: YLTDMTLEEMSRDWSMLIPKQKVAGPLCIRMDQAIMD.

Homologs of this sequence can likewise mediate binding to c-Abl and BCR-Abl. This sequence corresponds to amino acid positions 84-120 of the NS1 protein of the Influenza A virus strain A/Thailand/16/2004 H5N1 with SwissProt/UniProt accession No. A5A5U5, version 30 as of 16 May 2012. This sequence is included in the sequence of SEQ ID NO: 19, which corresponds to amino acid positions 88-125 of the NS1 protein of the Influenza A virus strain A/Puerto Rico/8/1934 H1N1 (supra), and has the sequence RYLTDMTLEEMSRDWSMLIPKQKVAGPLCIRMDQAIMD (SEQ ID NO: 19). The peptide or peptoid disclosed herein that includes the sequence of SEQ ID NO: 1 may in some embodiments include the sequence of SEQ ID NO: 19 or a homolog of this sequence. As will be apparent from the preceding explanations, a peptide as disclosed herein, for instance a peptide that includes, essentially consists of, or consists of a sequence of SEQ ID NO: 1, of SEQ ID NO: 23, of SEQ ID NO: 4, of SEQ ID NO: 2, or of SEQ ID NO: 20, is as such not found in nature.

A homolog is a biologically active sequence that has at least about 70%, including at least about 80% amino acid sequence identity with a given sequence of a polypeptide, such as the sequence of SEQ ID NO: 11. In some embodiments a homolog is a biologically active sequence that has at least about 85% amino acid sequence identity with the native sequence polypeptide. A homolog is a functional equivalent of an isolated nucleic acid molecule or an isolated peptide or protein described in this document. With regard to nucleic acid sequences, the degeneracy of the genetic code permits substitution of certain codons by other codons that specify the same amino acid and hence would give rise to the same protein. The nucleic acid sequence can vary substantially since, with the exception of methionine and tryptophan, the known amino acids can be coded for by more than one codon. Thus, portions or all of the nucleic acid sequences described herein could be synthesized to give a nucleic acid sequence significantly different from that shown in their indicated sequence. The encoded amino acid sequence thereof would, however, be preserved.

In addition, the nucleic acid sequence may include a nucleotide sequence which results from the addition, deletion or substitution of at least one nucleotide to the 5'-end and/or the 3'-end of the nucleic acid formula shown in a given sequence. Any nucleotide or polynucleotide may be used in this regard, provided that its addition, deletion or substitution does not alter the amino acid sequence, which is encoded by the nucleotide sequence. For example, the present invention is intended to include any nucleic acid sequence resulting from the addition of ATG as an initiation codon at the 5'-end of the inventive nucleic acid sequence or its derivative, or from the addition of TTA, TAG or TGA as a termination codon at the 3'-end of the inventive nucleotide sequence or its derivative. Moreover, a nucleic acid molecule according to the present invention may, as necessary, have restriction endonuclease recognition sites added to its 5'-end and/or its 3'-end. Such functional alterations of a given nucleic acid sequence afford an opportunity to promote secretion and/or processing of heterologous proteins encoded by foreign nucleic acid sequences fused thereto.

Further, it is possible to delete codons or to substitute one or more codons with codons other than degenerate codons to produce a structurally modified polypeptide, but one which has substantially the same utility or activity as the polypeptide produced by the unmodified nucleic acid molecule. As recognized in the art, the two polypeptides are functionally equivalent, as are the two nucleic acid molecules that give rise to their production, even though the differences between the nucleic acid molecules are not related to the degeneracy of the genetic code.

"Percent (%) sequence identity" with respect to amino acid sequences disclosed in this document is defined as the percentage of amino acid residues in a candidate sequence that are identical with the amino acid residues in a reference sequence, e.g. of SEQ ID NO: 11 or SEQ ID NO: 1, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared. The same is true for nucleotide sequences disclosed herein.

Those skilled in the art will be familiar with the fact that corresponding sequences need to be compared. The use of a corresponding sequence includes that a position is not only determined by the number of the preceding nucleotides/amino acids. Accordingly, the position of a given amino acid in accordance with the disclosure which may be substituted may very due to deletion or addition of amino acids elsewhere in a (mutant or wild-type) protein such as NS1. Thus, by a "corresponding position" in accordance with the disclosure it is to be understood that amino acids may differ in the indicated number—for instance when comparing data base entries—but may still have similar neighbouring amino acids.

As mentioned above, in some embodiments a sequence such as a sequence corresponding to SEQ ID NO: 11 or SEQ ID NO: 19 contains a conservative substitution. Conservative substitutions are generally the following substitutions, listed according to the amino acid to be mutated, each followed by one or more replacement(s) that can be taken to be conservative: Ala→Gly, Ser, Val; Arg→Lys; Asn→Gln, His; Asp→Glu; Cys→Ser; Gln→Asn; Glu→Asp; Gly→Ala; His→Arg, Asn, Gln; Ile→Leu, Val; Leu→Ile, Val; Lys→Arg, Gln, Glu; Met→Leu, Tyr, Ile; Phe→Met, Leu, Tyr; Ser→Thr; Thr→Ser; Trp→Tyr; Tyr→Trp, Phe; Val→Ile, Leu. Other substitutions are also permissible and can be determined empirically or in accord with other known conservative or non-conservative substitutions. As a further orientation, the following eight groups each contain amino acids that can typically be taken to define conservative substitutions for one another:

1) Alanine (Ala), Glycine (Gly);
2) Aspartic acid (Asp), Glutamic acid (Glu);
3) Asparagine (Asn), Glutamine (Gln);
4) Arginine (Arg), Lysine (Lys);
5) Isoleucine (Ile), Leucine (Leu), Methionine (Met), Valine (Val);
6) Phenylalanine (Phe), Tyrosine (Tyr), Tryptophan (Trp);
7) Serine (Ser), Threonine (Thr); and
8) Cysteine (Cys), Methionine (Met)

As an illustrative example, an exchange of L for I at position 8 of SEQ ID NO: 19, i.e. the sequence . . . RYLTDMTIEE . . . (SEQ ID NO: 64) instead of amino acid residues 1-10 of SEQ ID NO: 19, as observed in many variants such as e.g. NS1 of H2N2 virus A/Leningrad/134/47/ts+18/1957, in NS1 of H2N2 virus A/Fort Monmouth/1/1947, NS1 of H1N1 virus A/Memphis/54/1983 or NS1 of H1N1 virus A/Albany/1/1958 is a conservative substitution. As a further illustrative example, an exchange of I for M at position 19 of SEQ ID NO: 19, i.e. the sequence . . . MLMPK . . . (SEQ ID NO: 65) instead of amino acid residues 17-21 of SEQ ID NO: 19 as observed in e.g. NS1 of H9N2 virus A/chicken/Korea/A146/2009, in NS1 of H1N1 virus A/Memphis/54/1983, in NS1 of H6N2 virus A/wild duck/Shantou/1651/2000 or in NS1 of H2N2 virus A/Ann Arbor/6/60 is likewise a conservative substitution. Likewise, a conservative substitution is present via an exchange of M for L at position 11 of SEQ ID NO: 19, i.e. the sequence . . . EELSR . . . (SEQ ID NO: 66) instead of amino acid residues 9-13 of SEQ ID NO: 19 as observed in e.g. NS1 of H3N2 virus A/X-31. An exchange of I for L at position 3 of SEQ ID NO: 19, i.e. the sequence . . . RYITD . . . (SEQ ID NO: 67) instead of amino acid residues 1-5 of SEQ ID NO: 19 as observed in e.g. NS1 of H1N1 virus A/reassortant/NYMCX-211 (NYMC X-157×St. Petersburg/100/2011) is likewise a conservative substitution. Another example of a conservative substitution is an exchange of K for R at position 21 of SEQ ID NO: 19, i.e. the presence of the sequence . . . LIPRQK . . . (SEQ ID NO: 68) instead of amino acid residues 18-23 of SEQ ID NO: 19 as observed in e.g. NS1 of H1N1 virus A/swine/Hong Kong/NS1680/2001. As yet a further illustrative example, an exchange of I for V at position 30 of SEQ ID NO: 19, i.e. the sequence . . . VAGPLCVRMD . . . (SEQ ID NO: 69) instead of amino acid residues 24-33 of SEQ ID NO: 19, as observed in e.g. H1N1 viruses A/Memphis/2/1983 and A/Niigata/08F031/2009, is also a conservative substitution.

The same conservative substitution, i.e. an exchange of I→V can for instance be found at position 36 of SEQ ID NO: 19, . . . DQAVMD . . . (SEQ ID NO: 70) instead of amino acid residues 33-38 of SEQ ID NO: 19, as observed in e.g. H1N1 virus A/Cameron/1946. As another illustrative example, an exchange of R for K at position 31 of SEQ ID NO: 19, i.e. the sequence . . . LCIKMDQ . . . (SEQ ID NO: 71) instead of amino acid residues 28-34 of SEQ ID NO: 19, as observed in e.g. H5N1 strain A/chicken/Sichuan/81/2005, is a conservative substitution. As a further illustrative example, an exchange of M for L at position 11 of SEQ ID NO: 19, i.e. the sequence . . . LSRDWSMLIP . . . (SEQ ID NO: 72) instead of amino acid residues 11-20 of SEQ ID NO: 19 as observed in e.g. H5N1 strain A/chicken/Sichuan/81/2005, is also a conservative substitution. Yet another example of a conservative substitution is an exchange of D→E at position 14 of SEQ ID NO: 19, i.e. the sequence . . . MSREWSMLIP . . . (SEQ ID NO: 73) instead of amino acid residues 11-20 of SEQ ID NO: 19 as observed in e.g. H5N1 virus A/reassortant/NIBRG-14 (Viet Nam/1194/2004×Puerto Rico/8/1934).

In contrast thereto, more substantial changes, such as the following, do not represent conservative substitutions: Ala→ Leu, Ile; Arg→Gln; Asn→Asp, Lys, Arg, His; Asp→Asn; Cys→Ala; Gln→Glu; Glu→Gln; His→Lys; Ile→Met, Ala, Phe; Leu→Ala, Met, Norleucine; Lys→Asn; Met→Phe; Phe→Val, Ile, Ala; Trp→Phe; Tyr→Thr, Ser; Val→Met, Phe, Ala.

A comparison of amino acid sequences of various variants of the NS1 protein, all of which are able to bind to cAbl, has further shown that a number of amino acid positions are of low or of no relevance with regard to the binding of NS1 to c-Abl. A selected number of non-limiting examples shall serve in illustrating the potential modifications that fall within sequences that can effect binding to c-Abl—in other words modifications that may be present in a sequence used in the context of a combination, method or use described herein, since they do not abrogate the binding of the corresponding peptide/peptidomimetic to c-Abl or BCR-Abl: The NS1 protein of the H1N1 virus strain A/United Kingdom/1-MA/1933 has the sequence . . . RHLTDMTLEEMSRH-WFMLMP . . . (SEQ ID NO: 74) instead of amino acid residues 1-20 as present in SEQ ID NO: 19. Each of the exchange of Y to H at position 2 of SEQ ID NO: 19, the exchange of D to H at position 14 of SEQ ID NO: 19 and the exchange of S to F at position 16 of SEQ ID NO: 19, occurring in combination, do not hamper the function of NS1 to c-Abl, yet they are not conservative substitutions. These positions of non-conservative substitutions correspond to positions 1, 13 and 15 of SEQ ID NO: 11, respectively. The exchange I→M at position 19 of SEQ ID NO: 19, corresponding to position 18 of SEQ ID NO: 11, is a conservative substitution.

In this regard the NS1 protein of the H1N1 virus strain A/WS/1933 has the sequence . . . RYLTDMTLEEMSRH-WFMLMP . . . (SEQ ID NO: 75) and does thus not have an exchange at position 2 of SEQ ID NO: 19. Further, the NS1 protein of the H1N1 virus strain A/Phila/1935 has the sequence . . . RYLTDMTLEEMSRDWFMLMP . . . (SEQ ID NO: 76) and does thus not have an exchange at position 2 and at position 14 of SEQ ID NO: 19. However, it has a further non-conservative exchange at position 19 of SEQ ID NO: 19, where it carries an R instead of an I. The NS1 proteins of the H7N3 virus strains/Chicken/Rawalpindi/NARC68/2002, A/Chicken/Rawalpindi/NARC72/2002, A/Chicken/Chakwal/NARC-46/2003, A/Chicken/Chakwal/NARC-148/2003, A/Chicken/Chakwal/NARC-148/2004, A/Chicken/Karachi/NARC-23/2003, A/Chicken/Chakwal/NARC-23/2003, have the sequence . . . MSRDWFMLMP . . . (SEQ ID NO: 77) instead of amino acid residues 11-20 as present in SEQ ID NO: 19. The non-conservative exchange S→F at position 16 is likewise present in these NS1 variants. As a side note the conservative exchange I→M at position 19 of SEQ ID NO: 19 is also present in these variants (cf. above).

As a further example, the NS1 protein of the H1N1 virus strain A/Puerto Rico/8-CIP045_RG89697/1934 contains the sequence . . . RYLTDMTLAA . . . (SEQ ID NO: 78) instead of amino acid residues 1-10 as present in SEQ ID NO: 19. This NS1 protein thus has a sequence with the non-conservative substitution E→A at both position 9 and position 10 of SEQ ID NO: 19. As a further example, the NS1 protein of the H4N4 virus strains A/mallard/Washington/44242-271/2006 and A/mallard/Washington/44242-144/2006 include the sequence . . . MSRDWFMLMPKQKVA GSLCI . . . (SEQ ID NO: 79) instead of amino acid residues 11-30 as present in SEQ ID NO: 19. Non-conservative exchanges are present at position 16, an exchange of S for F, and at position 27 of SEQ ID NO: 19, an exchange of P for S. As yet a further example, the NS1 protein of the H1N1 virus strain A/Memphis/2/1983 includes the sequence . . . MSRDWFMLMPKQKVAGPLCV . . . (SEQ ID NO: 80) instead of amino acid residues 11-30 as present in SEQ ID NO: 19 and thus also includes the non-conservative substitution S→F at position 16. The NS1 proteins of the H4N4 virus strains A/mallard/Washington/44242-271/2006 and A/mallard/Washington/44242-144/2006 as well as of the H1N1 virus strain A/Memphis/2/1983 further have a conservative exchange of I→M at position 19 of SEQ ID NO: 19. NS1 of the H1N1 virus strain A/Memphis/2/1983 in addition has a conservative exchange of I→M at position 30 of SEQ ID NO: 19. The NS1 proteins of the H6N2 virus strain A/wild duck/Shantou/1651/2000 and of the H5N1 virus strain A/duck/Shantou/1930/2001 contain the sequence . . . MSRDWFMLMPKQKVAGPLCI . . . (SEQ ID NO: 81) instead of amino acid residues 11-30 as present in SEQ ID NO: 19, and accordingly the non-conservative substitution S→F at position 16.

Yet another example is the NS1 protein of the H1N1 virus strain A/swine/Hong Kong/NS1680/2001, which includes the sequence . . . RYLADMTLEEMSRDWFMLIPRQKI-IGSLCV . . . instead of amino acid residues 1-30 as present in SEQ ID NO: 19. Non-conservative exchanges can be found at position 4, an exchange of T→A, at position 16, an exchange S→F, at position 25, an exchange A→I, and at position 27, an exchange of P for S, at position 30, of SEQ ID NO: 19. NS1 of the H1N1 virus strain A/Memphis/2/1983 contains the sequence . . . VAGPPCIR (SEQ ID NO: 83) . . . instead of amino acid residues 24-31 as present in SEQ ID NO: 19, and accordingly has a non-conservative exchange of L→P at position 28 of SEQ ID NO: 19. A further example is the NS1 protein of the H5N1 virus strain A/chicken/Thailand/Udonthani-01/2004, which includes the sequence . . . MSGDWFMLMPKQKVAGSLCI (SEQ ID NO: 84) . . . instead of amino acid residues 11-30 as present in SEQ ID NO: 19. Non-conservative exchanges can be found at position 13, being an exchange R→G, at position 16, being an exchange S→F, at position 19, being an exchange I→M, and at position 27 an exchange of P→S, when compared to SEQ ID NO: 19. A further example of non-conservative substitutions can be found in the NS1 protein of the H6N1 virus strain A/chicken/Taiwan/0305/04, which contains the sequence . . . KQKVAGSLLI (SEQ ID NO: 85) . . . instead of amino acid residues 21-30 as present in SEQ ID NO: 19. It accordingly has a non-conservative exchange of P→S at position 27, as well as a non-conservative exchange of C→L at position 29 of SEQ ID NO: 19. Another example of a non-conservative substitution can be found in the NS1 protein of the H6N2 virus strain A/duck/Fujian/1695/2005. The sequence of this protein includes the sequence . . . KQKVAGPLFIKMD (SEQ ID NO: 86) . . . instead of amino acid residues 21-33 as present in SEQ ID NO: 19. A non-conservative exchange is again present at position 29 of SEQ ID NO: 19 in form of an exchange C→M, as well as a conservative exchange at position 31, in form of an exchange R→K. A further example of non-conservative substitutions can be found in the NS1 protein of the H3N2 virus strain A/Bilthoven/628/1976, which contains the sequence . . . KQKVEGPLCIRIDQA (SEQ ID NO: 87) . . . instead of amino acid residues 21-35 as present in SEQ ID NO: 19. It accordingly has a non-conservative exchange of A→E at position 25, as well as a non-conservative exchange of M→I at position 32 of SEQ ID NO: 19.

As a further example, the NS1 protein of the H5N1 virus strain A/chicken/Hunan/1/2009 contains the sequence . . . GPLMFKM (SEQ ID NO: 88) . . . instead of amino acid residues 26-32 as present in SEQ ID NO: 19. A stretch of three exchanges can be found at positions 29-31, with a non-conservative exchange C→M at position 29, a non-conservative exchange I→F at position 30 and a conservative exchange of R→K at position 31, when compared to SEQ ID NO: 19. Another example of a non-conservative substitution, relative to the sequence of SEQ ID NO: 19, is the exchange S→I at position 16, i.e. the sequence . . . RDWIML (SEQ ID NO: 89) . . . as found in the NS1 protein of the H9N2 virus strain A/duck/Shantou/3577/2003, instead of amino acid residues 13-18 of SEQ ID NO: 19. A further non-conservative substitution, relative to the sequence of SEQ ID NO: 19, in this stretch of amino acids can be found in the NS1 protein of the H9N2 virus strain A/duck/Beijing/MG0617/2005. In the sequence of this NS1 protein an exchange S→L at position 16, i.e. the sequence . . . RDWLM (SEQ ID NO: 90) . . . instead of amino acid residues 13-17 of SEQ ID NO: 19 of SEQ ID NO: 19.

Any of the above examples of conservative and non-conservative substitutions of amino acids, relative to SEQ ID NO: 19, alone or in any combination may be included in a peptide or peptidomimetic disclosed herein, and are encompassed by the sequence of SEQ ID NO: 1.

Analysis has thus revealed that the region of NS-1 proteins corresponding to SEQ ID NO: 1 allows binding of a peptide/protein to c-Abl, including to BCR-Abl. Accordingly a peptide of the sequence of SEQ ID NO: 1, or a homolog thereof, is part of a combination or a peptide/protein disclosed herein.

As explained above, in some embodiments the present invention provides a peptide or a combination of peptides. Where a peptide is provided, the peptide is isolated. Likewise where a combination of peptides is provided, the peptides of the combination of peptides are isolated. The term "isolated" indicates that the peptide(s) or nucleic acid molecule(s) has/have been removed from its/their normal physiological environment, e.g. a natural source, or that a peptide or nucleic acid is synthesized. Use of the term "isolated" indicates that a naturally occurring sequence has been removed from its normal cellular, e.g. chromosomal, environment. Thus, the sequence may be in a cell-free medium or placed in a different cellular environment. Thus, a cell or cells may be included in a different medium such as an aqueous solution than provided originally, or placed in a different physiological environment. Typically isolated cells, peptides or nucleic acid molecule(s) constitute a higher fraction of the total cells, peptides or nucleic acid molecule(s) present in their environment, e.g. solution/suspension as applicable, than in the environment from which they were taken. By "isolated" in reference to a polypeptide or nucleic acid molecule is meant a polymer of amino acids (2 or more amino acids) or nucleotides coupled to each other, including a polypeptide or nucleic acid molecule that is isolated from a natural source or that is synthesized. The term "isolated" does not imply that the sequence is the only amino acid chain or nucleotide chain present, but that it is essentially free, e.g. about 90-95% pure or more, of e.g. non-amino acid material and/or non-nucleic acid material, respectively, naturally associated with it.

A peptide or a combination of peptides disclosed herein includes the amino acid sequence of SEQ ID NO: 1, or a homolog thereof. The peptide or a combination of peptides further includes the amino acid sequence of SEQ ID NO: 2. The inventors have found that the amino acid sequence of SEQ ID NO: 2 is capable of inhibiting the protein kinase activity of c-Abl, including of BCR-Abl. A second amino acid sequence that is included in the peptide or a combination of peptides disclosed herein is the sequence of SEQ ID NO: 2. The peptide or a combination of peptides that includes these two amino acid sequences can be used in a method of treating a BCR-ABL associated disease or a c-ABL associated disease in a subject.

In some embodiments SEQ ID NO: 2 has, in one letter code, the amino acid sequence PSLPPK (SEQ ID NO: 91), as in e.g. Influenza A virus strains A/duck/Korea/GJ74/2007 (H3N1) or A/duck/Shantou/1090/2001(H6N2). In some embodiments SEQ ID NO: 2 has, in one letter code, the amino acid sequence PSLPPN (SEQ ID NO: 92), as in e.g. strain A/duck/Korea/GJ108/2007(H3N2). In some embodiments SEQ ID NO: 2 has the amino acid sequence PPFPPK (SEQ ID NO: 93), as in e.g. strain A/Philippines/344/2004 (H1N2). In some embodiments SEQ ID NO: 2 has the amino acid sequence PPFPPN (SEQ ID NO: 94), as in e.g. strain A/chicken/West Java/Smi-Biot/2008(H5N1). In some embodiments SEQ ID NO: 2 has the amino acid sequence PSFPPK (SEQ ID NO: 95), as in e.g. strain A/African starling/England-Q/983/1979(H7N1). In some embodiments SEQ ID NO: 2 has the amino acid sequence PPFPTK (SEQ ID NO: 96), as in e.g. strain A/swine/Italy/259543/2003(H1N2). In some embodiments SEQ ID NO: 2 has the amino acid sequence PPFPSK (SEQ ID NO: 97), as in e.g. strain A/swine/Italy/526/1985(H3N2). In some embodiments SEQ ID NO: 2 has the amino acid sequence PPFPAK (SEQ ID NO: 98), as in e.g. strain A/mallard/Mississippi/360/2010(H3N8). In some embodiments SEQ ID NO: 2 has the amino acid sequence PSFPPK (SEQ ID NO: 99), as in e.g. strain A/equine/Tennessee/5/1986(H3N8). In some embodiments SEQ ID NO: 2 has the amino acid sequence PSFPSK (SEQ ID NO: 100), as in e.g. strain A/canine/Colorado/17864/2006(H3N8). In some embodiments SEQ ID NO: 2 has the amino acid sequence PPLPSN (SEQ ID NO: 101), as in e.g. strain A/goose/Yunnan/4129/2005 (H5N1). In some embodiments SEQ ID NO: 2 has the amino acid sequence PPLPTK (SEQ ID NO: 102), as in e.g. strain A/duck/Vietnam/OIE-1234/2012(H3N2). In some embodiments SEQ ID NO: 2 has the amino acid sequence PPLPSK (SEQ ID NO: 103), as in e.g. strain A/chicken/Taiwan/0706/03(H6N1). In some embodiments SEQ ID NO: 2 has the amino acid sequence PPLPAK (SEQ ID NO: 104), as in e.g. strain A/red-necked stint/Australia/5745/1981(H12N9).

As indicated above, instead of or in addition to peptides, peptidomimetics may likewise be used in the context of the present invention. The term "peptidomimetic" as used herein refers to a compound that has the same general structure as a corresponding polypeptide, but which includes modifications that increase its stability or biological function. In some embodiments a peptidomimetic may include one or more D-amino acids, essentially consist of D-amino acids or consist of D-amino acids. D-amino acids are the optical isomer of a naturally occurring L amino acid. A D amino acid can be taken to be a mirror image of a L amino acid. Stretches of D amino acids are less prone to be degraded in a host organism via proteolysis. In some embodiments a peptidomimetic may be an inverso analog, which is an analog of the same sequence that consists only of D amino acids. In some embodiments a peptidomimetic may be a "reverso" analogue of a given peptide, which means that the peptidomimetic includes the reverse sequence of the peptide. In some embodiments a peptidomimetic may be a "D-retro-enantiomer peptide", which is an analog that consists of D-amino acids, with the sequence arranged in the reversed order. A peptidomimetic may also include, essentially consist of or consist of a peptoid. A peptoid differs from peptides in that the side chain is connected to the amide nitrogen rather than the a carbon atom. A peptoid can thus be taken to be an oligo(N-alkyl) glycine, which nevertheless has the same or substantially the same amino acid sequence as the corresponding polypeptide. Peptoids are typically resistant to proteases and other modifying enzymes and can have a much higher cell permeability than peptides (see e.g. Kwon, Y.-U., and Kodadek, T., *J. Am. Chem. Soc.* (2007) 129, 1508-1509).

In some embodiments a peptide or peptidomimetic or the combination of a first and a second peptide or peptidomimetic as disclosed herein includes a sequence that represents a cell penetrating motif or other moiety so as to more efficiently facilitate the delivery of the peptide or peptidomimetic to the interior of a cell, anchor the peptide to the cell membrane of a cell, and/or promote folding of the peptide. Any of various cell penetrating motifs and or other moieties useful for these purposes can be used. As an illustrative example, suitable cell penetrating motifs and other relevant moieties (e.g., cell-membrane anchoring moieties) include a lipid and a fatty acid, a peptide transduction domain (e.g., HIV-TAT, HSV Transcription Factor (VP22), and penetratin), and other types of carrier molecules (e.g., Pep-I).

In some embodiments the cell penetrating motif or other moiety includes a fatty acid or lipid molecule. The fatty acid or lipid molecule can be, for example, a palmitoyl group, a farnesyl group such as farnesyl diphosphate, a geranylgeranyl group such as geranylgeranyl diphosphate, a phospholipid group, glycophosphatidylinositol, phosphatidylserine, phosphatidylethanolamine, sphingomyelin, phosphatidylcholine, cardiolipin, phosphatidylinositol, phosphatide acid, lysophosphoglyceride, and a cholesterol group. In some embodiments the fatty acid molecule has a main chain of a length of one to 24 carbon atoms, including 6 to 20 carbon atoms or 8 to 16 carbon atoms. The main chain of a respective fatty acid may include three or more, including four or more, five or more, six or more, seven or more, eight or more, nine or more or ten or more carbon atoms. Typically, the main chain of the fatty acid includes 22 or less, 20 or less, 18 or less, or 16 or less carbon atoms. Specific examples of a fatty acid include, but are not limited to, lauric acid, palmitic acid, myristic acid, stearic acid, oleic acid, linoleic acid, α-linoleic acid, linolenic acid, arachidonic acid, timnodonic acid, docosohexenoic acid, erucic acid, arachidic acid, and behenic acid (docosanoic acid).

The fatty acid or lipid molecule may be coupled to any suitable part of the peptide or peptidomimetic. In some embodiments the fatty acid or lipid molecule is attached at the amino (N-) terminus, the carboxyl (C-) terminus, or both the N- and C-termini of the peptide or peptidomimetic. Typically, the fatty acid or lipid molecule is attached via an amide or ester linkage. When the fatty acid or lipid molecule is attached at the C-terminus of the polypeptide or peptidomimetic, the fatty acid or lipid molecule may include an amino group such as $NH_2(CH_2)_nCOOH$ or $CH_3(CH_2)_mCH(NH_2)COOH$, wherein each of n and m is, independently, selected from the range 1 to 24, including 8 to 16, such as 9, 10, 11, 12, 13, 14 or 15. The fatty acid or lipid residue can advantageously be attached to a terminal lysine in the epsilon (ε) position.

In some embodiments the cell penetrating motif is a peptide transduction domain, also known as a protein transduction domain or PTD. A PTD may be fused to a peptide or peptidomimetic used in the context of a combination, method or use disclosed herein. A combination as described in this specification may also include a sequence of SEQ ID NO: 1 or a homolog thereof, a sequence of SEQ ID NO: 2 and a peptide transduction domain. Often, a fusion protein is cleaved inside a cell to remove the cell penetrating motif.

The peptide or peptidomimetic may be prepared by any method, such as by synthesizing the peptide or peptidomimetic, or by expressing a nucleic acid encoding an appropriate amino acid sequence in a cell and harvesting the peptide from the cell. A combination of such methods may likewise be used. Methods of de novo synthesizing peptides and peptidomimetics, and methods of recombinantly producing peptides and peptidomimetics are well known in the art.

The peptide or peptidomimetic, or the combination of peptides or peptidomimetics disclosed herein is/are capable of interfering with c-Abl signalling. The terms "signalling" and "signal transduction pathway" refer to cellular mechanisms and to molecules that act on cellular components in response to a certain condition, change or external stimulus. Typically such mechanisms and molecules propagate an extracellular signal through the cell membrane to become an intracellular signal. This signal can then stimulate a cellular response.

In some embodiments the combination of one or more peptides is a single protein in the form of the protein NS1 of an influenza A strain. In some embodiments the combination of one or more peptides includes the protein NS1 of an influenza A strain. A suitable NS1 protein may be any protein that includes the amino acid sequences of SEQ ID NO: 1 and SEQ ID NO: 2. NS1 of as good as any avian influenza A strain is suitable in this regard. As a few illustrative examples of suitable NS1 proteins of an avian influenza A strain include, but are not limited to, the NS1 protein of Influenza A virus strain A/Mallard/Ohio/556/1987 H5N9 with the Swissprot/Uniprot accession number O41649 (version 53 as of 18 Apr. 2012), the NS1 protein of Influenza A virus strain A/pintail/Ohio/294/1988(H6N2) of the Swissprot/Uniprot accession number Q0R7T5 (version 50 as of 16 May 2012), the NS1 protein of Influenza A virus strain A/Seal/Massachusetts/133/1982 (H4N5) with the Swissprot/Uniprot accession number Q9YPE8 (version 52 as of 18 Apr. 2012), the NS1 protein of Influenza A virus strain A/chicken/Taiwan/0824/97(H6N1) with the Swissprot/Uniprot accession number Q0QH16 (version 34 as of 16 May 2012), the NS1 protein of Influenza A virus strain strain A/Fowl plague virus/Rostock/8/1934 (H7N1) with the Swissprot/Uniprot accession number P03500 (version 74 as of 18 Apr. 2012), the NS1 protein of Influenza A virus strain A/duck/Shantou/4534/2001(H6N2) with the Swissprot/Uniprot accession number D9IIB9 (version 4 as of 16 May 2012), the NS1 protein of Influenza A virus strain A/Aquatic bird/Hong Kong/M603/98 (H11N1) of the Swissprot/Uniprot accession number Q9IGL9 (version 51 as of 16 May 2012), the NS1 protein of Influenza A virus strain A/northern shoveler/Washington/44249-603/2006 (H6N1) of the Swissprot/Uniprot accession number E3JMW7 (version 4 as of 16 May 2012), the NS1 protein of Influenza A virus strain A/Ck/HK/31.4/02 (H5N1) of the Swissprot/Uniprot accession number Q6J874 (version 42 as of 16 May 2012) or the NS1 protein of Influenza A virus strain A/duck/Western Australia/8069/1984 (H4N6) with the Swissprot/Uniprot accession number F8IXN5 (version 5 as of 16 May 2012).

Examples of NS1 proteins of suitable human influenza strains are the NS1 protein of Influenza A virus strain A/Brevig Mission/1/1918 (H1N1), which has the Swissprot/Uniprot accession number Q99AU3 (version 47 as of 18 Apr. 2012), the NS1 protein of Influenza A virus strain A/Hong Kong/481/97 (H5N1) of the Swissprot/Uniprot accession number Q9INP1 (version 50 as of 16 May 2012) or of the Swissprot/Uniprot accession number Q91U32 (version 49 as of 16 May 2012), and the NS1 protein of Influenza A virus strain A/Canada/rv504/2004 (H7N3) of the Swissprot/Uniprot accession number Q0A2S6 (version 30 as of 16 May 2012).

A combination of one or more nucleic acid molecules disclosed herein contains one or more sequences that encode one or more peptides/proteins. Among these encoded sequences, or this encoded sequence, is a sequence that encodes the sequence of SEQ ID NO: 1 or a homolog thereof. Further, among these encoded sequences, or this encoded sequence, is a sequence encoding the sequence of SEQ ID NO: 2. In some embodiments the combination of one or more nucleic acid molecules encodes a peptide chain that includes both a sequence of SEQ ID NO: 1 or a homolog thereof and a sequence of SEQ ID NO: 2. In some embodiments one nucleic acid molecule disclosed herein encodes a single peptide/protein, which encompasses the sequence of SEQ ID NO: 1 or a homolog thereof and the sequence of SEQ ID NO: 2.

The term "nucleic acid" as used herein refers to any nucleic acid molecule in any possible configuration, such as single stranded, double stranded or a combination thereof. Nucleic acids include for instance DNA molecules, RNA molecules, analogues of the DNA or RNA generated using nucleotide analogues or using nucleic acid chemistry, locked nucleic acid molecules (LNA), protein nucleic acids molecules (PNA) and tecto-RNA molecules (e.g. Liu, B., et al., *J. Am. Chem. Soc.* (2004) 126, 4076-4077). A PNA molecule is a nucleic acid molecule in which the backbone is a pseudopeptide rather than a sugar. Accordingly, PNA generally has a charge neutral backbone, in contrast to for example DNA or RNA. Nevertheless, PNA is capable of hybridising at least complementary and substantially complementary nucleic acid strands, just as e.g. DNA or RNA (to which PNA is considered a structural mimic). An LNA molecule has a modified RNA backbone with a methylene bridge between C4' and O2', which locks the furanose ring in a N-type configuration, providing the respective molecule with a higher duplex stability and nuclease resistance. Unlike a PNA molecule an LNA molecule has a charged backbone. DNA or RNA may be of genomic or synthetic origin and may be single or double stranded. Such nucleic acid can be e.g. mRNA, cRNA, synthetic RNA, genomic DNA, cDNA, synthetic DNA, a copolymer of DNA and RNA, oligonucleotides, etc. A respective nucleic acid may furthermore contain non-natural nucleotide analogues and/or be linked to an affinity tag or a label.

Many nucleotide analogues are known and can be used in a method according to the invention. A nucleotide analogue is a nucleotide containing a modification at for instance the base, sugar, or phosphate moieties. As an illustrative example, a substitution of 2'-OH residues of siRNA with 2'F, 2'O-Me or 2'H residues is known to improve the in vivo stability of the respective RNA. Modifications at the base moiety include natural and synthetic modifications of A, C, G, and T/U, different purine or pyrimidine bases, such as uracil-5-yl, hypoxanthin-9-yl, and 2-aminoadenin-9-yl, as well as non-purine or non-pyrimidine nucleotide bases. Other nucleotide analogues serve as universal bases. Universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

On a general basis the present invention also includes methods and uses of diagnosing and treating a c-Abl and/or BCR-Abl disorder, i.e. a disorder, condition, or disease state characterized by aberrant c-Abl signalling (see above for examples). In a specific aspect, the aberrant c-Abl signaling is a level of c-Abl signaling in a cell or tissue suspected of being diseased that exceeds the level of c-Abl signaling in a similar non-diseased cell or tissue. In a specific aspect, a c-Abl-mediated disorder includes a tumour, including cancer. The use of a peptide or peptidomimetic, or of the combination of a first and a second peptide or peptidomimetic, disclosed herein allows blocking or reducing the protein kinase activity, typically an aberrant elevated tyrosine kinase activity, of a c-Abl or BCR-Abl protein.

In some methods and uses according disclosed herein the protein kinase activity of a c-Abl or BCR-Abl protein, or a functional fragment thereof, is being reduced within a cell. The cell may be any cell that is capable of expressing a c-Abl or BCR-Abl protein. It may for example be an individual cell or a cell of a cell population. In some embodiments the cell is a somatic cell. Examples of suitable somatic cells, include, but are not limited to a fibroblast, a myeloid cell, a B lymphocyte, a T lymphocyte, a bone cell, a bone marrow cell, a pericyte, a dendritic cell, a keratinocyte, an adipose cell, a mesenchymal cell, an epithelial cell, an epidermal cell, an endothelial cell, a chondrocyte, a cumulus cell, a neural cell, a glial cell, an astrocyte, a cardiac cell, an oesophageal cell, a muscle cell (e.g. a smooth muscle cell or a skeletal muscle cell), a pancreatic beta cell, a melanocyte, a hematopoietic cell, a myocyte, a macrophage, a monocyte, and a mononuclear cell. A somatic cell may be a cell of any tissue, such as for instance skin, kidney, spleen, adrenal, liver, lung, ovary, pancreas, uterus, stomach, colon, small intestine, spleen, bladder, prostate, testicular, thymus, muscle, connective tissue, bone, cartilage, vascular tissue, heart, eye or neural tissue.

In some embodiments the cell is obtained or derived from a host organism, which may be any organism. The cell may be directly taken from a respective host organism in form of a sample such as e.g. a biopsy or a blood sample. It may also have been derived from a host organism and subsequently been cultured, grown, transformed or exposed to a selected treatment. In some embodiments the cell may be included in a host organism. It may for instance be present in the blood or in tissue, including in an organ, of the host organism. The host organism from which the cell is derived or obtained, or in which it is included, may be any organism such as a microorganism, an animal, such as a fish, an amphibian, a reptile, a bird, a mammal, including a rodent species, an invertebrate species, e.g. of the subclass Lissamphibia that includes e.g. frogs, toads, salamanders or newts, or a plant. Examples of mammals include, but are not limited to, a rat, a mouse, a rabbit, a guinea pig, a squirrel, a hamster, a vole, a platypus, a dog, a goat, a sheep, cattle, a pig, a chicken, a macaque or a human.

In some embodiments the cell is a tumour cell, e.g. a cancer cell. A respective tumour cell may also be obtained from an organism, e.g. from a mammal. In other embodiments the tumour cell may be included in a mammal, such as for example a rat, a cow, a pig, and a human. A respective tumour cell may also be cultured. It may for instance be a cell of a cell line, such as, but not limited to, a cell of one of the human acute myeloid leukemia cell lines THP1, K562, KG-1, HL-60, JURL-MK1 and JURL-MK2, a cell of one of the colorectal cancer cell lines SW480, HT29, RKO, LST-R1, Caco-2, WiDr, GP2d, HCT116, LoVo, LS174T, VACO5 HCA7, LS411, C70, LIM1863, SL-174T, SW1417, SW403, SW620, SW837 or VACO4A, one of the melanoma cell lines A375, B16 (including B16-F10), BN1, K1735-M2, M14, OCM-1 or WM793, one of the hepatoma cell lines FHCC-98, H4IIE Hep G2, Hep G2f, Huh-7, PLHC-1, SMMC-7721, SK-Hep1 or QGY, one of the lung cancer cell lines A549, ABC-1, EBC-1, LC-1/sq, LCD, LCOK, LK-2, Lu135, MS-1, NCI-H69, NCI H157, NCI-N231, NL9980, PC1, PC3, PC7, PC9, PC10, PC14, QG56, RERF-LCMS, RERF-LCAI, RERF-LCKJ, SBC3 or SQ5, one of the oesophageal cancer cell lines A549, EC109, EC9706 or HKESC-4, one of the gastric cancer cell lines BGC823, KATO-III, MGC803, MKN-45, SGC7901 or one of the ovarian cancer cell lines A2780, C13*, CAOV3, DOV-13, HO8910 (including HO-8910PM), OvCA 3, OvCA 420, OvCA 429, OvCA 432, OvCA 433, OvCar 3, OvCar 5, OvCA 420, OVHM or SKOV-3.

A cell used in a method according to the present invention is typically capable of expressing a c-Abl protein or BCR-Abl protein in that it includes a nucleic acid sequence encoding a c-Abl protein or BCR-Abl protein, for example in the form of a functional gene of the c-Abl protein (whether homologous or heterologous). The cell may also include a nucleic acid sequence that is capable of expressing the BCR-Abl fusion protein. In some embodiments the cell expresses the c-Abl protein and/or the BCR-Abl fusion protein. In some embodiments a respective, for instance homologous, gene encoding a c-Abl protein is functionally active and expressing the c-Abl protein. In some embodiments an expression cassette, for instance heterologous, encoding a c-Abl protein is functionally active and expressing the BCR-Abl protein. In some embodiments an endogenous nucleic acid sequence encoding a c-Abl protein is functionally inactive. In some of these embodiments a c-Abl protein and/or a BCR-Abl protein is nevertheless expressed—generally from a heterologous c-Abl expression cassette and/or a heterologous BCR-Abl expression cassette. A heterologous gene or expression cassette encoding a c-Abl protein or BCR-Abl protein may be introduced by means of recombinant technology, for instance by means of a vector carrying a c-Abl protein gene (cf. also below). It may in this regard be advantageous to further use a vector that contains a promoter effective to initiate transcription in the respective host cell (whether of endogenous or exogenous origin).

As used herein, the term "expression cassette" refers to a nucleic acid molecule capable of directing expression of a particular nucleotide sequence in an appropriate host cell. An expression cassette includes a promoter operatively linked to the nucleotide sequence of interest, which is operatively linked to one or more termination signals. It may also include sequences required for proper translation of the nucleotide sequence. The coding region can encode a polypeptide of interest and can also encode a functional RNA of interest, including but not limited to, antisense RNA or a non-translated RNA, in the sense or antisense direction. The expression cassette that contains the nucleotide sequence of interest can be chimeric, meaning that at least one of its components is heterologous with respect to at least one of its other components. The expression cassette can also be one that is naturally occurring but has been obtained in a recombinant form useful for heterologous expression. In some embodiments, however, the expression cassette is heterologous with respect to the host; i.e., the particular nucleic acid sequence of the expression cassette does not occur naturally in the host cell and was introduced into the host cell or an ancestor of the host cell by a transformation event. The expression of the nucleotide sequence in the expression cassette can be under the control of a constitutive promoter or of an inducible promoter that initiates transcription only when the host cell is exposed to some particular external stimulus. In the case of a multicellular organism such as a plant or an animal, the promoter can also be specific to a particular tissue, organ, or stage of development.

By "gene" is meant a unit of inheritance that occupies a specific locus on a chromosome and that is a segment of nucleic acid associated with a biological function. A gene encompasses transcriptional and/or translational regulatory sequences as well as a coding region. Besides a coding sequence a gene may include a promoter region, a cis-regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

The term "vector", sometimes also referred to as gene delivery system or gene transfer vehicle, relates to a macromolecule or complex of molecules that include(s) a polynucleotide to be delivered to a host cell, whether in vitro, ex vivo or in vivo. Typically a vector is a single or double-stranded circular nucleic acid molecule that allows or facilitates the transfer of a nucleic acid sequence into a cell. A vector can generally be transfected into cells and replicated within or independently of a cell genome. A circular double-stranded nucleic acid molecule can be cut and thereby linearized upon treatment with restriction enzymes. An assortment of nucleic acid vectors, restriction enzymes, and the knowledge of the nucleotide sequences cut by restriction enzymes are readily available to those skilled in the art. A nucleic acid molecule encoding a peptide, such as a sequence that includes a sequence of SEQ ID NO: 1 or a homolog thereof and/or a sequence of SEQ ID NO: 2, can be inserted into a vector by cutting the vector with restriction enzymes and ligating the two pieces together. A vector may for instance be a viral vector, such as a retroviral vector, a Lentiviral vector, a herpes virus based vector or an adenoviral vector. A vector may also be a plasmid vector, which is also a typical example of a prokaryotic vector. A respective plasmid may in some embodiments be a plasmid capable of replication in *E. coli*, such as, for example, pBR322, Co1E1, pSC101, pACYC 184 or πVX. *Bacillus* plasmids include pC194, pC221 or pT127. Suitable *Streptomyces* plasmids include p1J101, and *streptomyces* bacteriophages such as φC31. A vector may also be a liposome-based extrachromosomal vector, also called episomal vector. Two illustrative examples of an episomal vector are an oriP-based vector and a vector encoding a derivative of EBNA-1. Lymphotrophic herpes virus is a herpes virus which replicates in a lymphoblast and becomes a plasmid for a part of its natural life-cycle. A vector may also be based on an organically modified silicate. In some embodiments a vector may be a transposon-based system, i.e. a transposon/transposase system, such as the so called Sleeping Beauty, the Frog Prince transposon-transposase system or the TTAA-specific transposon piggyBac system. Transposons are mobile genetic elements in that they are sequences of DNA that can move around to different positions within the genome of a single cell, a process called transposition. In the process, a transposon can cause mutations and change the amount of DNA in the genome.

The term "promoter" as used throughout this document, refers to a nucleic acid sequence needed for gene sequence expression. Promoter regions vary from organism to organism, but are well known to those skilled in the art for different organisms. For example, in prokaryotes, the promoter region contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like. Both constitutive and inducible promoters can be used in a method or use disclosed herein, in accordance with the needs of a particular embodiment. A large number of promoters recognized by a variety of potential host cells are well known. The selected promoter can be operably linked to cistron DNA encoding a polypeptide described herein by removing the promoter from the source DNA via restriction enzyme digestion and inserting the isolated promoter sequence into the vector of choice. Both the native promoter sequence and many heterologous promoters may be used to direct amplification and/or expression of a selected nucleic acid sequence.

In a method or use disclosed herein a nucleic acid may be introduced into a host cells by any suitable technique of nucleic acid delivery for transformation of a cell available in the art. Examples of suitable techniques include, but are not limited to, direct delivery of DNA, e.g. via transfection, injection, including microinjection, electroporation, calcium phosphate precipitation, by using DEAE-dextran followed by polyethylene glycol, direct sonic loading, liposome mediated transfection, receptor-mediated transfection, microprojectile bombardment, agitation with silicon carbide fibers, *Agrobacterium*-mediated transformation, desiccation/inhibition-mediated DNA uptake or any combination thereof.

A method or use disclosed herein may further include measuring the expression of a sequence that includes a sequence of SEQ ID NO: 1 or a homolog thereof and/or a sequence of SEQ ID NO: 2. This can for instance be achieved by determining the number of RNA molecules transcribed from an encoding nucleic acid molecule that is under the control of a selected promoter. A method commonly used in the art is the subsequent copy of RNA to cDNA using reverse transcriptase and the coupling of the cDNA molecules to a fluorescent dye. The analysis may for example be performed in form of a DNA microarray. Numerous respective services and kits are commercially available, for instance GeneChip® expression arrays from Affymetrix. Other means of determining gene expression of a transcription factor include, but are not limited to, oligonucleotide arrays, and quantitative Real-time Polymerase Chain Reaction (RT-PCR).

In some embodiments it may be advantageous or desired to calibrate peptide/protein expression data or to rate them. Thus, in some embodiments a method disclosed herein additionally includes the comparison of obtained results with those of one or more control measurements. Such a control measurement may include any condition that varies from the main measurement itself. It may include conditions of the method under which for example no expression of the respective peptide/protein occurs. A further means of a control measurement is the use of a mutated form of a respective peptide/protein, for example a nucleic acid sequence or gene not encoding the corresponding peptide/protein that includes the sequence of SEQ ID NO: 1, or the homolog of SEQ ID NO: 1, and/or the peptide/protein that includes the sequence of SEQ ID NO: 2, or encoding a non-functional peptide/protein.

In some embodiments the protein kinase activity of a c-Abl protein and/or a BCR-Abl protein is determined. Assessing the protein kinase activity of a c-Abl protein and/or a BCR-Abl protein may include a measurement of the phosphorylation of a known substrate of c-Abl. As an illustrative example, a suitable donor such as ATP may be added, which has a radioactive label. As a further example, an antibody may be used that specifically binds to the phosphorylated form of a known substrate.

As explained above, a peptide, peptidomimetic or combination of peptides and/or peptidomimetics disclosed herein may be used to treat or prevent a c-Abl protein and/or a BCR-Abl associated condition or disease in a subject, such as cancer.

The term "preventing" refers to decreasing the probability that an organism contracts or develops an abnormal condition.

"Treating" or "treatment" or "alleviation" refers to both therapeutic treatment and prophylactic or preventative measures, wherein the object is to prevent, slow down (lessen) or at least partially alleviate or abrogate an abnormal, including pathologic, condition in the organism. Those in need of treatment include those already with the disorder as well as those prone to having the disorder or those in whom the disorder is to be prevented (prophylaxis). When the condition is cancer, a subject or mammal is successfully "treated" or shows a reduced tumour burden if, after having undergone a treatment based on a method or use disclosed herein, the individual shows observable and/or measurable reduction in or absence of one or more of the following: reduction in the number of cancer cells or absence of the cancer cells; reduction in the tumour size; inhibition (i.e., slow to some extent and preferably stop) of cancer cell infiltration into peripheral organs including the spread of cancer into soft tissue and bone; inhibition (i.e., slow to some extent and preferably stop) of tumour metastasis; inhibition, to some extent, of tumour growth; and/or relief to some extent, one or more of the symptoms associated with the specific cancer; reduced morbidity and mortality, and improvement in quality of life issues. To the extent a use or method disclosed herein may prevent growth and/or kill existing cancer cells, it may be cytostatic and/or cytotoxic.

Reduction of these signs or symptoms may also be felt by a respective patient.

The above parameters for assessing successful treatment and improvement in the disorder are readily measurable by routine procedures familiar to a physician. For cancer therapy, efficacy can be measured, for example, by assessing the time to disease progression (TDP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

The term "administering" relates to a method of incorporating a compound into cells or tissues of an organism.

The term "therapeutic effect" refers to the inhibition or activation of factors causing or contributing to the abnormal condition. A therapeutic effect relieves to some extent one or more of the symptoms of the abnormal condition.

The term "aberration" or "aberrant", in conjunction with the function of a cellular signal transduction process, refers to a component of such a process, e.g. a kinase, that is over- or under-expressed in an organism, altered such that its catalytic activity is lower or higher than corresponding wild-type activity, altered such that it can no longer interact with a natural binding partner, is no longer modified by another factor, e.g. protein or protein phosphatase, or no longer interacts with a natural binding partner.

The abnormal condition caused by an aberrant activity of c-Abl and/or BCR-Abl may be prevented or treated when the cells or tissues of the organism exist within the organism or outside of the organism. Cells existing outside the organism can be maintained or grown in cell culture dishes. For cells harboured within the organism, many techniques exist in the art to administer compounds, including (but not limited to) oral, parenteral, dermal, injection, and aerosol applications. For cells outside of the organism, multiple techniques exist in the art to administer the compounds, including (but not limited to) cell microinjection techniques, transformation techniques, and carrier techniques.

The abnormal condition can also be prevented or treated by administering a compound to a group of cells having an aberration in the c-Abl signal transduction pathway to an organism. The effect of administering a compound on organism function can then be monitored. The organism may or instance be a mammal, such as a mouse, a rat, a rabbit, a guinea pig, a goat, a monkey or an ape. In some embodiments the organism is a human.

The term "abnormal condition" refers to a function in the cells or tissues of an organism that deviates from their normal or standard functions in that organism. An abnormal condition can relate to cell proliferation, cell differentiation, or cell survival. The terms "cell proliferative disorder" and "proliferative disorder" refer to disorders that are associated with some degree of abnormal cell proliferation such as a tumour. The word "tumour", as used herein, refers to all neoplastic cell growth and proliferation, whether malignant or benign, and all pre-cancerous and cancerous cells and tissues.

Abnormal cell proliferative conditions include cancer, fibrotic and mesangial disorders, abnormal angiogenesis and vasculogenesis, wound healing, psoriasis, diabetes mellitus, and inflammation. Furthermore, the proliferative disorders can relate to conditions in which programmed cell death (apoptosis) pathways are abrogated. As a number of proteins the expression of which is under control of the c-Abl signal transduction pathway are associated with the apoptosis pathways, aberrations in the c-Abl signal transduction pathway can lead to cell immortality.

In the methods and uses of treating a c-Abl and/or a BCR-Abl associated condition in a subject further compounds may be employed that inhibit the protein kinase activity of c-Abl and/or BCR/Abl. Examples of such compounds include, but are not limited to, Imatinib, Dasatinib, Nilotinib, Bosutinib, Bafetinib and Ponatinib. Further suitable examples are pyrazolo[3,4-d]pyrimidines, which are c-Src and c-Abl/BCR-Abl dual kinase inhibitors.

In the methods and uses described in this document an additional compound may be employed, for example a further compound that inhibits the function of protein kinases. Examples of low molecular weight compounds that have been reported to inhibit the function of protein kinases include, but are not limited to, bis monocyclic, bicyclic or heterocyclic aryl compounds (PCT WO 92/20642, published Nov. 26, 1992 by Maguire et al.), vinylene-azaindole derivatives (PCT WO 94/14808, published Jul. 7, 1994 by Ballinari et al.), 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT WO 94/03427, published Feb. 17, 1994 by Denny et al.), tricyclic polyhydroxylic compounds (PCT WO 92/21660, published Dec. 10, 1992 by Dow), and benzylphosphonic acid compounds (PCT WO 91/15495, published Oct. 17, 1991 by Dow et al).

Other examples of substances capable of modulating kinase activity include, but are not limited to, indolinones, tyrphostins, quinazolines, quinoxolines, and quinolines. The indolinones, quinazolines, tyrphostins, quinolines, and quinoxolines referred to above include well known compounds described in the literature.

A further example of a compound with may be used in conjunction with a peptide, peptidomimetic or combination, method or use disclosed herein is an anti-hormonal agent that acts to regulate, reduce, block, or inhibit the effects of hormones that can promote the growth of cancer. Such compounds are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY1 17018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMET A® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above. A "growth inhibitory agent" when used herein refers to a compound or composition which inhibits growth of a cell, especially a cancer cell, either in vitro or in vivo. Thus, the growth inhibitory agent may be one, which significantly reduces the percentage of such cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. The taxanes (paclitaxel and docetaxel) are anticancer drugs both derived from the yew tree. Docetaxel (TAXOTERE®), derived from the European yew, is a semisynthetic analogue of paclitaxel (TAXOL®). Paclitaxel and docetaxel promote the assembly of microtubules from tubulin dimers and stabilize microtubules by preventing depolymerization, which results in the inhibition of mitosis in cells.

In one aspect there is provided a method of identifying a peptide or peptidomimetic combination that is able to inhibit the kinase activity of a BCR-ABL protein and/or a c-ABL protein. The method includes providing a peptide or peptidomimetic that includes or consists of the sequence of SEQ ID NO: 1 or a homolog thereof. The method also includes providing a peptide or peptidomimetic that includes or consists of the sequence of SEQ ID NO: 2. The method may further include providing yet a further peptide or peptidomimetic, which is suspected to assist in and/or enhance inhibiting the kinase activity of a BCR-ABL protein and/or the c-ABL protein. In some embodiments the peptide or peptidomimetic that includes or consists of the sequence of SEQ ID NO: 1 or a homolog thereof and the peptide or peptidomimetic that includes or consists of the sequence of SEQ ID NO: 2 are encompassed by a common peptide or peptidomimetic or a common peptide/peptidomimetic hybrid. In some embodiments the peptide or peptidomimetic that includes or consists of the sequence of SEQ ID NO: 1 or a homolog thereof and the peptide or peptidomimetic suspected to assist in and/or enhance inhibiting the kinase activity of a BCR-ABL protein and/or the c-ABL protein are encompassed by a common peptide or peptidomimetic or a common peptide/peptidomimetic hybrid. In some embodiments the peptide or peptidomimetic that includes or consists of the sequence of SEQ ID NO: 2 and the peptide or peptidomimetic suspected to assist in and/or enhance inhibiting the kinase activity of a BCR-ABL protein and/or a c-ABL protein are encompassed by a common peptide or peptidomimetic or a common peptide/peptidomimetic hybrid.

The method further includes providing a target organism or target cell that expresses the BCR-ABL protein and/or the c-ABL protein. The target organism may be a microorganism or an animal, such as a mammal. The method also includes introducing the peptide and/or peptidomimetic combination into the target organism. In embodiments where the peptide or peptidomimetic that includes or consists of the sequence of SEQ ID NO: 1 or a homolog thereof, the peptide or peptidomimetic that includes or consists of the sequence of SEQ ID NO: 2 and, where applicable, the peptide or peptidomimetic suspected to assist in/enhance inhibiting the kinase activity of a BCR-ABL protein and/or c-ABL protein are encompassed by separate peptides or peptidomimetics, they may be introduced into the target cell or organism independently. In some of these embodiments all three peptides or peptidomimetics are introduced into the target cell or organism essentially simultaneously, including entirely simultaneously. In some embodiments introducing a peptide that includes or consists of the sequence of SEQ ID NO: 1 or a homolog thereof into a target cell, including a cell of a target organism such as a mammal, includes introducing a nucleic acid molecule into the respective cell. The nucleic acid molecule encodes the peptide that includes or consists of the sequence of SEQ ID NO: 1 or a homolog thereof. In some embodiments introducing a peptide that includes or consists of the sequence of SEQ ID NO: 2 into a target cell, including a cell of a target organism such as a mammal, includes introducing a nucleic acid molecule into the respective cell. The nucleic acid molecule encodes the peptide that includes or consists of the sequence of SEQ ID NO: 2. In some embodiments introducing a peptide suspected to assist in and/or enhance inhibiting the kinase activity of a BCR-ABL protein and/or a c-ABL protein includes introducing a nucleic acid molecule into the respective cell. The nucleic acid molecule encodes the peptide suspected to assist in and/or enhance inhibiting the kinase activity of the BCR-ABL protein and/or the c-ABL protein. As indicated above, a nucleic acid molecule introduced into the target cell or target organism may encode a peptide that includes both the sequence of SEQ ID NO: 1 or a homolog thereof and the sequence of SEQ ID NO: 2. Where applicable, such a peptide encoded by a respective nucleic acid molecule may also include a peptide suspected to assist in and/or enhance inhibiting the kinase activity of the BCR-ABL protein and/or the c-ABL protein.

The method further includes measuring the kinase activity of the BCR-ABL protein and/or the c-ABL protein of the target organism or target cell. The present method may furthermore include comparing the results of measuring the kinase activity of the BCR-ABL protein and/or the c-ABL protein with results of a control measurement (or "reference" measurement). A control measurement may include the use of conditions that do not modulate the protein kinase activity of the BCR-ABL protein and/or the c-ABL protein. In comparing activity, detected levels may for example be compared to a control level. The term "control level" as used herein refers to an activity level of a BCR-ABL protein and/or the c-ABL protein in a control sample. The term thus includes both a normal control level and a cancer control level. The term can refer to a single reference measurement or to a plurality of reference measurements. In some embodiments the control level may be a database of expression or activity values from previously conducted measurements. The term "customary level" refers to an activity level of a c-ABL protein detected in a normal, healthy individual or in a population of individuals known not to be suffering from a neoplasm, including cancer. A normal individual is one with no clinical symptoms of a respective neoplasm.

In one aspect there is provided a method of identifying a peptide or peptidomimetic combination that is able to inhibit the kinase activity of a BCR-ABL protein and/or a c-ABL protein to a higher degree when compared to a combination of a peptide or peptidomimetic that includes the sequence of SEQ ID NO: 1 and a peptide or peptidomimetic that includes the sequence of SEQ ID NO: 2. In such a method a control measurement a combination of a peptide or peptidomimetic that includes the sequence of SEQ ID NO: 1 and a peptide or peptidomimetic that includes the sequence of SEQ ID NO: 2 Where desired a peptide or peptidomimetic combination is to be identified that is able to inhibit the kinase activity of a BCR-ABL protein and/or a c-ABL protein to a higher degree when compared to a combination of a peptide or peptidomimetic that includes the sequence of a homolog of SEQ ID NO: 1 and a peptide or peptidomimetic that includes the sequence of SEQ ID NO: 2. The latter combination, i.e. a combination of a peptide or peptidomimetic that includes the sequence of a homolog of SEQ ID NO: 1 and a peptide or peptidomimetic that includes the sequence of SEQ ID NO: 2 can serve as a control or reference measurement in such an embodiment.

As used herein, an activity level is deemed to be "altered" or to "differ" when activity is increased or decreased by about 10%, about 25%, about 50%, about 75%, about 100%, or higher, as compared to the control level. Alternatively, an activity level is deemed "increased" or "decreased" when an activity is increased or decreased by at least about 0.1, at least about 0.2, at least about 1, at least about 2, at least about 5, or at least about 10 or more fold as compared to a control level.

The peptide, peptidomimetic or combination described herein, as well as a peptide, peptidomimetic or combination identified by a method disclosed herein, can be administered to a cell, an animal or a human patient per se, or in pharmaceutical compositions where they are mixed with other active ingredients, as in combination therapy, or suitable carriers or excipient(s), including stabilizers. Such carriers, excipients or stabilizers are usually pharmaceutically acceptable in that they are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®. Exemplary routes include, but are not limited to, oral, transdermal, and parenteral delivery.

Suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the peptide, peptidomimetic or combination in a local rather than systemic manner, for example, via injection of the peptide, peptidomimetic or combination directly into a solid tumor, often in a depot or sustained release formulation.

Furthermore, one may administer the drug in a targeted drug delivery system, for example, in a liposome coated with a tumour-specific antibody. The liposomes will be targeted to and taken up selectively by the tumour.

A pharmaceutical composition as disclosed herein includes a peptide, peptidomimetic or combination as defined above. Such a pharmaceutical composition may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with a method disclosed herein thus may be formulated in conventional manner using one or more physiologically acceptable carriers including excipients and auxiliaries that facilitate processing of the active peptide, peptidomimetic or combination into preparations that can be used pharmaceutically. Proper formulation is dependent upon the route of administration chosen.

For injection, the agents disclosed herein may be formulated in aqueous solutions, for instance in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the peptide, peptidomimetic or combination can be formulated readily by combining the peptide, peptidomimetic or combination with pharmaceutically acceptable carriers well known in the art. Such carriers enable the peptide, peptidomimetic or combination disclosed herein to be formulated as a tablet, pills, dragee, capsule, liquid, gel, syrup, slurry or suspension, for oral ingestion by a patient to be treated.

Pharmaceutical preparations for oral use can be obtained by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active peptide, peptidomimetic or combination doses.

Pharmaceutical preparations that can be used orally include push-fit capsules made of gelatine, as well as soft, sealed capsules made of gelatine and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active peptide, peptidomimetic or combination may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the peptide, peptidomimetic or combination for use disclosed herein is conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatine for use in an inhaler or insufflator may be formulated containing a powder mix of the peptide, peptidomimetic or combination and a suitable powder base such as lactose or starch.

The peptide, peptidomimetic or combination may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active peptide, peptidomimetic or combination in water-soluble form. Additionally, a suspension of the active peptide, peptidomimetic or combination may be prepared as an appropriate oily injection suspension. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the peptide, peptidomimetic or combination to allow for the preparation of highly concentrated solutions.

Alternatively, the active ingredient may be in powder form for constitution with a suitable vehicle, e.g., sterile pyrogen-free water, before use. The peptide, peptidomimetic or combination may also be formulated in rectal compositions such as suppositories or retention enemas, e.g., containing conventional suppository bases such as cocoa butter or other glycerides.

In addition to the formulations described previously, the peptide, peptidomimetic or combination may also be formulated as a depot preparation. Such long acting formulations may be administered by implantation (for example subcutaneously or intramuscularly) or by intramuscular injection. Thus, for example, the peptide, peptidomimetic or combination may be formulated with suitable polymeric or hydrophobic materials (for example, as an emulsion in an acceptable oil) or ion exchange resins, or as sparingly soluble derivatives, for example, as a sparingly soluble salt.

A pharmaceutical carrier for a hydrophobic peptide, peptidomimetic or combination disclosed herein is a co-solvent system including benzyl alcohol, a non-polar surfactant, a water-miscible organic polymer, and an aqueous phase. The co-solvent system may be the VPD co-solvent system. VPD is a solution of 3% w/v benzyl alcohol, 8% w/v of the non-polar surfactant polysorbate 80, and 65% w/v polyethylene glycol 300, made up to volume in absolute ethanol. The VPD co-solvent system (VPD:D5W) consists of VPD diluted 1:1 with a 5% dextrose in water solution.

This co-solvent system dissolves hydrophobic peptide, peptidomimetic or combination well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity non-polar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Other delivery systems for hydrophobic pharmaceutical compounds may also be employed. Liposomes and emulsions are well known examples of delivery vehicles or carriers for hydrophobic drugs. Certain organic solvents such as dimethylsulfoxide also may be employed, although usually at the cost of greater toxicity. Additionally, the peptide, peptidomimetic or combination may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the peptide, peptidomimetic or combination for a few weeks up to over 100 days. Depending on the chemical nature and the biological stability of the therapeutic reagent, additional strategies for protein stabilization may be employed.

The pharmaceutical compositions also may include suitable solid or gel phase carriers or excipients.

Examples of such carriers or excipients include but are not limited to calcium carbonate, calcium phosphate, various sugars, starches, cellulose derivatives, gelatine, and polymers such as polyethylene glycols.

Many of the compounds that may be used in a method or use disclosed herein may be provided as salts with pharmaceutically compatible counter-ions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

Pharmaceutical compositions suitable for use as disclosed herein include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided in this document.

For any compound used in the methods disclosed herein, the therapeutically effective dose can be estimated initially from cell culture assays. For example, a dose can be formulated in animal models to achieve a circulating concentration range that includes the IC50 as determined in cell culture (i.e., the concentration of the test compound which achieves a half-maximal inhibition of the kinase activity).

Such information can be used to more accurately determine useful doses in humans.

Toxicity and therapeutic efficacy of the peptide, peptidomimetic or combination described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. It may be desired to use peptide, peptidomimetic or combination that exhibit high therapeutic indices. The data obtained from these cell culture assays and animal studies can be used in formulating a range of dosage for use in humans. The dosage of such peptide, peptidomimetic or combination lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition.

Dosage amount and interval may be adjusted individually to provide plasma levels of the active moiety, which are sufficient to maintain the kinase modulating effects, or minimal effective concentration (MEC). The MEC will vary for each peptide, peptidomimetic or combination but can be estimated from in vitro data; e.g., the concentration necessary to achieve 50-90% inhibition of the kinase. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen that maintains plasma levels above the MEC for 10-90% of the time, for example from about 30 to about 90%, such as from about 50 to about 90%. In cases of local administration or selective uptake, the effective local concentration of the drug may not be related to plasma concentration. The amount of composition administered will, of course, be dependent on the subject being treated, on the subject's weight, the severity of the affliction, the manner of administration and the judgment of the prescribing physician.

The compositions may, if desired, be presented in a pack or dispenser device, which may contain one or more unit dosage forms containing the active ingredient. The pack may for instance include metal or plastic foil, such as a blister pack. The pack or dispenser device may be accompanied by instructions for administration. The pack or dispenser may also be accompanied with a notice associated with the container in a form prescribed by a governmental agency regulating the manufacture, use, or sale of pharmaceuticals, which notice is reflective of approval by the agency of the form of the compound for human or veterinary administration. Such notice, for example, may be the labelling approved by the U.S. Food and Drug Administration or other government agency for prescription drugs, or the approved product insert.

Compositions disclosed herein formulated in a compatible pharmaceutical carrier may also be prepared, placed in an appropriate container, and labelled for treatment of an indicated condition. Suitable conditions indicated on the label may include, for example, treatment of cancer.

As explained above, the present invention encompasses the diagnostic, prognostic, and therapeutic use of a peptidomimetic, or a combination of peptides or peptidomimetics capable of binding to and modulating the activity of c-Abl and/or BCR-Abl in a cell. Based on the inventors' findings the invention also provides methods of identifying a peptide, peptidomimetic or combination that is capable of preventing, inhibiting, arresting or reversing tumourigenesis, including carcinogenesis, in a cell and/or of inducing apoptosis in a tumour cell. Some of these methods are in vivo or ex vivo methods. Some of the methods are in-vitro methods of identifying a respective peptide, peptidomimetic or combination.

The contents of the articles, patents, and patent applications, and all other documents and electronically available information mentioned or cited herein, are hereby incorporated by reference in their entirety to the same extent as if each individual publication was specifically and individually indicated to be incorporated by reference. In case of conflict, the present specification, including definitions, will control. Applicants reserve the right to physically incorporate into this application any and all materials and information from any such articles, patents, patent applications, or other physical and electronic documents.

The listing or discussion of a previously published document in this specification should not necessarily be taken as an acknowledgement that the document is part of the state of the art or is common general knowledge.

The methods, uses and combinations illustratively described herein may suitably be practiced and applied in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The terms "comprising", "including, "containing", "having" etc. shall be read expansively or open-ended and without limitation. Thus the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the word "having". When used herein "consisting of" excludes any element, step, or ingredient not specified in the defined element, e.g. claim element. When used herein, "consisting essentially of" does not exclude materials or steps that do not materially affect the basic and novel characteristics of the respective definition or claim.

Singular forms such as "a", "an" or "the" include plural references unless the context clearly indicates otherwise. Thus, for example, reference to a "vector" includes a single vector as well as a plurality of vectors, either the same—e.g. the same operon—or different. Likewise reference to a "cell" includes a single cell as well as a plurality of cells. Unless otherwise indicated, the term "at least" preceding a series of elements is to be understood to refer to every element in the series. The terms "at least one" and "at least one of" include for example, one, two, or more elements. It is furthermore understood that slight variations above and below a stated range can be used to achieve substantially the same results as a value within the range. Also, unless indicated otherwise, the disclosure of ranges is intended as a continuous range including every value between the minimum and maximum values.

The invention has been described broadly and generically herein. Each of the narrower species and subgeneric groupings falling within the generic disclosure also form part of the methods, uses and combinations. This includes the generic description of the methods, uses and combinations with a proviso or negative limitation removing any subject matter from the genus, regardless of whether or not the excised material is specifically recited herein.

Other embodiments are set forth within the appending claims. In addition, where features or aspects of the invention are described in terms of Markush groups, those skilled in the art will recognize that the invention is also thereby described in terms of any individual member or subgroup of members of the Markush group.

The invention is further illustrated by the following non limiting examples and the appended figures. As one of ordinary skill in the art will readily appreciate from the present disclosure, other compositions of matter, means, uses, methods, or steps, presently existing or later to be developed that perform substantially the same function or achieve substantially the same result as the corresponding exemplary embodiments described herein may likewise be utilized according to the present invention.

EXAMPLES

The appended data illustrate that the NS1 protein in general binds to c-Abl and NS1 proteins possessing the SH3(II)bm consensus block c-Abl kinase activity. Chemical inhibition of c-Abl attenuated virus growth of avian IAV. While mutational disruption of the SH3(II)bm increased virus titers of avian IAV, reconstitution of the SH3(II)bm in a H5N1 strain resulted in reduced viral propagation thereby linking inhibition of c-Abl to growth disadvantages. Finally, the ability of avian IAV to block c-Abl kinase activity correlates with the induction of a strong cytopathogenic effect (CPE) that was diminished after loss of the SH3(II)bm consensus sequence.

CRK Adaptor Protein Phosphorylation is Strongly Reduced Upon Prototype Avian IAV Infection As demonstrated recently CRK adaptor proteins bind to NS1 of prototype avian IAV in contrast to NS1 of common human IAV (Heikkinen et al., 2008, supra; Hrincius et al., 2010, supra). Binding of NS1 to CRK proteins is mediated by the SH3(II)bm of avian strains while NS1 of human IAV do not carry the SH3(II)bm.

As starting point of our current study, we examined whether the presence or absence of a functional SH3(II)bm within avian and human NS1 proteins, respectively, might influence the activities of CRK adaptor proteins and/or CRK regulated signalling networks. Posttranscriptional regulation of the CRK proteins by phosphorylation has previously been identified as a regulatory mechanism for signalling networks. The non-receptor tyrosine kinase c-Abl was identified as a major mediator of CRK protein phosphorylation (de Jong, R., et al., Oncogene (1997) 14, 507-513; Feller, S. M., et al., EMBO J (1994) 13, 2341-2351) and thereby regulates these signalling networks.

Figure 2C:
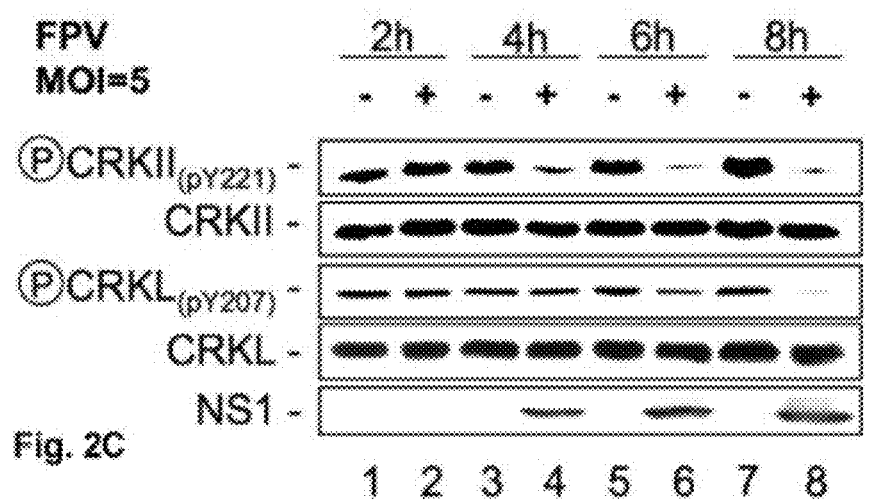
Figure 2D:
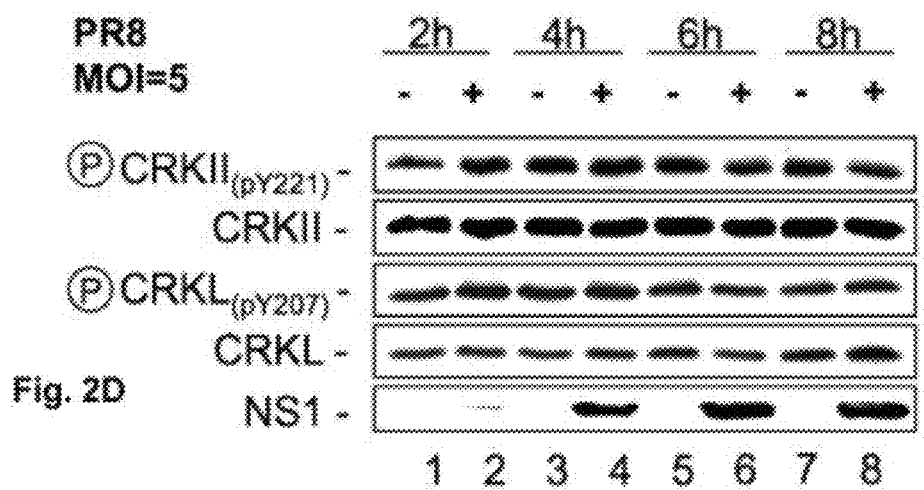

The capacious impact of CRK proteins and c-Abl on cellular signaling prompted us to examine the phosphorylation status of CRK adaptor protein family members and furthermore to focus on the role of c-Abl in IAV-infected host cells. For investigation of the overall phosphorylation status of CRKL, we immunoprecipitated CRKL from A549 human lung epithelial cell lysates that were infected with prototype avian IAV (FPV) or human IAV (PR8). As shown earlier, CRKL selectively co-immunoprecipitated with avian NS1 (FIG. 2A) due to the differences in the SH3(II)bm consensus sequence (Hrincius et al., 2010, supra). CRK proteins exhibit a basal phosphorylation in living cells (Feller, S. M., Oncogene (2001) 20, 6348-6371). From the present data it can be inferred that the basal tyrosine phosphorylation of the precipitated CRKL was clearly reduced in cells infected with the prototypic avian strain FPV, in clear contrast to human PR8 virus-infected or uninfected cells (FIG. 2A). This pattern was also confirmed with an antibody that detects the phosphorylation of CRKL at tyrosine residue 207, a site targeted by c-Abl (Senechal, K., et al., Mol Cell Biol (1998) 5082-5090; de Jong et al., 1997, supra) (FIG. 2B). Infection kinetics in A549 cells further revealed reduced CRKL (Y207)—as well as CRKII (Y221) phosphorylation upon FPV infection in contrast to PR8 infection (FIG. 2C). This result clearly illustrates that infection with the avian FPV strain suppresses the phosphorylation of different CRK adaptor proteins arguing for a broad mechanism of action. Additionally, the reduction of CRK phosphorylation in FPV infected cells correlated with the kinetics of NS1 expression, linking the inhibition of CRK protein phosphorylation to the time course of NS1 accumulation (FIG. 2C, 2E, 2G). The analyses of two other epithelial cell lines—Madin-Darby canine kidney cells (MDCK) and human embryonic kidney cells (293)—clearly illustrates a cell type independent reduction of the CRKL and CRKII phosphorylation upon avian FPV infection (FIGS. 2E and 2G), which could not be observed after infection with human PR8 (FIGS. 2F and 2H).

Prototype Avian IAV Infection Results in Inhibition of c-Abl Kinase Activity The observation that Y207 in CRKL and Y221 of CRKII, both known to be targeted by c-Abl (de Jong et al., 1997, supra; Feller et al., 1994, supra), were underphosphorylated in avian virus infected cells suggested a reduction in c-Abl kinase activity. To investigate this assumption the inventors immunoprecipitated c-Abl from lysates of infected or uninfected cells and subsequently subjected it to an in vitro immunocomplex kinase assay using MBP as a substrate. These experiments revealed a clear reduction of c-Abl kinase activity in FPV infected cells in contrast to PR8 infected or uninfected cells (FIG. 3).

The SH3(II)Bm within the NS1 Protein is Necessary for c-Abl Kinase Inhibition The data shown so far indicated that the presence of a functional SH3(II)bm within the NS1 protein could be directly involved in the ability to inhibit c-Abl kinase activity. As mentioned earlier, prototype avian IAV like FPV encode for a SH3(II)bm whereas human IAV such as PR8 do not express this motif as shown earlier (Heikkinen et al., 2008, supra; Hrincius et al., 2010, supra). To exclude that any other differences in the entire virus genome between FPV and PR8 may affect the ability to interfere with c-Abl kinase activity, we used a different virus background and compared the avian-like strain SC35M expressing NS1 with the SH3(II)bm ($_{212}$PPLPPK$_{217}$) with a variant containing the P215T mutation (SC35M P215T) in the SH3bm consensus ($_{212}$PPLTPK$_{217}$). This single point mutation P215T disrupted the SH3bm consensus sequence and prevented co-immunoprecipitation of NS1 with CRK (FIG. 4A). Accordingly, the mutant virus did not affect c-Abl kinase activity (FIGS. 4B and 4C), while SC35M wt infection readily down-regulated kinase activity as measured by CRKL and CRKII phosphorylation (FIG. 4B) and in an in vitro kinase assay (FIG. 4C). This clearly shows that the SH3(II)bm within NS1 is crucial for c-Abl kinase inhibition.

Interestingly, almost all NS1 proteins of human H5N1 isolates do not encode the SH3(II)bm consensus. This prompted an investigation as to whether a wild-type H5N1 isolate, encoding no SH3(II)bm, would affect c-Abl kinase activity and whether restoration of the SH3(II)bm consensus within NS1 would revert that phenotype. The inventors used a reverse genetic system for the H5N1 isolate KAN-1 and rescued the KAN-1 wt and a KAN-1 NS1 L207P N212K (KAN-1 L207P N212K) virus mutant. The presence of the SH3(II)bm consensus sequence in the KAN-1 mutant NS1 L207P N212K was confirmed by NS1-CRK interaction studies (FIG. 5A). CRKL and CRKII phosphorylation were measured as an indicator for c-Abl kinase activity in infected A549 cells. The analysis verified that infection with wild-type KAN-1 did not suppress c-Abl kinase activity (FIG. 5B), while introduction of a SH3(II)bm in the H5N1 virus mutant results in a clearly reduced c-Abl kinase activity (FIG. 5B). In line with the previous findings, restoration of the SH3(II)bm consensus in the NS1 protein of human PR8 virus enabled binding to CRK (FIG. 5C) and partial repression of c-Abl kinase activity (FIG. 5D). This finding illustrates that human IAV have a cryptic potential to interfere with c-Abl kinase activity if a functional SH3(II)bm is provided (FIG. 5D). Taken together, we could demonstrate for the first time that IAV viruses are able to interfere with the activity of the non-receptor tyrosine kinase c-Abl mediated by the presence of the SH3(II)bm within NS1.

The NS1 Protein of IAV Directly Binds to c-Abl Independently of the SH3(II)bm

Several previous studies have analyzed the mechanism by which c-Abl kinase activity is regulated (Chen, S., et al., Protein Sci (2007) 16, 572-581; Barila, D., and Superti-Furga, G., Nat Genet (1998) 18, 280-282; Van Etten, R. A., et al., Oncogene (1995) 10, 1977-1988; Dubey, K. D., and Ojha, R. P., J Mol Model (2011) 18, 1679-1689; Sirvent et al., 2008, supra). Interestingly, the CRK proteins bind to c-Abl (Feller et al., 1994, supra; Ren, R., et al., Genes Dev (1994) 8, 783-795) and especially CRKII has been identified as a transactivator of c-Abl by initial binding of the CRKII N-terminal SH3 domain to the proline-rich motif in c-Abl (Reichman, C., et al., Oncogene (2005) 24, 8187-8199).

Interestingly, this CRKII N-terminal SH3 domain is also the binding site for NS1 (Heikkinen et al., 2008). Therefore, we asked whether the binding of avian NS1 to CRKII might be able to interfere with the CRK-c-Abl interaction thereby resulting in reduced kinase activity observed after prototype avian IAV infection (FIG. 3 to FIG. 5). Investigating the CRK binding to c-Abl indeed revealed that infection with a prototype avian IAV impaired CRK-c-Abl interaction (FIG. 11A).

It has been previously shown that NS1 of IAV mediates its various functions by direct binding to different host cell factors (e.g. Heikkinen et al., 2008, supra; Hrincius et al., 2010, supra; Hale, B. G., et al., Proc Natl Acad Sci USA (2006) 103, 14194-14199; Hale et al., J Gen Virol, 2008, supra; Gack, M. U., et al., Cell Host Microbe (2009) 5, 439-449; Li, S., et al., Virology (2006) 349, 13-21; Lee, J. H., et al., Virology (2010) 397, 89-99). Since NS1 was able to block c-Abl kinase activity and the SH3(II)bm consensus sequence within NS1 was crucial for c-Abl inhibition, we examined a putative interaction of NS1 and c-Abl as mechanism of action. In a c-Abl pull-down assay we could indeed demonstrate co-precipitation of NS1 with c-Abl (FIGS. 6A and 6B) thereby identifying a so far unknown interaction partner of the NS1 protein. Interestingly, the NS1 proteins of both, avian (FIG. 6A) and human IAV (FIG. 6B) co-precipitated with c-Abl illustrating that binding of NS1 to c-Abl can be separated from the capability to inhibit c-Abl kinase activity.

Figure 6E:
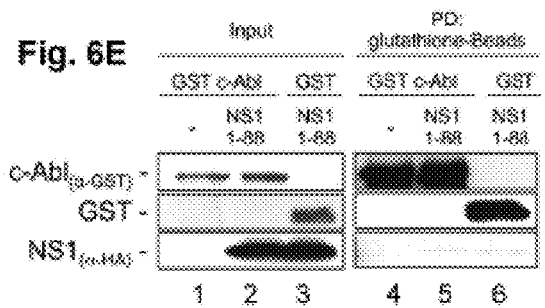

In an attempt to narrow down the c-Abl binding motif within NS1 the inventors investigated binding of C-terminal truncated NS1 versions to c-Abl. Full-length NS1 (aa1-230) of the human IAV PR8 interacted with c-Abl (FIG. 6C), again demonstrating binding of NS1 to c-Abl and confirming the independence of NS1 c-Abl interaction from the SH3(II)bm. Interestingly, a truncated version of NS1 (aa1-125) had maintained the ability to bind to c-Abl (FIG. 6D), but further truncation (NS1 aa1-88) resulted in loss of this interaction (FIG. 6E).

Figure 6F:
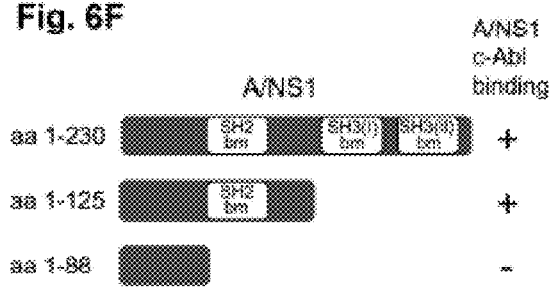
FIG. 6F: A schematic representation of the depicted results is shown. On the right panel, binding capacity of the different NS1 proteins is demonstrated by plus and minus symbols.

Taken these data together, the inventors identified c-Abl as a new NS1 interaction partner. Although c-Abl kinase inhibition by NS1 was dependent on the intact SH3(II)bm, initial interaction of NS1 with c-Abl was independent, showing that c-Abl binding and kinase inhibition by NS1 represent separate processes. Furthermore, the crucial NS1 motif responsible for c-Abl interaction was localized to aa88-125 (FIG. 6F).

Figure 7A:
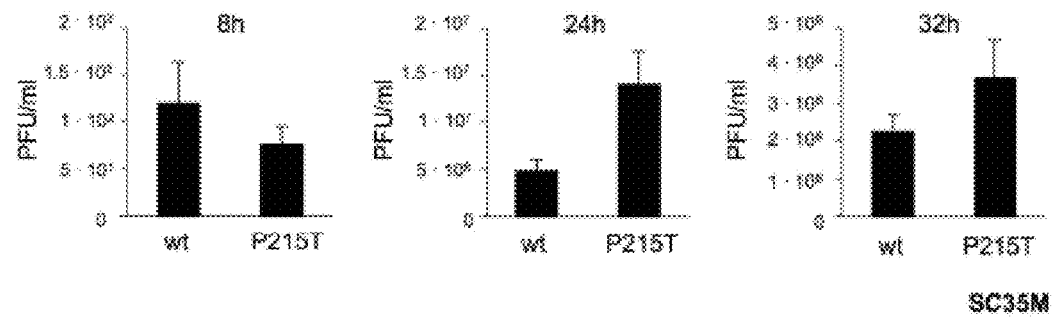
FIG. 7. Ongoing replication of avian IAV encoding an SH3(II)bm within NS1 is impaired. A549 cells were infected with the rec. avian IAV SC35M wt or SC35M P215T (A) (MOI=0.001), the rec. H5N1 IAV KAN-1 wt or KAN-1 L207P/N212K (B) (MOI=0.01) and the rec. human IAV PR8 wt or rec. PR8 T215P (C) (MOI=0.5). Supernatants were assayed for progeny virus yields 8 h, 24 h and 32 h p.i. in standard plaque titrations. Virus yields are depicted in PFU/ml. Representative results of at least three independent experiments are depicted and statistical significance of the differences were determined by students t-test (A, 8 h n.s., 24 h p<0.05 and 32 h p<0.05 and B, 8 h n.s., 24 h p<0.05 and 32 h p<0.05).
Figure 7B:
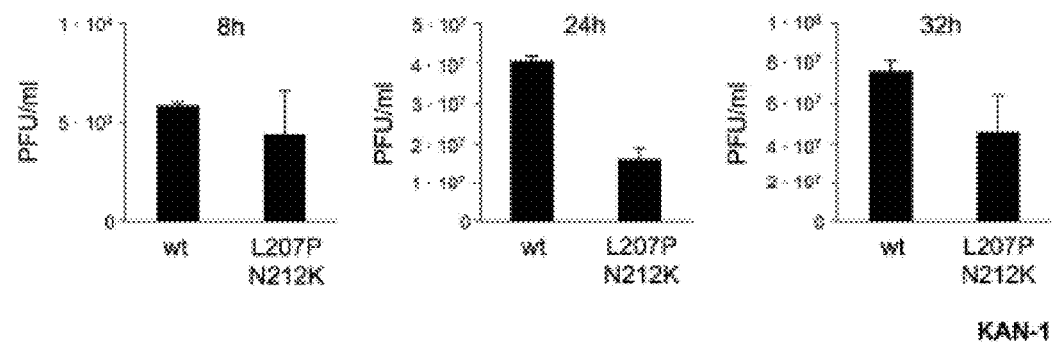
Figure 7C:
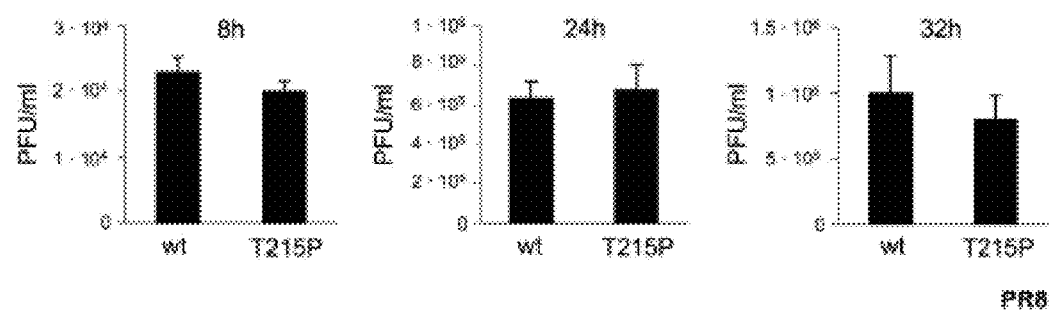

Avian IAV not Carrying a SH3(II)Bm within NS1 Show an Increased Replication Ability in Human Lung Epithelial Cells After demonstrating the impact of the SH3(II)bm within avian NS1 proteins on inhibition of c-Abl kinase activity, the inventors aimed to determine how this motif would affect the replication of IAV. Therefore, they compared progeny virus titers of IAV SC35M wt—being able to inhibit c-Abl kinase activity—and of IAV SC35M P215T—lacking the ability to inhibit c-Abl. These experiments revealed that avian viruses lacking the SH3(II)bm replicate more efficient (FIG. 7A). This result was further confirmed in a mutational approach with the avian strain A/FPV/Rostock/34 (H7N1) (FPV-Rostock) (data not shown) and in the reverse experiment by restoration of the SH3(II)bm consensus sequence in the NS1 of H5N1 KAN-1 IAV. KAN-1 wt IAV had evident growth advantages compared to the mutant KAN-1 L207P N212K (FIG. 7B), again clearly showing that avian IAV replicate less efficiently in the presence of the NS1 SH3(II)bm. The obtained data were confirmed using chicken DF1 cells showing that the here depicted phenomenon was host cell independent (data not shown). Against it, an impact of the SH3(II)bm within NS1 on replication of human IAV was not detectable (FIG. 7C).

Taken together, it could be clarified that avian IAV encoding an NS1 without SH3(II)bm consensus show propagation advantages compared to avian viruses possessing an NS1 with the SH3(II)bm.

Chemical Inhibition of c-Abl Impairs Propagation of Avian IAV

Figure 8A:
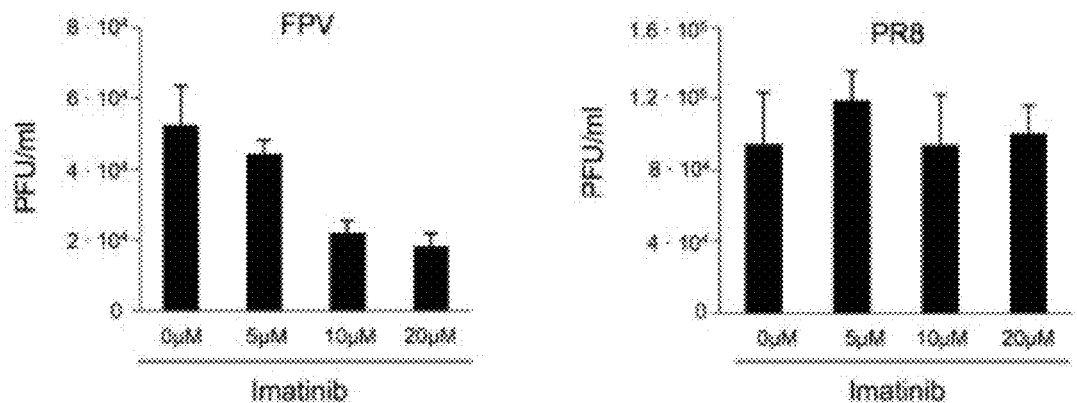
FIG. 8. Chemical inhibition of c-Abl impairs replication of avian IAV. A-D: A549 cells were infected with the avian IAV FPV (MOI=0.01: A left panel, B leftmost and C) (MOI=5: (B left panel and C), the human IAV PR8 (MOI=0.5: A right panel, B right panel and C) (MOI=5: B rightmost and C) or with the rec. avian IAV SC35M wt or SC35M P215T (D) (MOI=5). Directly upon infection, cells were incubated with 5-20 µM Imatinib or were left untreated. 8 h p.i. supernatants were collected and assayed for progeny virus yields in standard plaque titrations (A, B and D). Virus yields are depicted in PFU/ml. Cells were lysed 8 h p.i. and lysates were used for Western Blot (C). Phosphorylated CRKII (pY221) was detected via a specific antibody. Viral protein expression was visualized by specific antibodies against NS1 and NP. Detection of CRKII and ERK2 served as loading controls. Representative results of at least three independent experiments are depicted (A, B) and statistical significance of the differences were determined by students t-test (A: FPV between 0 µM and 5 µM n.s., between 0 µM and 10 µM p<0.05, between 0 µM and 20 µM p<0.05 and B: FPV MOI=0.01 between 0 µM and 20 µM p<0.05). D: Mean results of three independent experiments are depicted and statistical significance of the differences were determined by students t-test (* p<0.05).
Figure 8B:
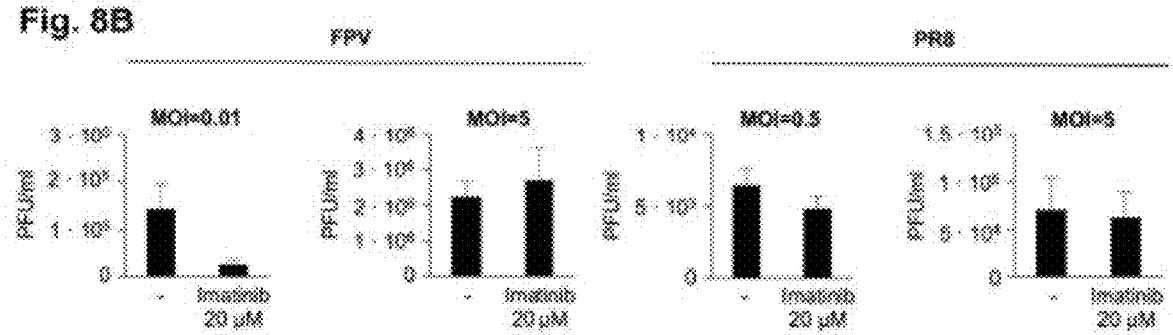
Figure 8C:
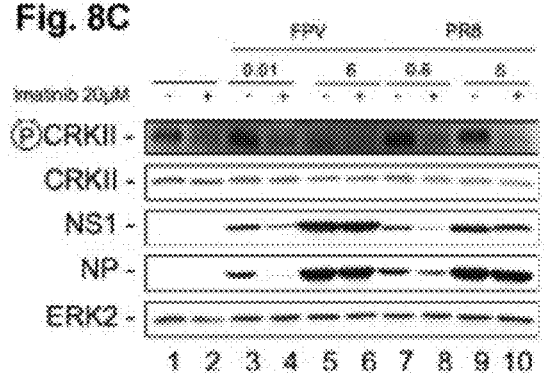
Figure 8D:
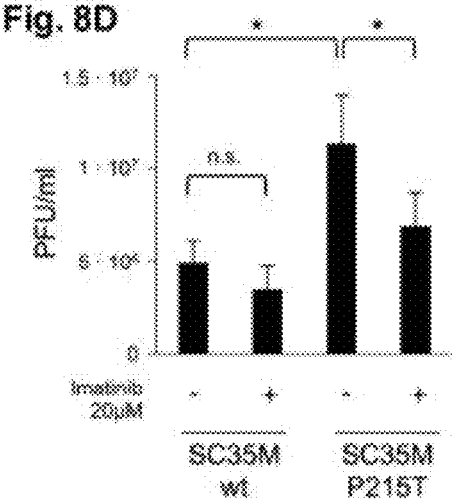

Prototype avian IAV, able to block c-Abl kinase activity, showed decreased replication capability. This combination of c-Abl inhibition and growth disadvantages prompted us to examine a possible link between c-Abl inhibition and efficiency of virus growth. Treatment of A549 cells with the c-Abl inhibitor Imatinib after infection with a low MOI revealed that c-Abl inhibition indeed interferes with replication properties of the avian IAV FPV in a concentration dependent manner (FIG. 8A, left panel and FIG. 8B leftmost panel). However, Imatinib treatment was only efficient upon low dose infection (FIG. 8B, left panel), probably due to accumulation of high NS1 levels and strong inhibition of c-Abl by the virus itself upon infection with higher virus amounts (FIG. 8C). In strong contrast, replication of the human IAV PR8 was absolutely independent of the tyrosine kinase activity of c-Abl regardless whether low (FIG. 8A, right panel and FIG. 8B, right panel) or high MOI (FIG. 8B, rightmost panel) were used for infection. These results demonstrate that inhibition of c-Abl affects the replication ability of avian IAV and furthermore denote a link between NS1 mediated inhibition of c-Abl and efficiency of virus growth. A time of addition kinetic revealed similar reductions of virus titers even when Imatinib was added four to six hours post infection (FIG. 12A). This excludes an early step in IAV life cycle to be affected by c-Abl inhibition. Finally, the inventors addressed whether the growth advantages of avian viruses with a disrupted SH3(II)bm could be converted by chemical inhibition of c-Abl. Infection with SC35M P215T using a high MOI (MOI=5) led to higher titers than SC35M wt infection, showing that the wt virus with c-Abl inhibiting properties replicates less well. The growth advantage of the SC35M P215T was abrogated by chemical inhibition of c-Abl resulting in similar virus titers to SC35M wt (FIG. 8D), clearly linking the ability of avian IAV to inhibit c-Abl to the respective growth disadvantages.

C-Abl Inhibiting Avian Influenza Viruses Cause a Severe Cytopathogenic Effect (CPE) in Epithelial Cells C-Abl is involved in plenty of cellular processes (Sirvent et al., 2008), such as cellular gene transcription (Baskaran, R., et al., Cell Growth Differ (1999) 10, 387-396) or the induction of the type I IFN response (Song et al., 2010, Katsoulidis et al., 2008). To elucidate the role of c-Abl in the control of IAV life cycle we examined a putative influence of c-Abl on the IAV polymerase activity, viral protein accumulation and type I IFN response. In summary, an impact of c-Abl on polymerase activity and viral protein accumulation was not detectable and furthermore, the induction of the type I IFN response was not affected by modulated c-Abl kinase activity (FIG. 13).

Additionally, Abl kinases fulfil important functions in actin reorganization (Sirvent, A., et al., Biol Cell (2008) 100, 617-631), evidenced by defects in the actin latticework upon Abl kinase knockout (Koleske et al., 1998). By being involved in F-actin organization, Abl is taken part in cellular processes such as regulation of cell adhesion or migration (Woodring, P. J., et al., J Cell Biol (2002) 156, 879-892; Woodring, P. J., et al., J Cell Sci (2003) 116, 2613-2626). Additionally, Abl tyrosine kinases are involved in the regulation and manifestation of cell-cell contacts (Zandy, N. L., et al., Proc Natl Acad Sci USA (2007) 104, 17686-17691; Zandy, N. L., et al., Cell Cycle (2008) 7, 444-448; Lu, M., and Krauss, R. S., Cell Cycle (2010) 9, 2737-2741). Therefore, cells were examined for the induction of a pathologically altered cell shape after infection with IAV differing in their ability to block c-Abl kinase activity as underlying mechanism of diminished virus production. Infection with the avian IAV FPV resulted in shrinking, rounding and partial detachment of infected cells (FIG. 9B), all together exhibiting a clear cytopathogenic effect (CPE) at 8 h post infection. In contrast, uninfected cells or human PR8 infected cells did not display these severe morphological alterations and were still well outstretched and attached. These data provide first evidence that the ability of IAV to block c-Abl could contribute to the severity of CPE. Accordingly, infection with the avian IAV SC35M wt resulted in a clear CPE (FIG. 9D), whereas the disruption of the c-Abl inhibitory potential in the NS1 P215T mutant virus completely impaired the induction of cytopathogenic cell alterations. Additionally, infection with the KAN-1 wt strain, a human H5N1 isolate that does not impair c-Abl kinase activity—did also not result in CPE, thus resembling infections with PR8 or SC35M P215T (FIG. 9C, 9E). In turn, restoration of the c-Abl inhibiting properties of KAN-1 NS1 resulted in cytopathogenic alterations almost comparable to FPV and SC35M wt infections. Finally, infection with the IAV PR8 rec. wt—lacking c-Abl inhibitory properties—and the IAV PR8 rec. T215P—causing only a slight inhibition of c-Abl kinase activity—did also not generate a CPE of infected cells (FIG. 9H, 9I). Taken these data together, an interplay of c-Abl inhibitory potential of IAV and the ability to drive pathogenic cell alterations like cell rounding, shrinking and partial detachment of infected cells could be shown. It was further confirmed in a second cell line using 293 cells (FIG. 14A-E) and again clearly illustrate the interplay of IAV induced c-Abl inhibition and cytopathogenic cell alterations (FIG. 14A-E, FIG. 14H).

To gain further insights into the functional link of IAV mediated c-Abl inhibition and deregulation of c-Abl functions in organizing cell shape or motility, the inventors monitored the c-Abl mediated phosphorylation of Wave 3, described as being essential for actin organization like e.g. lamellipodia formation (Sossey-Alaoui, K., et al., J Biol Chem (2007) 282, 26257-26265). 293 cells, which were infected with the avian IAV SC35M wt exhibited reduced Wave 3 phosphorylation in contrast to uninfected or SC35M P215T infected cells (FIG. 14G). Thus, by blocking c-Abl kinase activity, SH3(II)bm-bearing avian IAV impair c-Abl mediated functions of factors that are involved in regulation of actin cytoskeletal organization.

Taken together, c-Abl was identified as a new interaction partner of NS1 and it was shown that avian IAV that harbour a SH3(II)bm suppress c-Abl activity and c-Abl mediated regulation of factors involved in organization of cell shape. This interplay results in the induction of severe pathological cell modifications.

Discussion

The non-structural protein 1 (NS1) of influenza A viruses (IAV is known as a major pathogenicity determinant of IAV (Hale et al., J Gen Virol, 2008, supra) that executes its functions at least in part by binding to cellular proteins. Hence, its sequence displays a variety of interactive regions including several src homology binding motifs (one SH2bm and two SH3bm) (Ehrhardt et al., 2009, supra) that, however, are conserved to different degrees among virus strains. For instance, the SH3(II)bm and the C-terminal PDZ ligand domain that was linked to virulence regulation (Zielecki, F., et al., J Virol (2010) 84, 10708-10718; Soubies, S. M., et al., J Virol (2010) 84, 6733-6747; Jackson, D., et al., Proc Natl Acad Sci USA (2008) 105, 4381-4386) possess a different consensus sequence in NS1 proteins of avian and human virus strains (Hale et al., J Gen Virol, 2008, supra; Heikkinen et al., 2008, supra). A major challenge with avian influenza viruses is to understand the reasons underlying their zoonotic potential. Therefore, motifs with different human and avian signatures came into focus of interest. The fact that H5N1 strains and especially almost all human H5N1 isolates lost the avian consensus sequence for the SH3(II)bm prompted us to investigate the functionality of this motif in more detail.

Here, the inventors showed that NS1 proteins of avian but not of typical human strains strongly suppress the activity of the non-receptor tyrosine kinase c-Abl and that the SH3(II) bm of NS1 is required for this suppression. Mutational disruption of the SH3(II)bm consensus motif resulted in loss of c-Abl inhibition. Reconstitution of the functional domain in a H5N1 NS1 rescued the ability to suppress c-Abl kinase activity, clearly linking the NS1 to c-Abl kinase inhibition and demonstrating the involvement of the SH3(II)bm in this process. Introduction of the SH3(II)bm into the NS1 gene of a human IAV resulted in partial inhibition of c-Abl, which suggests that additional sequence elements present in avian NS1 proteins are required for complete kinase suppression. Additional sites, downstream of the SH3(II)bm, having a different avian or human consensus sequence may be also involved in regulation of c-Abl kinase inhibition. Interestingly, the inhibitory potential of NS1 protein against the human src kinase was illustrated recently and also linked to the SH3(II)bm and PDZ ligand domains (Bavagnoli, L., et al., PLoS One (2011) 6, e27789), confirming the ability of NS1 to interfere with additional tyrosine kinase mediated signalling events.

It is well established that CRKII is a transactivator of c-Abl kinase activity. However, the present data in essence exclude the involvement of CRKII in c-Abl inhibition in IAV infected cells and instead point to a direct interaction of the viral NS1 protein with the kinase. Interestingly, the NS1 proteins of both, avian and human IAV did bind to c-Abl, illustrating that binding and kinase inhibition are independent events mediated by different domains of the NS1. Therefore a two-step mechanism can be hypothesized, which includes an initial binding of NS1 to c-Abl that requires a sequence motif in the region aa88-125 and a subsequent kinase inhibition step dependent on the SH3(II) bm.

Interestingly, replication of avian IAV was hampered if the virus expressed an NS1 with the SH3(II)bm, independent of the avian virus strain or host cell, which were used for the experiments. Chemical inhibition of c-Abl did also affect avian IAV replication and growth advantages of avian IAV with a disrupted SH3(II)bm were impeded by c-Abl inhibitor treatment.

C-Abl has been shown to be involved in the cellular response to infections by several microbial agents (Backert, S., et al., Trends Biochem Sci (2008) 33, 80-90). As an example, the virus supportive impact of c-Abl on Ebola virus replication was recently determined being in line with our observation that c-Abl inhibition affects avian IAV propagation (Garcia, M., et al., Sci Transl Med (2012) 4, 123ra124). In general, NS1 is involved in several steps during replication (Hale et al., J Gen Virol, 2008, supra) and c-Abl exhibits plenty of functions (Sirvent, A., et al., Biol Cell (2008) 100, 617-631). However, we could neither detect an impact of c-Abl on viral polymerase activity or viral protein expression nor on the IAV induced type I IFN response, although c-Abl has been recently linked to MAVS induced signaling (Song, T., et al., FEBS Lett (2010) 584, 33-38). Furthermore, time of addition kinetics with the c-Abl inhibitor Imatinib negate an early to intermediate time point of virus replication as being affected by c-Abl inhibition.

Interestingly, genetic loss, knockdown or pharmacological inhibition of Abl leads to disruption of N-cadherin and E-cadherin based cell-cell contacts (Zandy et al., 2008, Zandy et al., 2007). Also, defects in the actin latticework were detected in c-Abl knockouts (Koleske et al., 1998) and the kinase was further linked to alterations of actin regulation and dynamics in the context of microbial infections (Backert et al., 2008, supra). Focusing on the cell morphology upon IAV infection, a strong cytopathogenic effect (CPE) was detectable upon avian IAV infection in contrast to human IAV. Blocking of the c-Abl inhibitory potential by disrupting the SH3(II)bm or restoration of the motif in H5N1 NS1 illustrated the clear interplay of cytopathogenic cell alterations and c-Abl inhibition. C-Abl mediated phosphorylation of Wave 3, a factor being essential for actin organization (Sossey-Alaoui, K., et al., J Biol Chem (2007) 282, 26257-26265) was also diminished by avian IAV infection, finally confirming the impact of the NS1 on cytoskeletal organization. In contrast, introduction of the functional SH3 (II)bm into the NS1 of a human prototype virus did only result in a slight reduction of c-Abl kinase activity and did not alter the cell shape upon infection, altogether illustrating the link between IAV-induced c-Abl kinase inhibition and cell morphology alterations. Therefore, we hypothesize that IAV-mediated c-Abl inhibition results in strong induction of CPE finally leading to a suppressed replication ability due to reduced virus production in pathologically altered host cells. Nevertheless, so far we cannot exclude a direct effect of the altered c-Abl kinase activity on viral protein regulation as shown for other microbials (Backert et al., 2008, supra; Garcia et al., 2012, supra). Even a specific effect of host cell factors only on the propagation of avian IAV was shown (Hrincius et al., 2010, supra).

Circulating avian IAV, except of the subtype H5N1, are characterized by possessing an SH3(II)bm in the NS1 protein, nevertheless, or data argue for a growth disadvantages of these prototype avian IAV in cell culture experiments. Keeping in mind that our data may not fully reflect the situation in vivo, we asked for biological explanations for this high conservation. One possibly feasible explanation for the high degree of conservation of the SH3(II)bm within NS1 proteins of avian IAV is an advantage of the c-Abl inhibitory potential in the special milieu of the avian intestine, which represents the major replication site of avian influenza viruses. Very interestingly, in contrast to e.g. H7 IAV, H5N1 IAV lost the consensus sequence of the SH3(II) bm. Taken into account that human infections with H5N1 from avian reservoir represents a crossing of species barriers and requires adaptation (Malik Peiris, J. S., Rev Sci Tech (2009) 28, 161-173), the observed increased overall replication ability in epithelia cells could be advantageous for efficient establishment of infection and mediation of severeness in the human host. These differences in the SH3(II)bm between highly pathogenic H5 and H7 viruses could help to understand the different ability of H5 and H7 strains to infect the human host and thereby could help to envision their different zoonotic potential.

In summary, the present data show that c-Abl is an interaction partner of the NS1 protein and that prototype avian IAV are able to block the c-Abl kinase activity. Regarding the still existing threat of pandemics occurring from avian reservoir, the inventors have further identified an additional protein differentially regulated by avian and human IAV being involved in virus replication and pathological host cell alterations.

Experimental Procedures

Cells, Viruses and Infection Conditions

Madin-Darby canine kidney (MDCK) cells were cultured in MEM, while the human lung epithelial cell line (A549) and the human embryonic kidney cells (HEK293) were cultivated in DMEM. Cell culture media were supplemented with 10% heat inactivated foetal bovine serum. The avian influenza virus A/FPV/Bratislava/79 (H7N7) (FPV) and the human influenza virus A/Puerto-Rico/8/34 (H1N1) (PR8) were obtained from the virus strain collection of the Institute of Virology, Giessen.

For generating the mouse adapted avian recombinant (rec.) influenza virus A/seal/Massachusetts/1/80 (H7N7) (SC35M) wild-type (SC35M wt), the according mutant virus rec. A/seal/Massachusetts/1/80 (H7N7) (SC35M) NS1-P215T (SC35M P215T), the highly pathogenic rec. influenza virus A/Thailand/1(KAN-1)/2004 (H5N1) wild-type (KAN-1 wt), the mutant virus rec. A/Thailand/1(KAN-1)/2004 (H5N1) NS1-L207P N212K (KAN-1 L207P N212K) (the depicted mutations in NS1 inevitable resulted in the mutations F55L and I60N in NS2), the human rec. influenza virus A/Puerto-Rico/8/34 (PR8) wild-type (PR8 rec. wt) and the according mutant virus rec. A/Puerto-Rico/8/34 (PR8) NS1-T215P (PR8 rec. T215P) the pHW2000 based reverse genetic system (Hoffmann, E., et al., Proc Natl Acad Sci USA (2000) 97, 6108-6113) was used as described earlier (Hrincius et al., 2010, supra). Primers used are shown in FIG. 15. Briefly, a set of eight plasmids allowing the rescue of these influenza virus strains was used for generating recombinant influenza viruses. To generate the recombinant viruses, 1 µg of each of the eight plasmids was transfected into HEK293 with Lipofectamine 2000 (Invitrogen) as described earlier (Basler, C. F., et al., Proc Natl Acad Sci USA (2000) 97, 12289-12294). Cells were grown in DMEM (100 U ml$^{-1}$ penicillin, 0.1 mg ml$^{-1}$ streptomycin, 0.5% heat inactivated foetal bovine serum and 0.2% BSA) and 24 h upon transfection cell culture medium was exchanged. Forty-eight hours post transfection the supernatant was removed and used for infection of MDCK cells. After 2-3 days incubation the supernatant was harvested and the virus titer was determined on MDCK cells by plaque assays. All viruses were propagated on eleven days old embryonated chicken eggs or Madin-Darby canine kidney (MDCK) cells. The presence and correctness of the desired mutation was confirmed by sequencing. For infection, cells were washed with phosphate-buffered saline (PBS) and incubated with IAV at the indicated multiplicities of infection (MOI) diluted in PBS containing 0.2% bovine serum albumin (BSA), 1 mM MgCl$_2$, 0.9 mM CaCl$_2$, 100 U ml$^{-1}$ penicillin, and 0.1 mg ml$^{-1}$ streptomycin for 30 min at 37° C. The inoculum was aspirated, and cells were incubated with either minimal essential medium (MEM) or Dulbecco modified Eagle medium (DMEM) containing 0.2% BSA and 100 U ml$^{-1}$ penicillin, and 0.1 mg ml$^{-1}$ streptomycin.

Standard Plaque Titration

Supernatants of infected cells were collected at the indicated times post infection (p.i.) and used to assess the number of infectious particles (plaque titres) in the samples. Briefly, MDCK cells grown to a monolayer in six-well dishes were washed with PBS and infected with serial dilutions of the collected supernatants in PBS/BA for 30 min at 37° C. The inoculum was aspirated and cells were supplemented with 2 ml MEM/BA (medium containing 0.2% BSA, 1 mM MgCl$_2$, 0.9 mM CaCl$_2$, 100 U ml$^{-1}$ penicillin and 0.1 mg ml$^{-1}$ streptomycin) containing 0.6% Agar (Oxoid), 0.3% DEAE-Dextran (Pharmacia Biotech) and 1.5% NaHCO$_3$ and incubated at 37° C. with 5% CO$_2$ for 2-3 days. Virus plaques were visualized by staining cells with neutral red and virus titres were depicted as PFU ml$^{-1}$.

Transient Transfections, Plasmids, siRNA, Inhibitors and Minireplicon Luciferase Assay Cells were transfected with Lipofectamine 2000 (Invitrogen) according to the Basler protocol (Basler et al., 2000). 24 h upon DNA-plasmid transfection and 48 h upon siRNA transfection cells were further treated. GST c-Abl was expressed by means of the plasmid pReceiver-M04-GST c-Abl (GeneCopoeia). The empty vector or the GST expressing vector was used as a control.

N-terminal HA-tagged full-length NS1 and C-terminal truncated NS1 versions (aa1-125 and aa1-88) (NS1 of the human IAV PR8) were expressed using the vector pTracer-CMV-HA. Down-regulation of CRKII expression was performed by siRNA transfection specific for CRKII (Santa Cruz), scrambled siRNA served as a control. The plasmid pcDNA3-CRKII was used for overexpression of CRKII and the empty vector served as a control.

The minireplicon luciferase assay was carried out as described earlier (Seyer, R., et al., J Infect Dis (2011) 205, 262-271). Briefly, cells were transfected with plasmids encoding an antisense luciferase reporter gene flanked by the influenza virus promoters of the M-segment (pHW72-luc vector) and the polymerase subunits PB2, PB1, PA and NP of the avian IAV A/FPV/Rostock/34 (H7N1) (pHW2000 vector). Cells were lysed and luciferase activity was measured 24 h after transfection. The c-Abl inhibitor Imatinib (LKT Laboratories) was dissolved in water and used in concentrations from 5-20 µM.

Immunoblot Analysis, Antibodies, Immunoprecipitation and GST Pull-Down

In general, immunoblotting and immunoprecipitation were performed as described previously (Hrincius et al., 2010, supra). Briefly, after treatment of cells, cells were lysed on ice with RIPA lysis buffer (25 mM Tris-HCl pH 8.0, 137 mM NaCl, 10% glycerol, 0.1% SDS, 0.5% DOC, 1% NP40, 2 mM EDTA pH 8.0, 5 µg ml-1 leupeptin, 5 µg ml-1 aprotinin, 0.2 mM pefablock, 1 mM sodium vanadate and 5 mM benzamidine) for 30 min. Cell lysates were cleared from debris by centrifugation and Bradford method was used for determination of protein concentrations. Cell lysates were used for analysis of protein expression by Western-blot (WB). For immunoprecipitation (IP) cells were lysed on ice with Triton lysis buffer (TLB) (20 mM Tris-HCl pH 7.4, 137 mM NaCl, 10% glycerol, 1% Triton X-100, 2 mM EDTA, 50 mM sodium glycerophosphate, 20 mM sodium pyrophosphate, 5 µml-1 leupeptin, 5 µml-1 aprotinin, 0.2 mM pefablock, 1 mM sodium vanadate and 5 mM benzamidine) for 30 min. Cell lysates were processed as described above. For IP, the following antibodies were used; rabbit anti-NS1 polyclonal antibody (pAb) (Thorsten Wolff, RKI, Berlin), rabbit anti-CRKL (C-20) pAb (Santa Cruz), mouse anti-c-Abl (24-11) monoclonal antibody (mAb)

(Santa Cruz) and rabbit anti-Wave 3 pAb (Millipore) coupled to protein A or G agarose (Roche). Serum of non-immunized mice or rabbit was used for control purposes. For GST pull-down, cell lysates were mixed and incubated with glutathione sepharose beads (GE Healthcare). For IP-input and GST pull-down input controls, lysates were directly subjected to SDS-PAGE and Western blot.

For determination of c-Abl kinase activity, the phosphorylation of CRKII was monitored with a rabbit anti-CRKII [pY221] pAb (Cell Signaling) and of CRKL with a rabbit anti-CRKL [pY207] pAb (Cell Signaling). For detection of broad tyrosine phosphorylation the mouse anti-phosphotyrosine (4G10) mAb (Millipore) was used.

CRKI/II and CRKL were detected by a mouse anti-CRKI/II mAb (BD Transduction Laboratories) and a rabbit anti-CRKL (C-20) pAb (Santa Cruz) or a mouse anti-CRKL (clone 5-6) mAb (Millipore). A rabbit anti-c-Abl pAb (Cell Signaling) was used for detection of c-Abl and an anti-ERK2 (C-14) rabbit pAb (Santa Cruz) for detection of ERK2. Wave 3 protein was visualized by a rabbit anti-Wave 3 pAb (Millipore). Detection of GST c-Abl fusion protein was conducted by an mouse anti-GST mAb (IMV Muenster, Germany) and measurement of HA-tagged NS1 was achieved by an mouse anti-HA mAb (IMV Muenster, Germany).

The NS1 protein was visualized by the NS1 rabbit pAb mentioned above or by a mouse anti-NS1 (clone NS1-23-1) mAb (IMV Muenster, Germany). Detection of the additional viral proteins PB1, NP and M1 was done by a goat anti-PB1 pAb (Santa Cruz), a mouse anti-NP mAb (Serotec) and a mouse anti-M1 mAb (Serotec).

Protein bands were visualized by a standard enhanced chemiluminescence reaction.

In Vitro Kinase Assay

For measurement of c-Abl kinase activity an in vitro kinase assay was performed. After immunoprecipitation of c-Abl, IP was washed twice with TLB and RICK buffer (10 mM $MgCl_2$, 25 mM Hepes pH 7.5, 1.08 g/200 ml β-glycerophosphat, 5 mM benzamidine, 0.5 mM DTT and 1 mM sodium vanadate), then incubated with 2.5 µg MBP and 100 µM (final) ATP in Rick buffer for 30 min at 30° C. and 1050 rpm. Finally, samples were supplemented with 5×SDS loading dye and subjected to SDS-PAGE and Western blot.

Western Blot Quantification

Quantification of Western blot experiments was conducted using ImageJ software. Total band intensity was measured and obtained values for the specific bands were divided through the values of loading or precipitation controls.

Isolation of RNA and Quantitative Real-Time-PCR (qRT-PCR)

Total RNA from treated or untreated cells was isolated with the RNeasy mini kit (Qiagen) according to the manufacturer's instructions. For reverse transcription of mRNA 40 1 µg total RNA and 0.5 µg oligo dT primer in a total volume of 12 µl were heated for 10 min at 70° C. Enzyme mix was prepared (5× Enzyme Buffer (Fermentas), H2O and 500 µM dNTPs) and incubated at RT for 5 min before 535 units per 100 ml RevertAid HM-MuLV (Fermentas) were added to initiate reverse transcription at 42° C. for 1 h. Inactivation of the reverse transcriptase was done at 70° C. for 5 min. For the qRT-PCR reaction Brilliant QPCR SYBR Green Mastermix (Stratagene) was 5 used according to manufacturer's instructions. Relative RNA levels were determined after 40 cycles of amplification by using the $2^{-\Delta\Delta CT}$ method (Livak, K. J., and Schmittgen, T. D., Methods (2001) 25, 402-408). The housekeeping gene GAPDH served as internal standard. The following primers were used: GAPDH (NM_002046.3) fwd 5'-GCAAATTTC-CATGGCACCGT-3' (SEQ ID NO: 48), GAPDH 10 rev 5'-GCCCCACTTGATTTTGGAGG-3' (SEQ ID NO: 49), IFNβ (NM_002176.2) fwd 5'-GGCCATGACCAACAAGT-GTCTCCTCC-3' (SEQ ID NO: 50), IFNβ rev 5'-GCGCTCAGTTTCGGAGGTAACCTGT-3' (SEQ ID NO: 51).

Microscopy and Indirect Analysis

For microscopic analysis, images of infected or uninfected cells were taken using the Axiovert 40C microscope (Zeiss) and a camera (Canon) (10× objective lens).

For indirect immunofluorescence analysis, cells were seeded onto glass-plates. After infection of cells for 8 h, cells were washed twice with PBS and then fixed with 3.7% paraformaldehyde (in PBS) at room temperature for 30 min. After additional washing, cells were permeabilized by consecutively incubation with 30%, 60% and finally 100% acetone for 5 min, afterwards washed and blocked with 10% FCS in PBS for 30 min at 37° C. After blocking, cells were incubated with a mouse anti-NP mAb (Serotec) in PBS for 1 h. After further washing, cells were incubated with an Alexa Fluor 568 goat anti-mouse IgG (H+L) (Invitrogen), DAPI (Sigma) for nuclear staining and Alexa Fluor 488 Phalloidin for actin staining (Invitrogen) in PBS for 1 h. Finally, cells were washed again, embedded and fluorescence was visualized using the fluorescence microscope Axiovert 200M (Zeiss) (40× objective lens).

What is claimed is:

1. A method of treating a BCR-ABL associated disease or a c-ABL associated disease selected from the group consisting of chronic myeloid leukaemia (CML), acute lymphatic leukaemia (ALL), acute myeloic leukaemia (AML) and a c-ABL associated leukemia in a subject in need thereof, the method comprising administering to the subject a nonstructural protein 1 (NS1), wherein the NS1 protein comprises the amino acid sequence of SEQ ID NO: 1 and $PPX_{13}PX_1X_{16}$ (SEQ ID NO: 107), wherein $X_1$ is any amino acid, $X_{13}$ is selected from the group consisting of A, C, G, I, L, M, F, P, W and V, and $X_{16}$ is K or R.

2. The method of claim 1, wherein the NS1 protein is administered into a cell of the subject.

3. The method of claim 2, wherein the cell is a somatic cell.

* * * * *